United States Patent
Kambe et al.

(10) Patent No.: US 10,573,823 B2
(45) Date of Patent: *Feb. 25, 2020

(54) ORGANIC ELECTROLUMINESCENT DEVICE

(71) Applicant: JOLED INC, Tokyo (JP)

(72) Inventors: Emiko Kambe, Tokyo (JP); Masato Nakamura, Tokyo (JP); Masakazu Funahashi, Sodegaura (JP); Hiroshi Yamamoto, Sodegaura (JP); Sayaka Mizutani, Sodegaura (JP)

(73) Assignee: JOLED INC, Tokyo (JP)

(*) Notice: Subject to any disclaimer, the term of this patent is extended or adjusted under 35 U.S.C. 154(b) by 1035 days.

This patent is subject to a terminal disclaimer.

(21) Appl. No.: 14/387,835

(22) PCT Filed: Mar. 22, 2013

(86) PCT No.: PCT/JP2013/001946
§ 371 (c)(1),
(2) Date: Sep. 24, 2014

(87) PCT Pub. No.: WO2013/145666
PCT Pub. Date: Oct. 3, 2013

(65) Prior Publication Data
US 2015/0303380 A1    Oct. 22, 2015

(30) Foreign Application Priority Data

Mar. 29, 2012 (JP) ................... 2012-076216

(51) Int. Cl.
*H01L 51/00* (2006.01)
*H01L 51/52* (2006.01)
(Continued)

(52) U.S. Cl.
CPC ........ *H01L 51/0072* (2013.01); *C07C 255/34* (2013.01); *C07C 255/35* (2013.01); *C07C 255/37* (2013.01); *C07C 255/41* (2013.01); *C07C 255/50* (2013.01); *C07C 255/61* (2013.01); *C07C 261/04* (2013.01); *C07D 471/04* (2013.01); *C07D 487/14* (2013.01); *H01L 51/0052* (2013.01); *H01L 51/0054* (2013.01); *H01L 51/0055* (2013.01); *H01L 51/0056* (2013.01); *H01L 51/0058* (2013.01); *H01L 51/0067* (2013.01); *H01L 51/0068* (2013.01); *H01L 51/0073* (2013.01); *H01L 51/0074* (2013.01); *H01L 51/5278* (2013.01); *C07C 2603/40* (2017.05);
(Continued)

(58) Field of Classification Search
CPC combination set(s) only.
See application file for complete search history.

(56) References Cited

U.S. PATENT DOCUMENTS 6,107,734 A    8/2000  Tanaka et al.
9,181,474 B2 * 11/2015 Kim ................. C07D 213/74
(Continued)

FOREIGN PATENT DOCUMENTS

JP    11-329748 A    11/1999
JP    2003-045676   2/2003
(Continued)

OTHER PUBLICATIONS

U.S. Appl. No. 14/387,824, filed Sep. 2014, Kambe et al.*
(Continued)

*Primary Examiner* — Amanda L Aguirre
(74) *Attorney, Agent, or Firm* — Sheridan Ross P.C.

(57) ABSTRACT

An organic electroluminescence device including: an anode; a cathode; two or more emitting units that are disposed between the anode and the cathode, each unit having an emitting layer; and a charge-generating layer that is disposed between the emitting units, wherein the charge-generating layer includes an N layer nearer to the anode and a P layer nearer to the cathode, and the N layer includes a compound represented by the following formula (I) or (II):

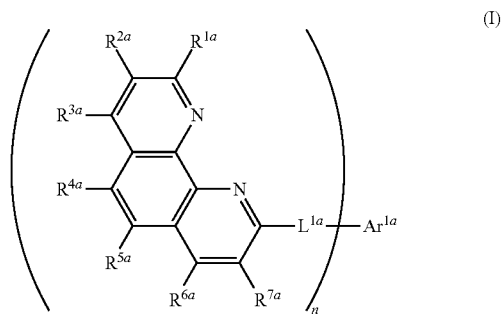

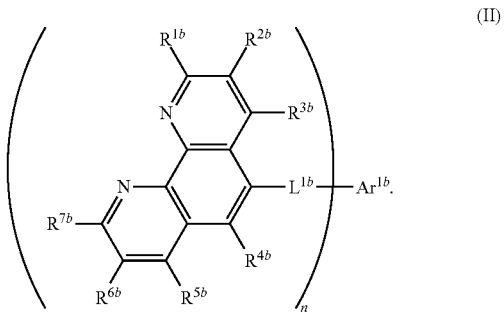

9 Claims, 3 Drawing Sheets

(51) Int. Cl.
  H01L 51/50    (2006.01)
  C07D 471/04   (2006.01)
  C07C 255/37   (2006.01)
  C07D 487/14   (2006.01)
  C07C 255/35   (2006.01)
  C07C 255/61   (2006.01)
  C07C 255/34   (2006.01)
  C07C 255/41   (2006.01)
  C07C 261/04   (2006.01)
  C07C 255/50   (2006.01)
  H01L 27/32    (2006.01)

(52) U.S. Cl.
  CPC ...... C07C 2603/52 (2017.05); C07C 2603/54 (2017.05); H01L 27/322 (2013.01); H01L 27/3209 (2013.01); H01L 27/3281 (2013.01); H01L 51/0051 (2013.01); H01L 51/504 (2013.01); H01L 51/5056 (2013.01); H01L 51/5088 (2013.01); H01L 51/5206 (2013.01); H01L 51/5221 (2013.01); H01L 2251/533 (2013.01)

(56)  References Cited

U.S. PATENT DOCUMENTS

| | | | |
|---|---|---|---|
| 9,978,975 B2 * | 5/2018 | Kambe | ............... C07D 487/14 |
| 2003/0170491 A1 | 9/2003 | Liao et al. | |
| 2003/0189401 A1 | 10/2003 | Kido et al. | |
| 2005/0029933 A1 | 2/2005 | Liao et al. | |
| 2006/0008740 A1 | 1/2006 | Kido et al. | |
| 2007/0181887 A1 | 8/2007 | Kijima et al. | |
| 2007/0182317 A1 | 8/2007 | Kido et al. | |
| 2010/0108990 A1 * | 5/2010 | Hosokawa | ........... C07D 471/04 257/40 |
| 2012/0118350 A1 | 5/2012 | Kido et al. | |
| 2012/0132895 A1 | 5/2012 | Kido et al. | |
| 2014/0151648 A1 | 6/2014 | Kido | |

FOREIGN PATENT DOCUMENTS

| | | |
|---|---|---|
| JP | 2003-272860 A | 9/2003 |
| JP | 2004-039617 A | 2/2004 |
| JP | 2006-024791 A | 1/2006 |
| JP | 2006-073484 A | 3/2006 |
| JP | 2006-173550 A | 6/2006 |
| JP | 2009-521110 A | 5/2009 |
| JP | 2011-086442 A | 4/2011 |
| JP | 2012-022953 A | 2/2012 |
| WO | WO-2007/018004 A1 | 2/2007 |
| WO | WO-2010/132236 A1 | 11/2010 |
| WO | WO-2011/046166 A1 | 4/2011 |

OTHER PUBLICATIONS

International Preliminary Report on Patentability and Written Opinion issued in Application No. PCT/JP2013/001946 dated Oct. 9, 2014.

International Search Report issued in PCT/JP2013/001946 dated Jun. 18, 2013.

* cited by examiner

ORGANIC ELECTROLUMINESCENT DEVICE

CROSS REFERENCE TO RELATED APPLICATIONS

The present application is a National Stage of International Application No. PCT/JP2013/001946 filed on Mar. 22, 2013, which claims the benefit of Japanese Appln. No. 2012-076216 filed Mar. 29, 2012, the entire disclosures of which are incorporated herein by reference.

TECHNICAL FIELD

The invention relates to an organic electroluminescence (EL) device. In particular, the invention relates to a stacked multi-photon emission (MPE) device having two or more emitting units.

BACKGROUND ART

A common organic EL device comprises an anode that is provided on a substrate and is made of an ITO or the like, an organic layer provided on the anode and a cathode provided on the top of it. The organic layer has a configuration in which a hole-injecting layer, a hole-transporting layer and an emitting layer are stacked in sequence from the side of the anode, for example. In an organic EL device having such a configuration, light that is emitted when electrons injected from a cathode and holes injected from an anode are recombined in an emitting layer is outcoupled from the substrate.

In general, the life of an organic EL device is determined by the amount of injected charges. Therefore, there is a problem that, if the driving current is increased in order to increase the initial luminance, the life is shortened with an increase in driving current.

In order to solve the problem, it is required to increase the luminance without changing the driving current (i.e. to increase the efficiency) or to realize a device configuration that can obtain the equivalent luminance even if the driving current is lowered.

As the above-mentioned device configuration, a configuration (MPE device) in which a plurality of emitting units each comprising organic layers that at least include an emitting layer are stacked between an anode and a cathode through an insulating charge-generating layer has been proposed. Here, the charge-generating layer is a layer that serves, at the time of application of a voltage, to inject holes to an emitting unit that is provided on the side nearer to the cathode of the charge-generating layer, and to inject electrons to an emitting unit that is provided on the side nearer to the anode of the charge-generating layer.

In a stacked organic EL device obtained by stacking emitting units through the charge-generating layer, it is believed as follows. That is, when two emitting units are stacked, the luminance [cd/A] can be doubled ideally with the luminous efficiency [lm/W] being unchanged, and when three emitting units are stacked, the luminance can be tripled ideally with the luminous efficiency [lm/W] being unchanged.

As for an MPE device, in Patent Documents 1 and 3, for example, a device using a transparent conductor (e.g. ITO, IZO) in a charge-generating layer is disclosed.

In Patent Document 2, a device using vanadium oxide ($V_2O_5$) or rhenium heptoxide ($Re_2O_7$) in a charge-generating layer is disclosed. Patent Document 4 discloses a device using a metal oxide such as molybdenum oxide ($MoO_3$) or a metal salt such as iron chloride ($FeCl_3$) is used in a charge-generating layer. Patent Document 5 discloses a device using a combination of an N-dope layer and a P-dope layer in a charge-generating layer. Patent Document 6 discloses a device using a phthalocyanine compound in a charge-generating layer. Patent Document 7 discloses a device using hexazatriphenylene (HAT) and an electron-accepting organic substance disclosed in Patent Document 2 (e.g. F4TCNQ) in a charge-generating layer.

As mentioned above, although various materials are used in a charge-generating layer, there are some problems associated with conventional charge-generating layers.

Specifically, since a high temperature is required when an inorganic substance such as a metal oxide is formed into a film by deposition, the efficiency of film-forming process is lowered, resulting in poor mass productivity.

Further, since a transparent conductor such as an ITO has a high electric conductivity, current leakage between pixels through a charge-generating layer may occur. Therefore, when a desired pixel is caused to emit light, adjacent pixels may also emit light. This phenomenon becomes a problem especially in the case of a display in which an organic EL device is allowed to emit white color and each of RGB colors is outcoupled through a color filter provided on the device. That is, since color purity is significantly lowered due to occurrence of color mixing by emission of adjacent pixels, color reproducibility is lowered.

In addition, damage to organic layers serving as underlying layers by generated plasma particles is concerned at the time of forming a transparent conductor by sputtering or the like.

On the other hand, when an organic compound is used, in general, the temperature at the time of film formation is low and no plasma particles are generated. Therefore, the efficiency of film formation process or mass productivity is excellent. When an electron-accepting organic compound is used, as shown in Patent Document 7, in particular, a device having excellent properties such as efficiency, voltage and life can be obtained when HAT is used. However, since HAT itself has high conductivity, as in the case of the above-mentioned transparent conductor, current leakage between pixels through a charge-generating layer may occur.

RELATED ART DOCUMENT

Patent Documents

Patent Document 1: JP-A-2003-45676
Patent Document 2: JP-A-2003-272860
Patent Document 3: JP-A-H11-329748
Patent Document 4: JP-A-2006-24791
Patent Document 5: JP-A-2004-39617
Patent Document 6: JP-A-2006-73484
Patent Document 7: JP-A-2006-173550

SUMMARY OF THE INVENTION

An object of the invention is to provide a stacked MPE device that has a high luminous efficiency and can be driven at a low voltage. The invention is also aimed at providing a stacked MPE device that can suppress current leakage between pixels when a device forms pixels.

The inventors made intensive studies in order to solve the above-mentioned problem. As a result, the inventors have found that, by using a prescribed compound in a charge-generating layer, a stacked MPE device that has a high luminous efficiency and can be driven at a low voltage can be obtained, and that current leakage between pixels can also be suppressed. The invention has been attained based on this finding.

According to the invention, the following organic EL device is provided:
1. An organic electroluminescence device comprising:
   an anode;
   a cathode;
   two or more emitting units that are disposed between the anode and the cathode, each unit having an emitting layer; and
   a charge-generating layer that is disposed between the emitting units,
   wherein the charge-generating layer comprises an N layer nearer to the anode and a P layer nearer to the cathode, and
   the N layer comprises a compound represented by the following formula (I) or (II):

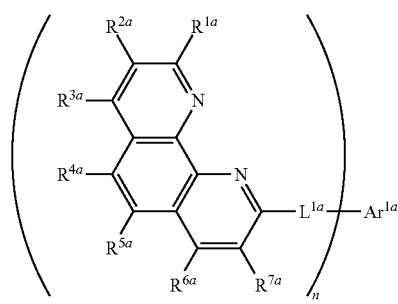

(I)

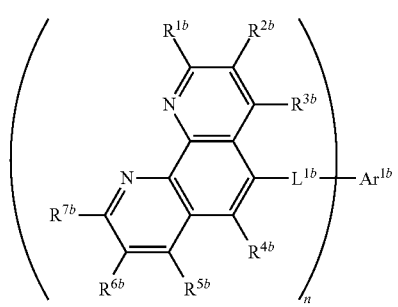

(II)

wherein in the formulas,
$R^{1a}$ to $R^{7a}$ and $R^{1b}$ to $R^{7b}$ are independently a hydrogen atom, a substituted or unsubstituted aryl group including 6 to 60 carbon atoms that form a ring (hereinafter referred to as "ring carbon atoms"), a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, an amino group that is substituted with a substituted or unsubstituted aryl group including 6 to 50 ring carbon atoms, a halogen atom, a cyano group, a nitro group, a hydroxyl group or a carboxyl group, and adjacent groups of $R^{1a}$ to $R^{7a}$ or adjacent groups of $R^{1b}$ to $R^{7b}$ may be bonded each other to form a ring;

$L^{1a}$ and $L^{1b}$ are independently a single bond or a linkage group;

$Ar^{1a}$ and $Ar^{1b}$ are independently a substituted or unsubstituted aromatic group including 6 to 60 carbon atoms; and n is an integer of 1 to 4, and when n is 2 or more, the groups having a phenanthroline skeleton in parentheses may be the same or different from each other.

2. The organic electroluminescence device according to 1, wherein the compound represented by the formula (I) or (II) is a compound represented by the following formula (I-a), (I-b), (II-a) or (II-b):

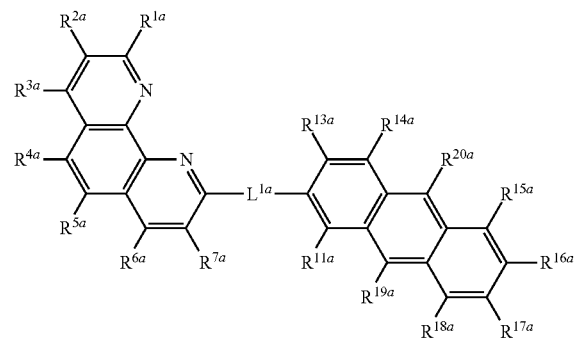

(I-a)

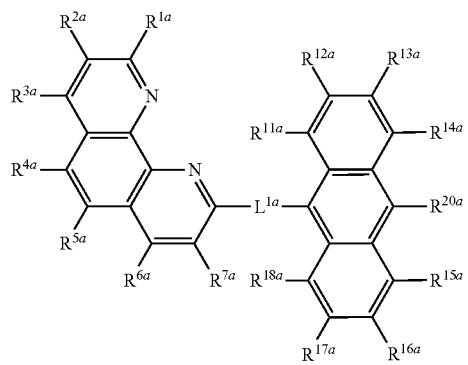

(I-b)

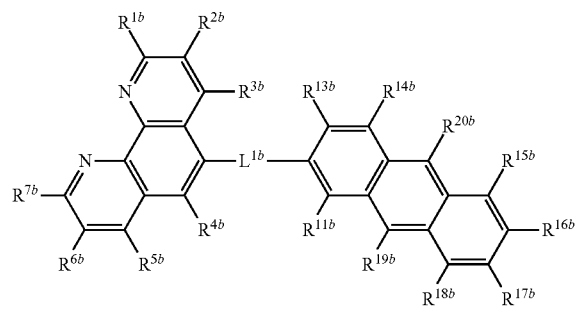

(II-a)

-continued

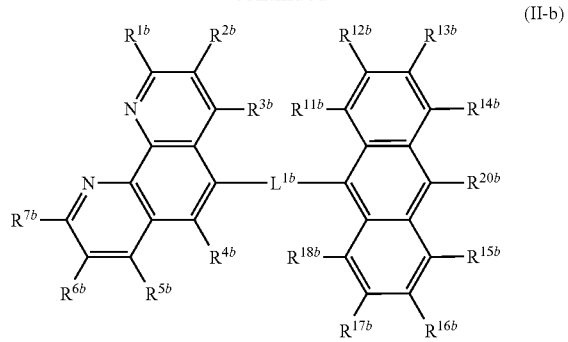
(II-b)

wherein in the formulas,
$R^{1a}$ to $R^{7a}$ and $R^{1b}$ to $R^{7b}$ are the same as those in the formulas (I) and (II);
$R^{11a}$ to $R^{20a}$ and $R^{11b}$ to $R^{20b}$ are independently a hydrogen atom, a substituted or unsubstituted aryl group including 6 to 60 ring carbon atoms, a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 5 to 50 ring carbon atoms, a substituted or unsubstituted alkoxycarbonyl group including 2 to 50 carbon atoms, an amino group that is substituted with a substituted or unsubstituted aryl group including 6 to 50 ring carbon atoms, a halogen atom, a cyano group, a nitro group, a hydroxyl group or a carboxyl group, and adjacent groups of $R^{11a}$ to $R^{20a}$ or adjacent groups of $R^{11b}$ to $R^{20b}$ may be bonded each other to form a ring; and
$L^{1a}$ and $L^{1b}$ are independently a single bond or a linkage group.

3. The organic electroluminescence device according to 1 or 2, wherein the N layer of the charge-generating layer comprises at least one of an electron-donating metal, an electron-donating metal compound and an electron-donating metal complex.

4. The organic electroluminescence device according to 3, wherein the N layer of the charge-generating layer comprises at least one of an alkali metal, an alkali earth metal, a simple substance of a rare earth metal, a compound of a rare earth metal and a complex of a rare earth metal.

5. The organic electroluminescence device according to any of 1 to 4, wherein the P layer comprises a compound represented by the following formula (III):

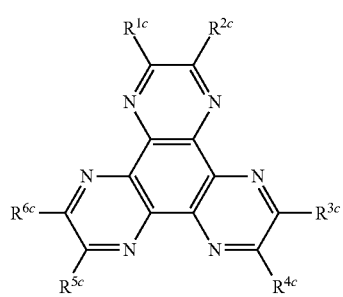
(III)

wherein in the formula, $R^{1c}$ to $R^{6c}$ are independently a hydrogen atom, a substituted or unsubstituted aryl group including 6 to 60 ring carbon atoms, a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, an amino group that is substituted with a substituted or unsubstituted aryl group including 6 to 50 ring carbon atoms, a halogen atom, a cyano group, a nitro group, a hydroxyl group or a carboxyl group.

6. The organic electroluminescence device according to any of 1 to 4, wherein the P layer comprises a compound represented by the following formula (IV):

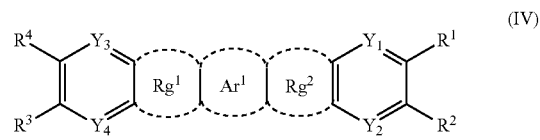
(IV)

wherein in the formula (IV), $Ar^1$ is an aromatic ring including 6 to 24 ring carbon atoms, or a heterocyclic ring including 5 to 24 atoms that form a ring (hereinafter referred to as "ring atoms"), and
$Rg^1$ and $Rg^2$ may be the same or different from each other and are presented by the following formula (i) or (ii):

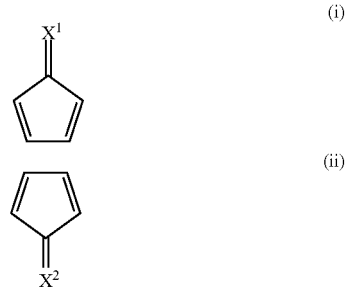
(i)

(ii)

wherein $X^1$ and $X^2$ may be the same or different from each other and are represented by any of divalent groups represented by the following (a) to (g):

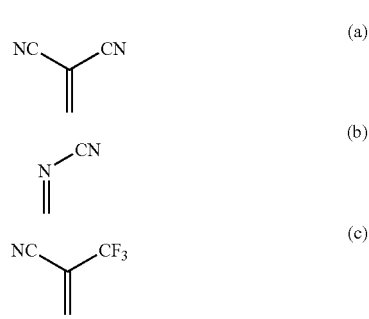
(a)

(b)

(c)

-continued

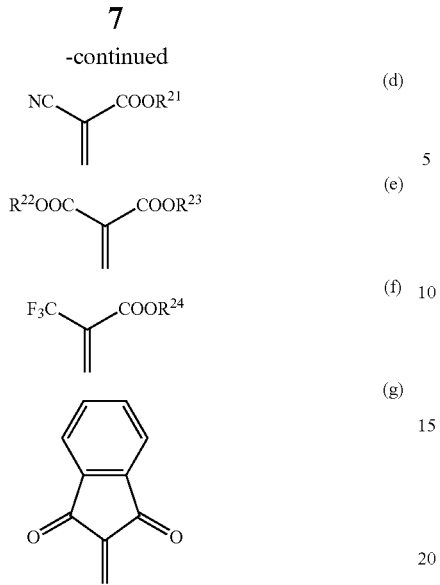

wherein $R^{21}$ to $R^{24}$ may be the same or different from each other, and are a hydrogen atom, a substituted or unsubstituted fluoroalkyl group, a substituted or unsubstituted alkyl group, a substituted or unsubstituted aryl group or a substituted or unsubstituted heterocyclic group, and $R^{22}$ and $R^{23}$ may be bonded each other to form a ring;

$R^1$ to $R^4$ may be the same or different from each other, and a hydrogen atom, a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxy group, a substituted or unsubstituted fluoroalkoxy group, a substituted or unsubstituted aryloxy group, a substituted or unsubstituted aralkyloxy group, a substituted or unsubstituted amino group, a substituted or unsubstituted silyl group, or a cyano group, and $R^1$ and $R^2$ may be bonded each other to form a ring and $R^3$ and $R^4$ may be bonded each other to form a ring; and $Y^1$ to $Y^4$ may be the same or different from each other, and are independently N, CH, or $C(R^5)$, and $R^5$ is the same as $R^1$ to $R^4$.

7. The organic electroluminescence device according to any of 1 to 6, wherein at least one of materials constituting the emitting layers of the emitting units is different from a material constituting the emitting layer(s) of the other emitting unit(s).

8. The organic electroluminescence device according to any of 1 to 7, which emits white light.

According to the invention, it is possible to provide a stacked organic EL device that has a high luminous efficiency and can be driven at a low voltage. Further, according to the invention, it is possible to suppress occurrence of current leakage between pixels.

MODE FOR CARRYING OUT THE INVENTION

The organic EL device of the invention has a configuration in which two or more emitting units are disposed between an anode and a cathode, and a charge-generating layer is disposed between the emitting units.

Figure 1:
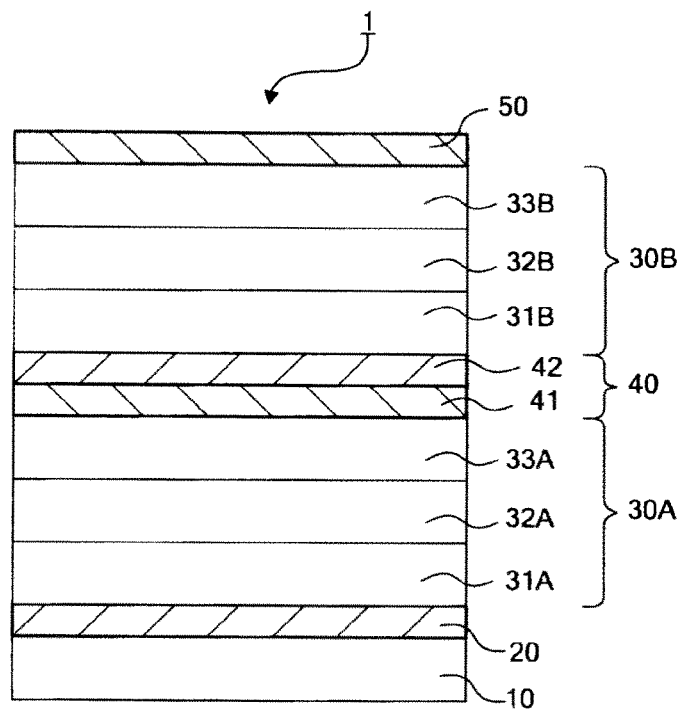
FIG. 1 is a schematic cross-sectional view showing one embodiment of the organic EL device according to the invention.

FIG. 1 is a schematic cross-sectional view of one embodiment of the organic EL device of the invention.

An organic EL device 1 has, on a substrate 10, an anode 20, a first emitting unit 30A, a charge-generating layer 40, a second emitting unit 30B and a cathode 50 in this sequence.

The first emitting unit 30A and the second emitting unit 30B emit light by re-combination of electrons and holes. The two emitting units respectively have a single-layer structure or a stacked layer structure including at least the emitting layers 32A and 32B. In this embodiment, the emitting unit has a multi-layer structure in which a hole-transporting layer 31, an emitting layer 32 and an electron-transporting layer 33 are stacked from the anode side.

The charge-generating layer 40 is a layer that serves to generate holes and electrons at the time of applying a voltage, and inject holes to the emitting unit provided on the side nearer to the cathode 50 of the charge-generating layer 40 (i.e. the second emitting unit 30B), and inject electrons to the emitting unit provided on the side nearer to the anode 20 of the charge-generating layer 40 (i.e. the first emitting unit 30A).

In the invention, the charge-generating layer 40 has an N layer 41 formed on the anode side and a P layer 42 formed on the cathode side. The N layer 41 contains a compound represented by the following formula (I) or (II):

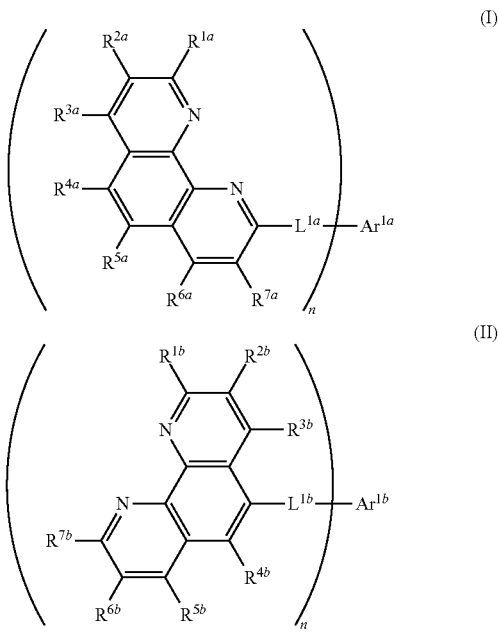

By using the compound represented by the above-mentioned formula (I) or (II) in the N layer, an organic EL device that has a high luminous efficiency and can be driven at a low voltage can be obtained. Further, since a charge-generating layer can be formed at a low deposition temperature, efficiency of the film-forming process or mass productivity can be improved. In addition, when a plurality of organic EL devices are formed on a plane to form a pixel, current leakage between adjacent pixels can be suppressed.

Hereinbelow, the compound represented by the formulas (I) and (II), by which the invention is characterized, will be explained.

In the above-mentioned formulas (I) and (II), $R^{1a}$ to $R^{7a}$ and $R^{1b}$ to $R^{7b}$ are independently a hydrogen atom, a substituted or unsubstituted aryl group including 6 to 60 ring carbon atoms, a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, an amino group substituted with a substituted or unsubstituted aryl group including 6 to 50 ring carbon atoms, a halogen atom, a cyano group, a nitro group, a hydroxyl group or a carboxyl group.

Adjacent groups of $R^{1a}$ to $R^{7a}$ or adjacent groups of $R^{1b}$ to $R^{7b}$ may be bonded each other to form a ring. Examples of the ring include a benzene ring, a naphthalene ring, a pyrazine ring, a pyridine ring, a furan ring or the like.

$L^{1a}$ and $L^{1b}$ are independently a single bond or a linkage group. As the linkage group, a substituted or unsubstituted aromatic group including 6 to 20 ring carbon atoms, a substituted or unsubstituted alkylene chain including 1 to 8 carbon atoms and a substituted or unsubstituted heterocyclic ring can be given. Specifically, a substituted or unsubstituted benzene ring, a substituted or unsubstituted naphthalene ring, a substituted or unsubstituted methylene chain or a substituted or unsubstituted pyridine ring are preferable.

$Ar^{1a}$ and $Ar^{1b}$ are independently a substituted or unsubstituted aromatic group including 6 to 60 carbon atoms.

n is 1 to 4, and when n is 2 or more, the groups having a phenanthroline skeleton in parentheses may be the same or different.

As the compound represented by the formula (I) or (II), the compound represented by the following formula (I-a), (I-b), (II-a) or (II-b) is preferable.

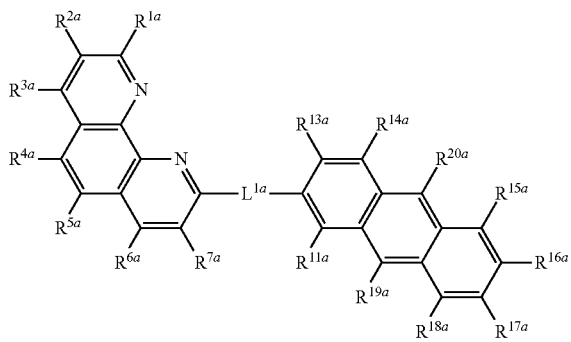

(I-a)

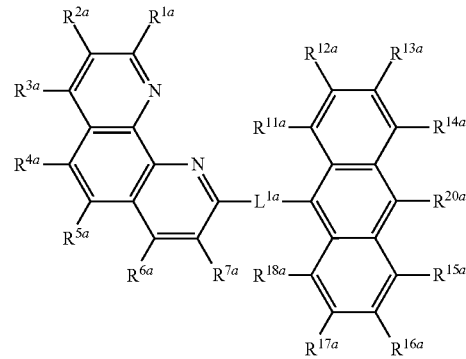

(I-b)

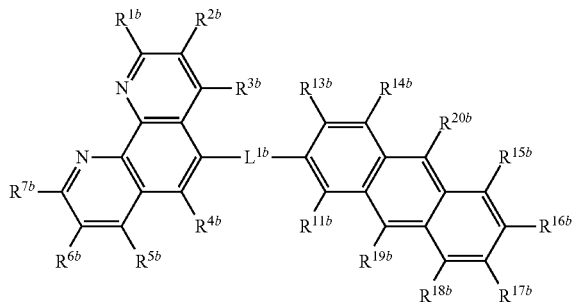

(II-a)

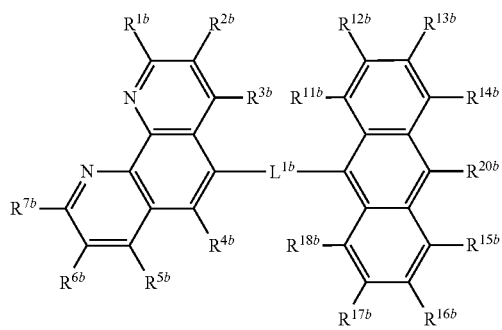

(II-b)

Due to the presence of a group having a phenanthroline skeleton and a group having an anthracene skeleton, it becomes possible to have both a function as an electron acceptor and a transporting function as an electron-transporting layer. Further, deposition stability or film forming property are improved.

In the formulas (I-a), (I-b), (II-a) and (II-b), $R^{1a}$ to $R^{7a}$, $R^{1b}$ to $R^{7b}$ and $L^{1a}$ and $L^{1b}$ are independently the same groups as $R^{1a}$ to $R^{7a}$, $R^{1b}$ to $R^{7b}$ and $L^{1a}$ and $L^{1b}$ in the formulas (I) and (II).

$R^{11a}$ to $R^{20a}$ and $R^{11b}$ to $R^{20b}$ are independently a hydrogen atom, a substituted or unsubstituted aryl group including 6 to 60 ring carbon atoms, a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 5 to 50 ring carbon atoms, a substituted or unsubstituted alkoxycarbonyl group including 2 to 50 carbon atoms, an amino group substituted with a substituted or unsubstituted aryl group including 6 to 50 ring carbon atoms, a halogen atom, a cyano group, a nitro group, a hydroxyl group or a carboxyl group.

Adjacent groups of $R^{11a}$ to $R^{20a}$ or adjacent groups of $R^{11b}$ to $R^{20b}$ may be bonded each other to form a ring. Examples of the ring include a benzene ring, a naphthalene ring, a pyrazine ring, a pyridine ring, a furan ring or the like.

Hereinbelow, an explanation will be made on examples of each group in the above-mentioned formula (I) or the like.

In this specification, the aryl group includes a monocyclic aromatic hydrocarbon ring group and a fused aromatic hydrocarbon ring group in which a plurality of hydrocarbon rings are fused. The heteroaryl group includes a monocyclic heteroaromatic ring group, a heterofused aromatic ring group in which a plurality of heteroaromatic rings are fused and a heterofused aromatic ring group in which an aromatic hydrocarbon ring and a heteroaromatic ring are fused.

The "unsubstituted" in the "substituted or unsubstituted . . ." means substitution by a hydrogen atom. The hydrogen atom in the compound of the invention includes protium, deuterium and tritium, The ring carbon atoms (nucleus carbons) mean carbon atoms that constitute an aromatic ring. The ring atoms (nucleus atoms) mean carbon atoms and hetero atoms that constitute a heterocyclic ring (including a saturated ring, an unsaturated ring and an aromatic heterocyclic ring).

The aryl group including 6 to 60 ring carbon atoms is preferably an aryl group including 6 to 30, particularly preferably 6 to 20, carbon atoms. Examples thereof include phenyl, fluorenyl, naphthyl, anthryl, phenanthryl, chrysenyl, pyrenyl, triphenylenyl, fluoranthenyl or the like.

As the aromatic group indicated by $Ar^{1a}$ and $Ar^{1b}$, the aryl group mentioned above and a divalent or larger group obtained by removing a hydrogen atom from the aryl group can be given.

As $R^{1a}$ to $R^{7a}$ and $R^{1b}$ to $R^{7b}$ in the formulas (I) and (II), hydrogen, phenyl and naphthyl are preferable.

As the alkyl group including 1 to 50 carbon atoms, a linear or branched alkyl group can be given. The alkyl group is preferably one including 1 to 20, more preferably 1 to 12 and particularly preferably 1 to 8 carbon atoms. Examples include methyl, ethyl, propyl, butyl, pentyl and hexyl.

As the cycloalkyl group including 3 to 50 ring carbon atoms, cyclopentyl, cyclohexyl or the like can be given.

The aralkyl group including 7 to 50 ring carbon atoms is expressed as —Y—Z. As examples of Y, examples of alkylene corresponding to examples of the above-mentioned alkyl group can be given. As examples of Z, examples of the above-mentioned aryl group can be given. The aryl part of the aralkyl group preferably includes 6 to 30 carbon atoms. The alkyl part preferably includes 1 to 10 carbon atoms, with 1 to 6 being particularly preferable. The alkyl part is a benzyl group, a phenylethyl group or a 2-phenylpropane-2-yl group, for example.

The alkoxy group including 1 to 50 carbon atoms is expressed as —OY. As examples of Y, examples of the above-mentioned alkyl group can be given. The alkoxy group preferably includes 1 to 20, more preferably 1 to 12, and particularly preferably 1 to 8 carbon atoms. The alkoxy group is methoxy, ethoxy, propoxy, butoxy or the like, for example.

The aryloxy group including 6 to 50 ring carbon atoms is expressed as —OY As examples of Y, examples of the above-mentioned aryl group can be given. The aryloxy group preferably includes 6 to 20, more preferably 6 to 16, and particularly preferably 6 to 12 carbon atoms. The aryloxy group is phenyloxy, 2-naphthyloxy or the like, for example.

The arylthio group including 6 to 50 ring carbon atoms is expressed as —SY. As examples of Y, examples of the above-mentioned aryl group can be given. The arylthio group preferably includes 6 to 20, more preferably 6 to 16, and particularly preferably 6 to 12 carbon atoms. The arylthio group is phenylthio or the like, for example.

The alkoxycarbonyl group including 2 to 50 carbon atoms preferably includes 2 to 20, more preferably 2 to 16, and particularly preferably 2 to 12 carbon atoms. The alkoxycarbonyl group is methoxycarbonyl, ethoxycarbony or the like, for example.

As the amino group substituted with the substituted or unsubstituted aryl group including 6 to 50 ring carbon atoms, diarylamino, alkylarylamino and arylamino can be given. As examples of the alkyl group and the aryl group that are bonded to the nitrogen atom, the aryl group and the alkyl group mentioned above can be given. The amino group is preferably includes 6 to 20, more preferably 6 to 12, and particularly preferably 6 carbon atoms. The amino group is diphenylamino or the like, for example.

As the halogen atom, a fluorine atom, a chlorine atom and a bromine atom can be given. A fluorine atom is preferable.

The substituents of each of the above-mentioned groups are independently a linear or branched alkyl group including 1 to 20 carbon atoms, a linear or branched alkenyl group including 2 to 20 carbon atoms, a cycloalkyl group including 3 to 20 ring carbon atoms, a trialkylsilyl group including 1 to 20 carbon atoms, a silyl group having an aryl group or alkyl group including 6 to 24 ring carbon atoms, an alkylarylsilyl group having an alkyl group including 1 to 20 carbon atoms and an aryl group including 6 to 24 ring carbon atoms, an aryl group including 6 to 24 ring carbon atoms, a heteroaryl group including 5 to 24 ring atoms, an alkoxy group including 1 to 20 carbon atoms, a halogen atom or a cyano group. Specifically, the aryl group, alkyl group, cycloalkyl group, heteroaryl group, alkoxy group, halogen atom or cyano group mentioned above can be given. Further, these groups may have similar substituents.

As the alkenyl group, a substituent having an unsaturated bond within a molecule of the above-mentioned alkyl group can be mentioned.

As the silyl group having an aryl group, a triarylsilyl group, an alkylarylsilyl group and a trialkylsilyl group can be given.

As examples of preferable substituents, methyl, ethyl, propyl, isopropyl, butyl, sec-butyl, tert-butyl, cyclohexyl, phenyl, 1-naphthyl, 2-naphthyl, trimethylsilyl and triphenylsilyl can be given.

Specific examples of the compound represented by the formulas (I) and (II) will be given below. The compound represented by the formulas (I) and (II) is not restricted to the following examples.

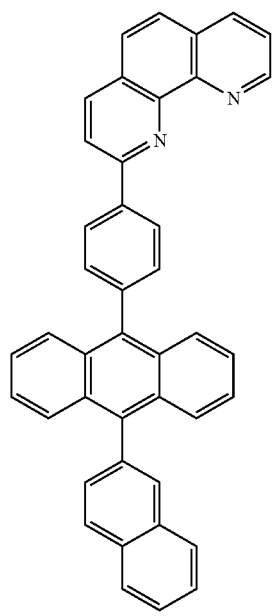 (B-1)
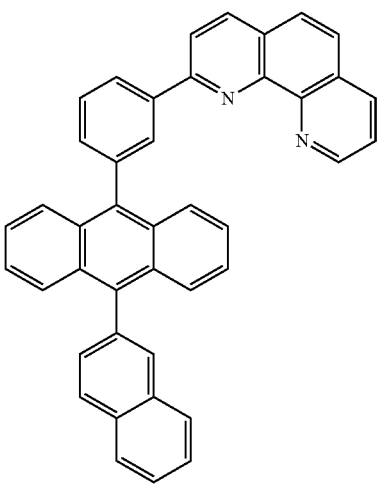 (B-2)
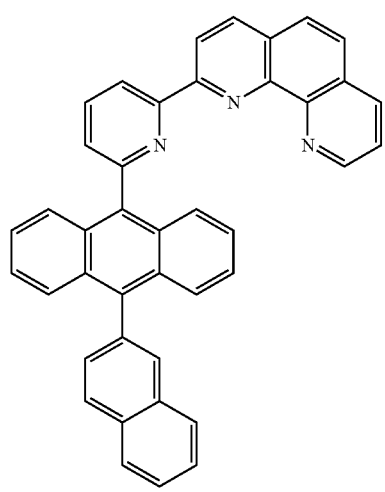 (B-3)
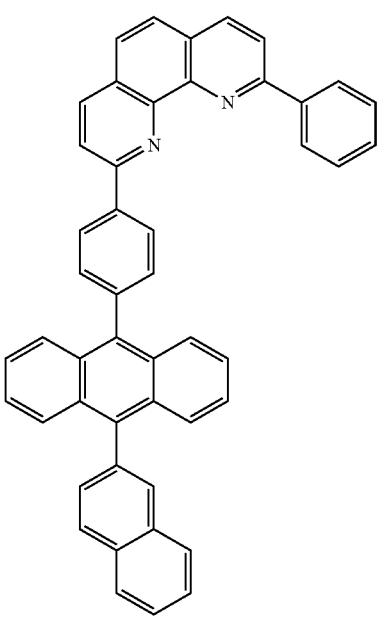 (B-4)

-continued
(B-5)
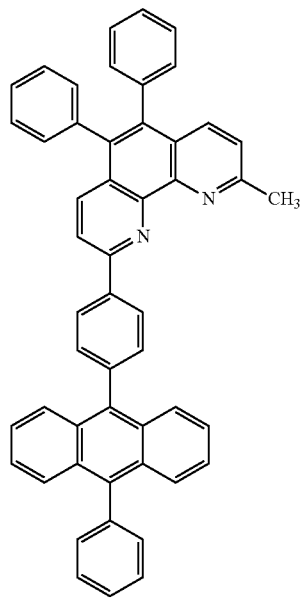
(B-6)
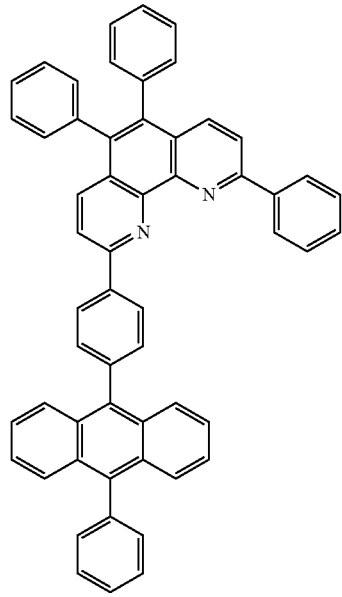
(B-7)
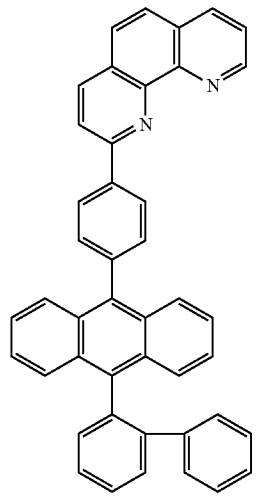
(B-8)
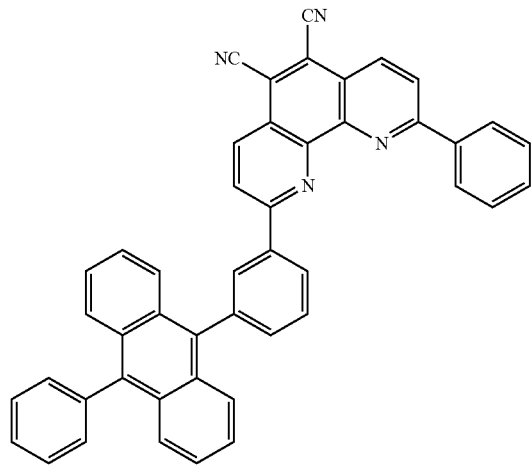
(B-9)
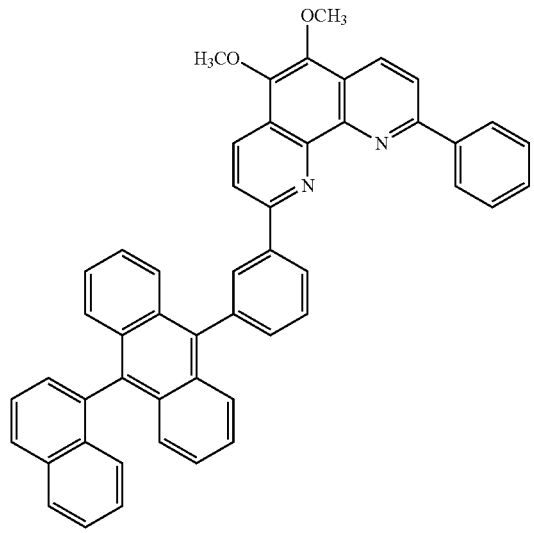
(B-10)

-continued
(B-11)
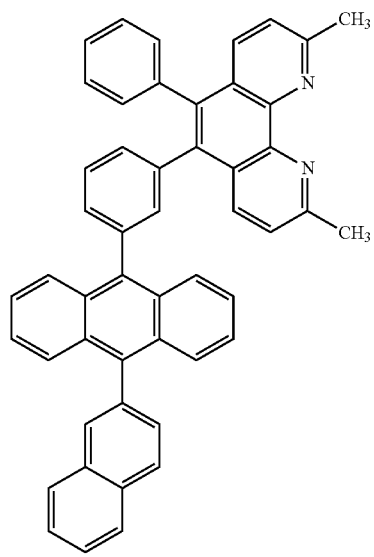
(B-12)
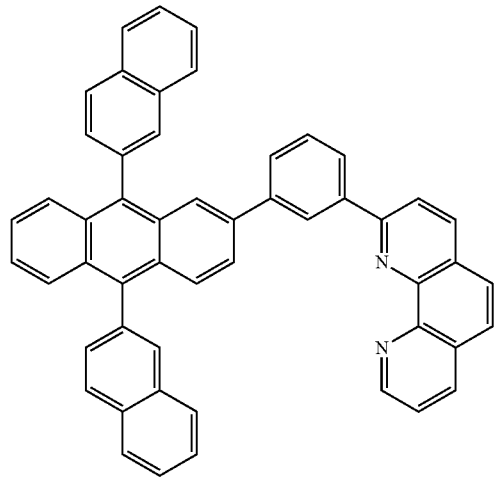
(B-13)
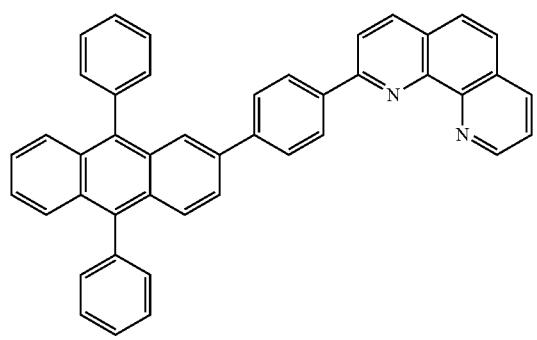
(B-14)
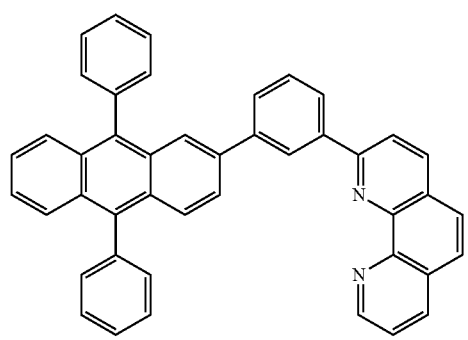
(B-15)
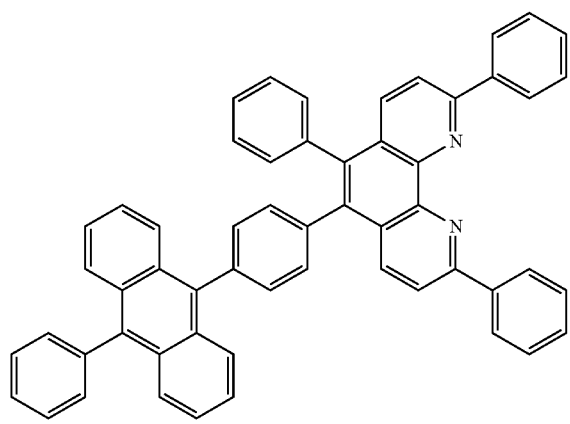
(B-16)
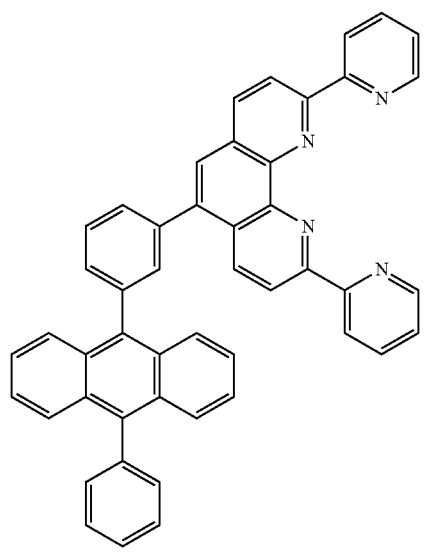

(B-17)
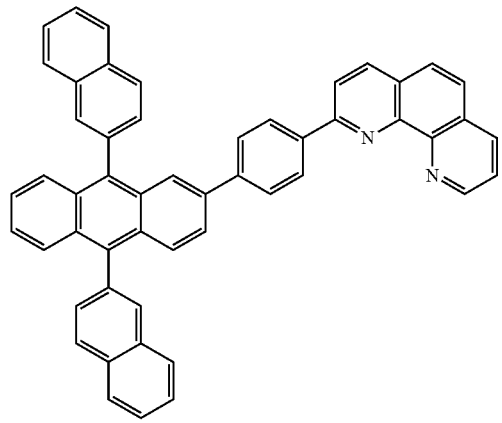
(B-18)
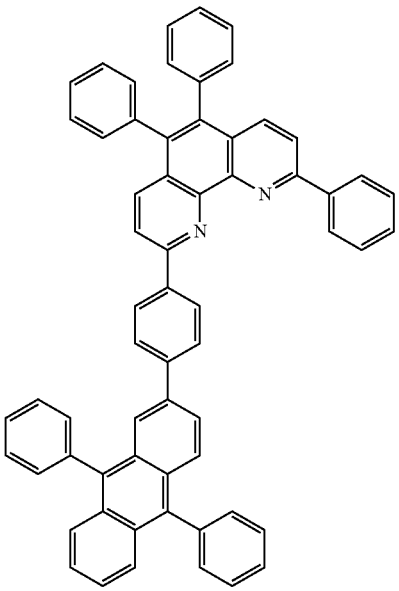
(B-19)
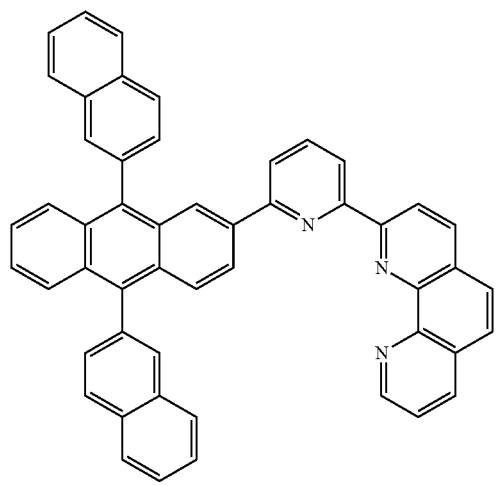
(B-20)
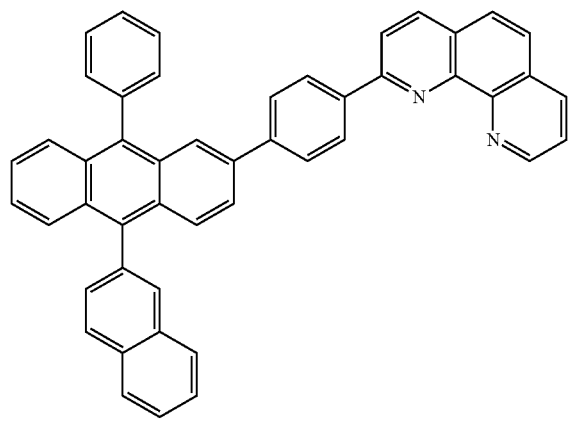
(B-21)
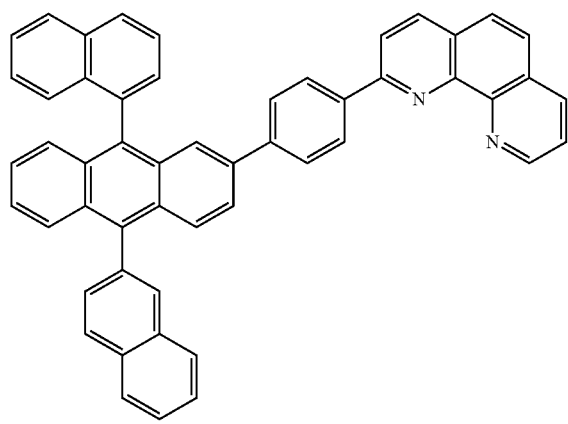
(B-22)
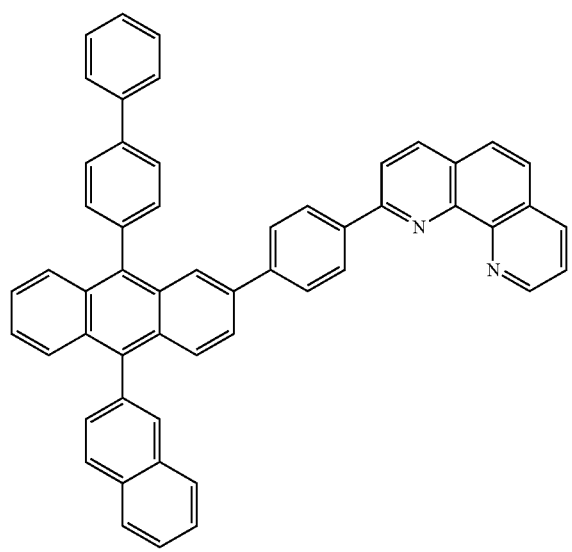

-continued
(B-23)
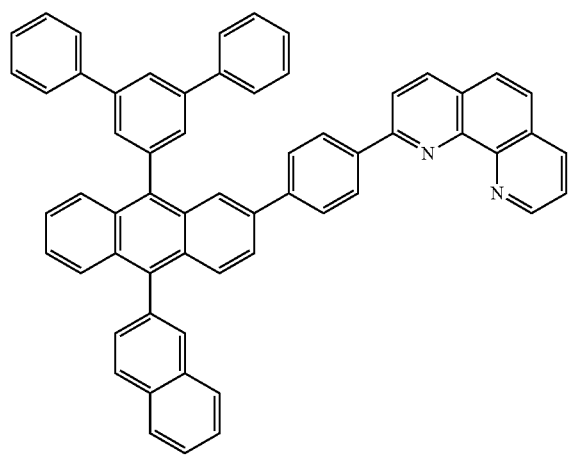
(B-24)
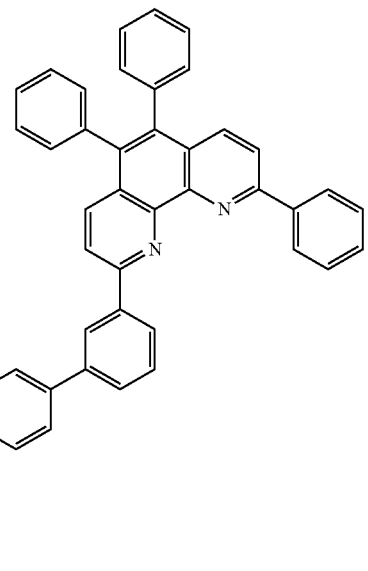
(B-25)
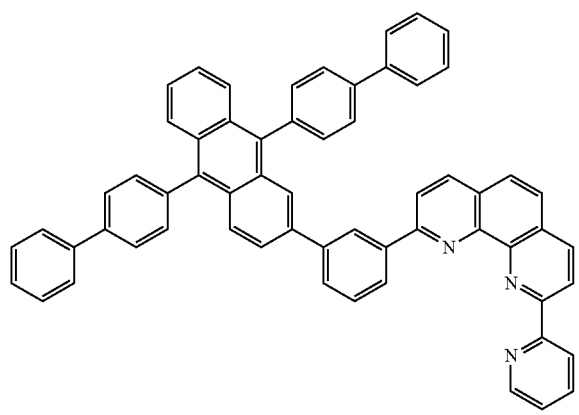
(B-26)
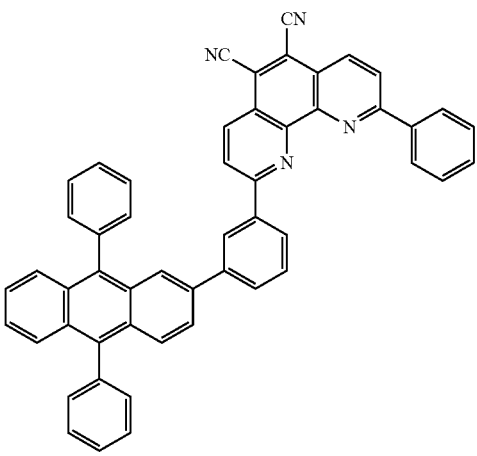
(B-27)
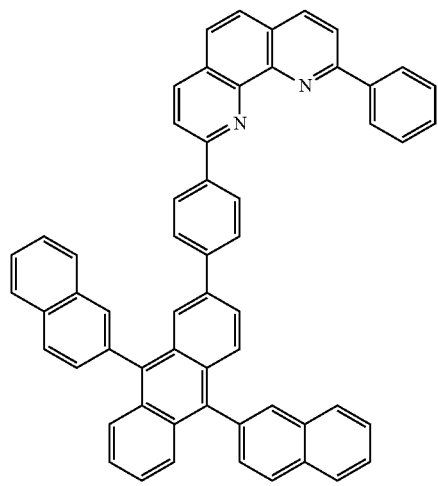
(B-28)
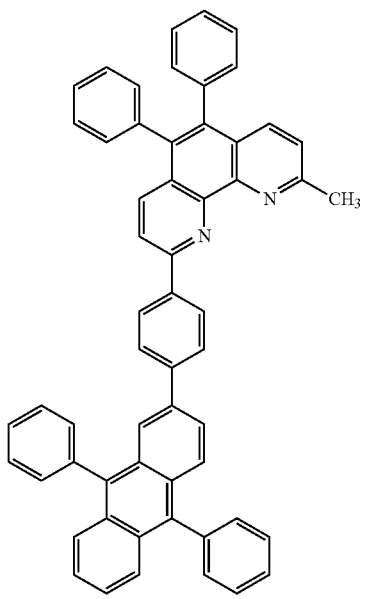

-continued
(B-29)
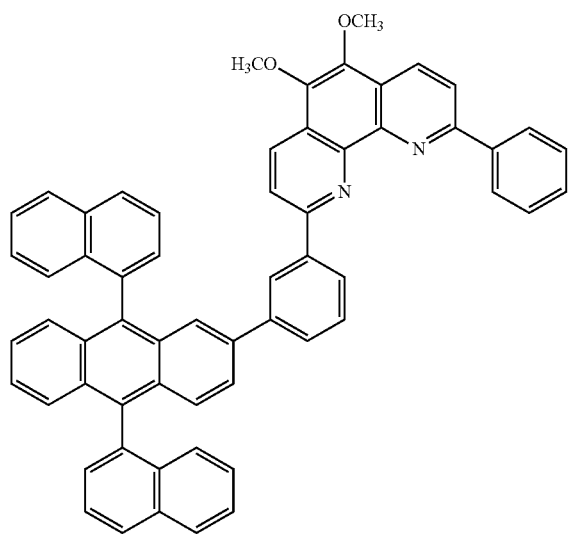
(B-30)
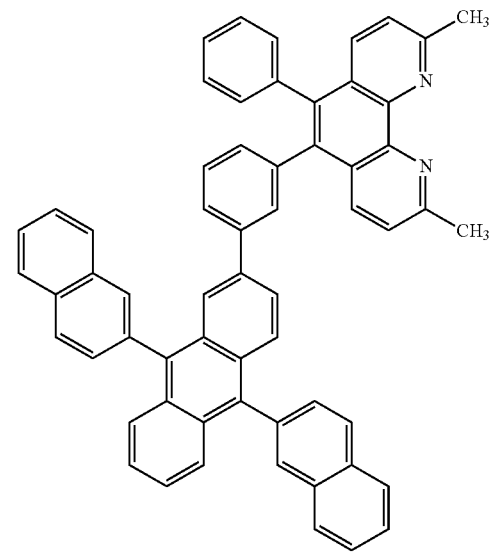
(B-31)
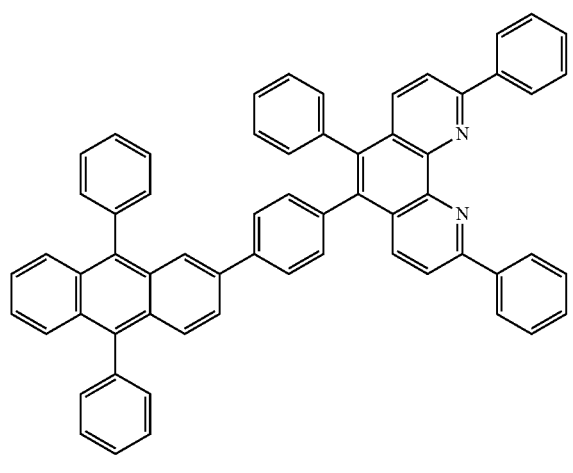
(B-32)
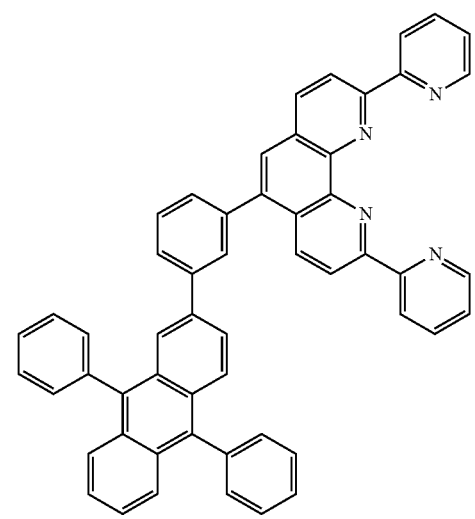
(B-33)
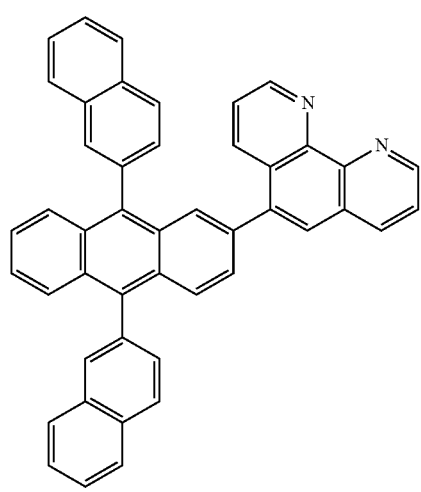
(B-34)
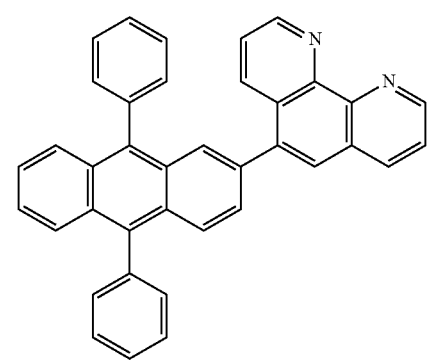

-continued
(B-35)
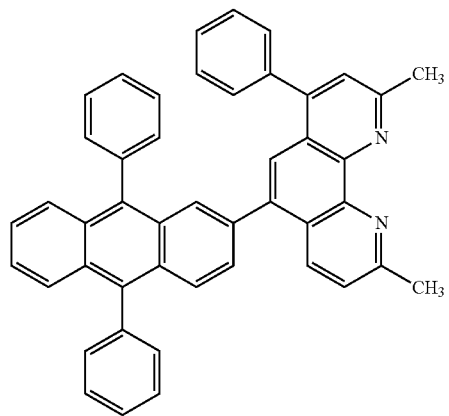
(B-36)
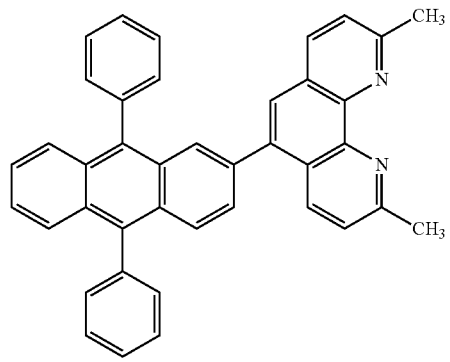
(B-37)
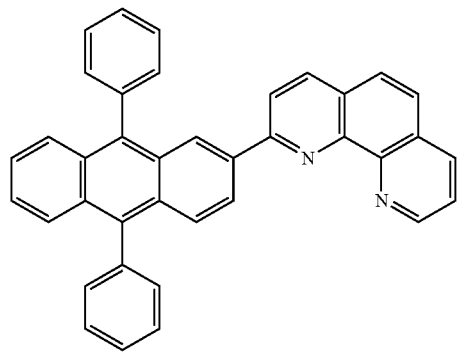
(B-38)
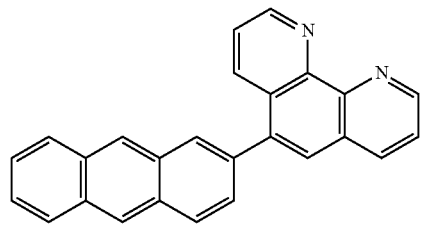
(B-39)
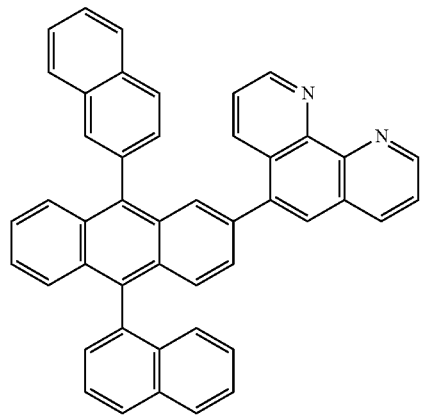
(B-40)
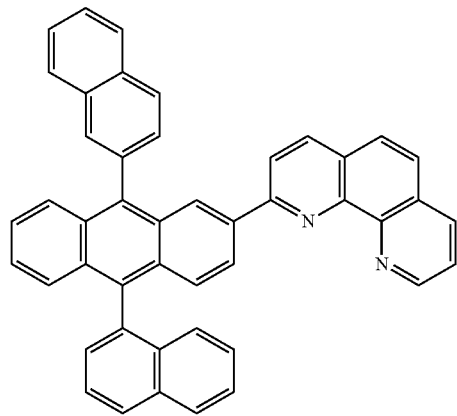
(B-41)
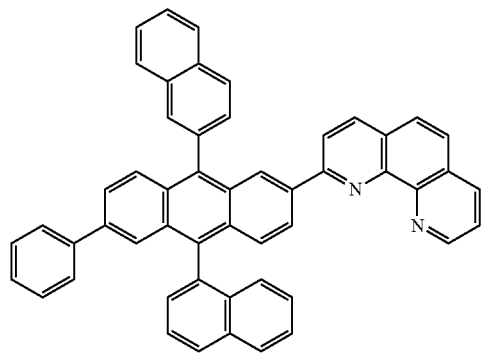
(B-42)
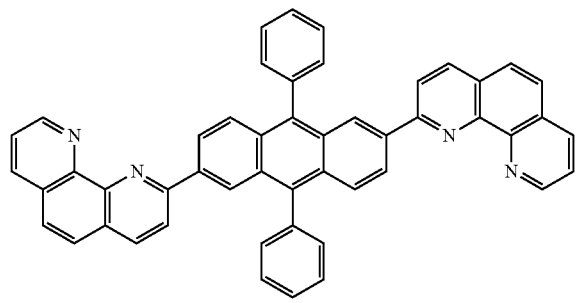

-continued
(B-43)
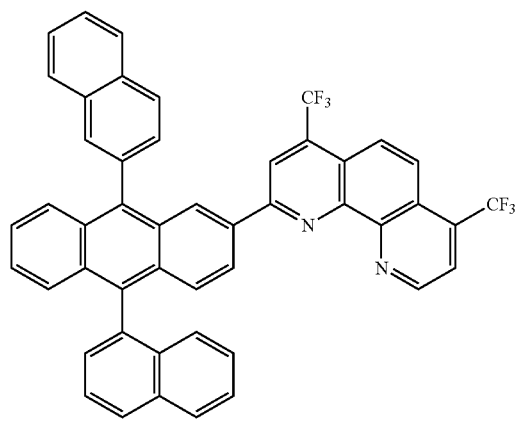
(B-44)
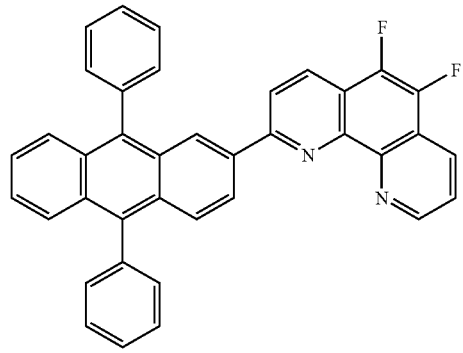
(B-45)
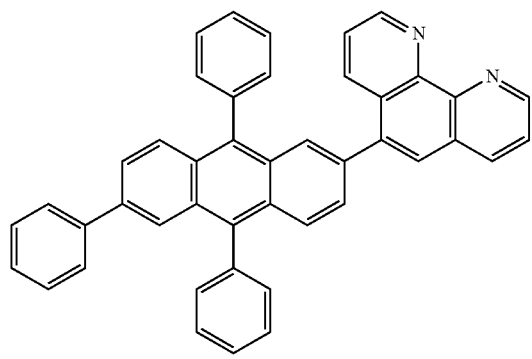
(B-46)
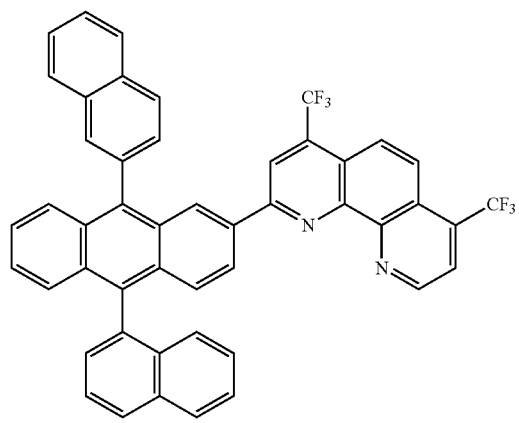
(B-47)
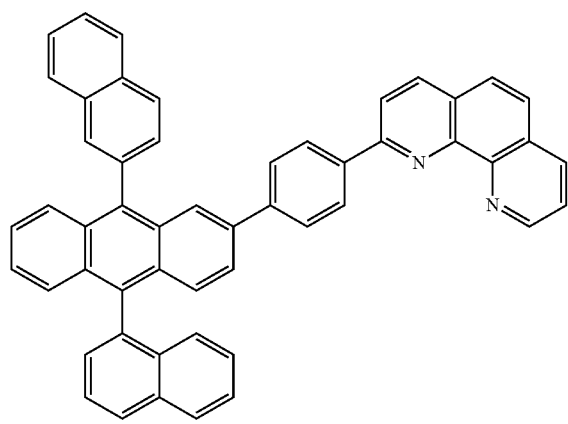
(B-48)
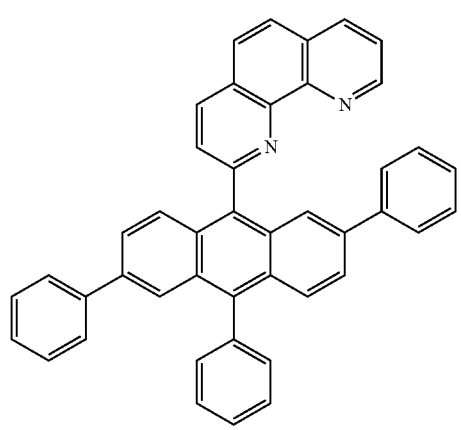

-continued
(B-49)
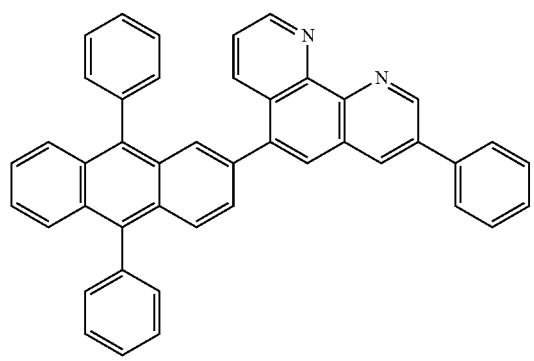
(B-50)
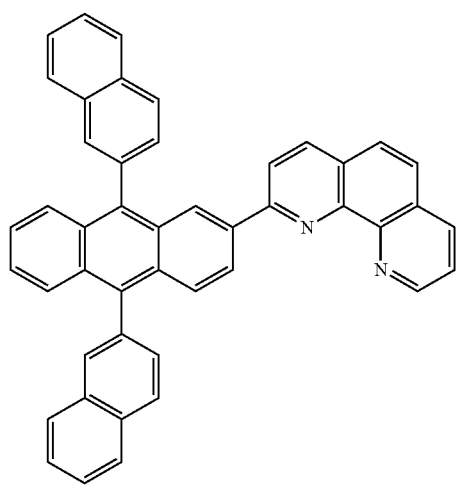
(B-51)
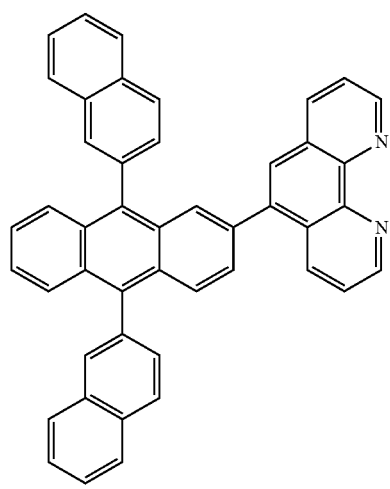
(B-52)
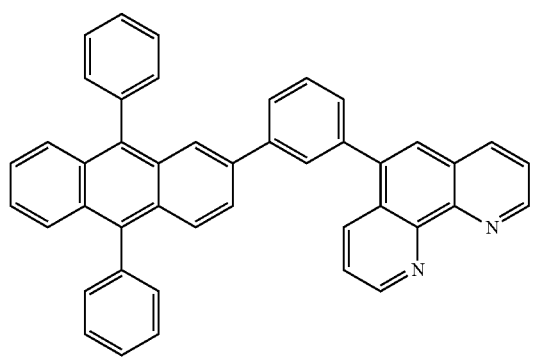
(B-53)
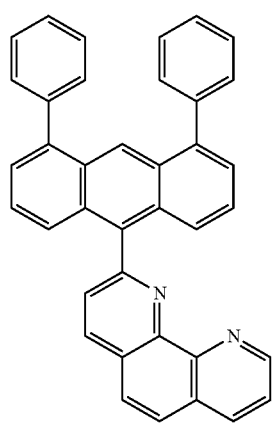
(B-54)
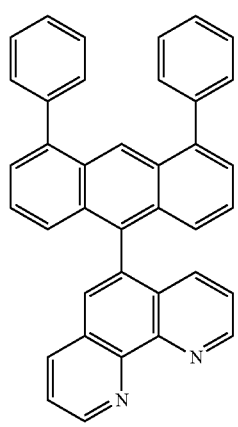

(B-55)
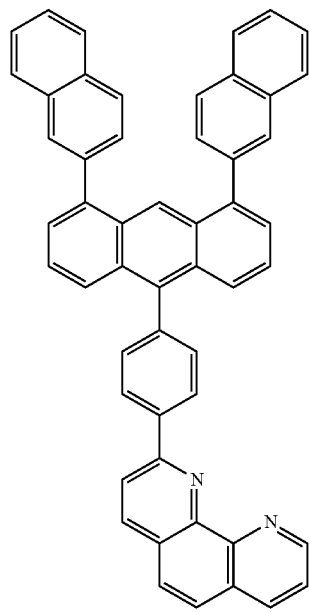
(B-56)
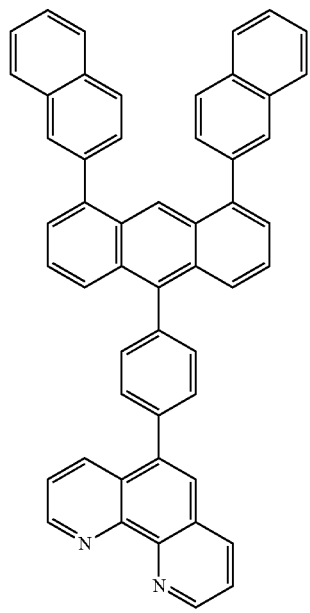
(B-57)
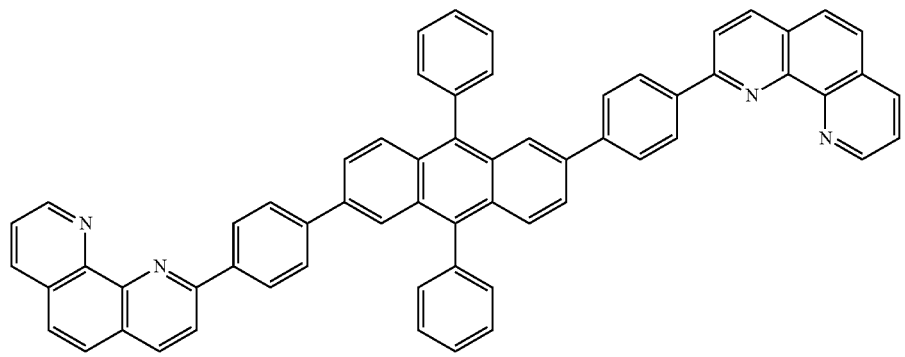
(B-58)
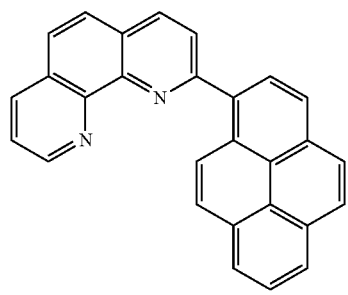
(B-59)
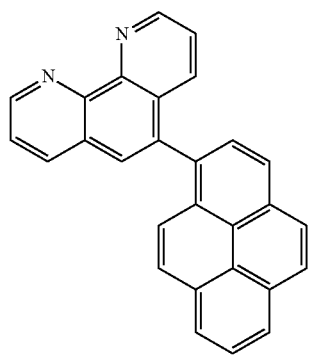

-continued
(B-60)
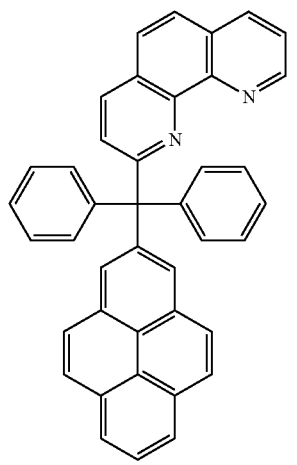
(B-61)
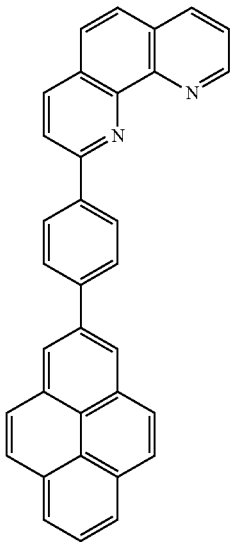
(B-62)
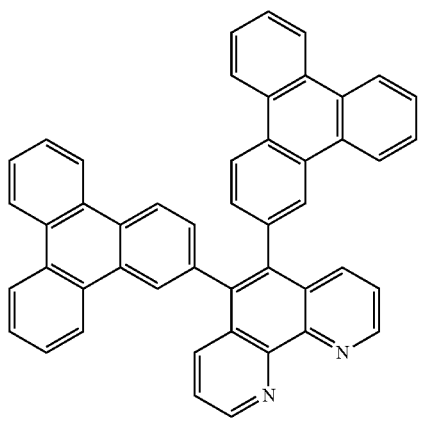
(B-63)
(B-64)
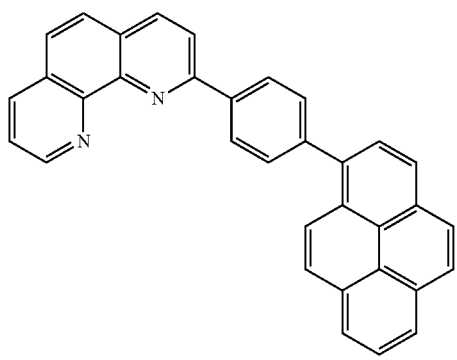
(B-65)
(B-66)
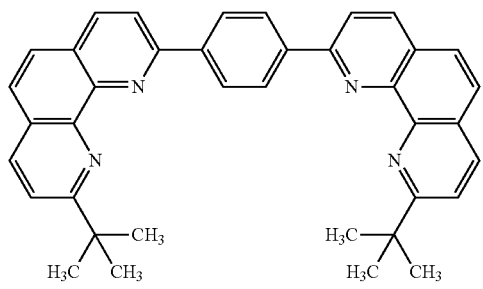
(B-67)
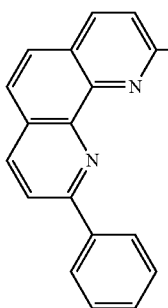

-continued
(B-68) 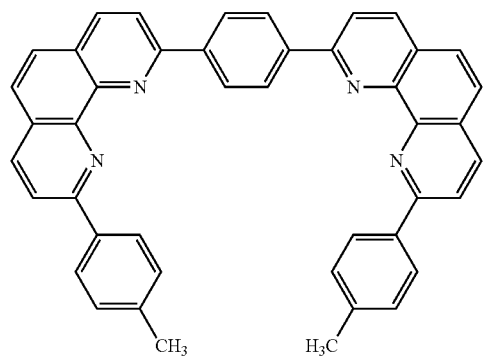
(B-69) 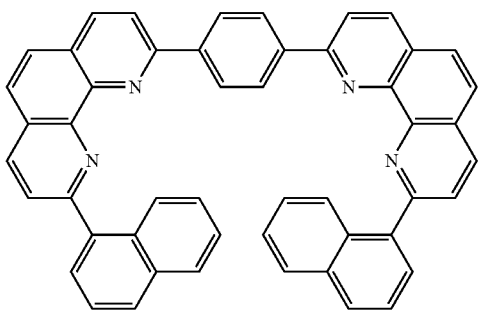
(B-70) 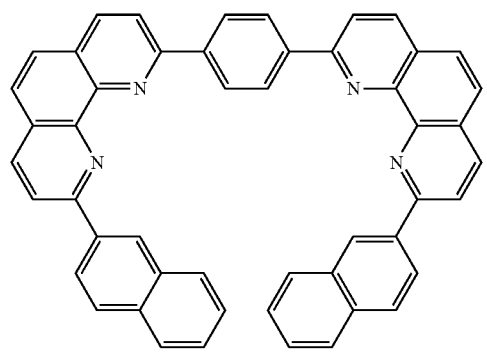
(B-71) 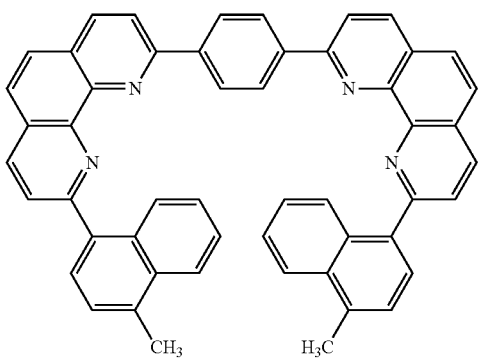
(B-72) 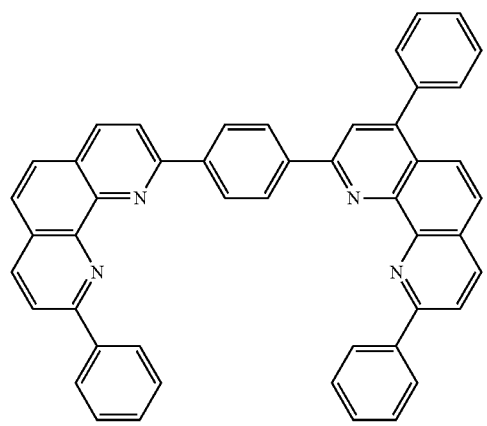
(B-73) 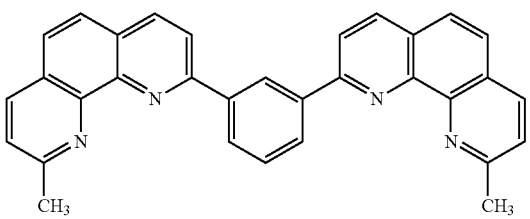
(B-74) 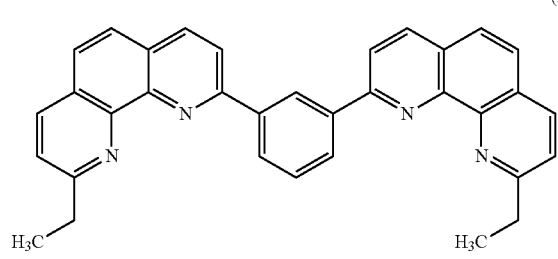
(B-75) 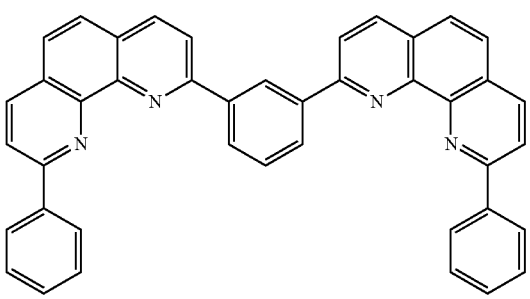

-continued
(B-76) 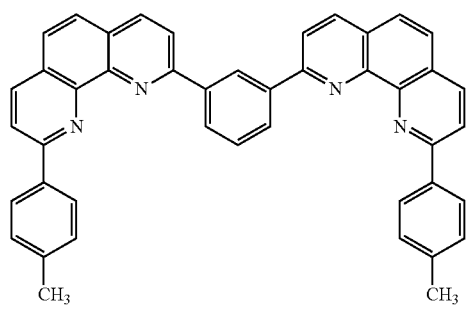
(B-77) 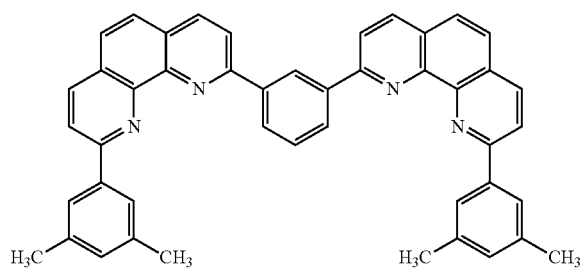
(B-78) 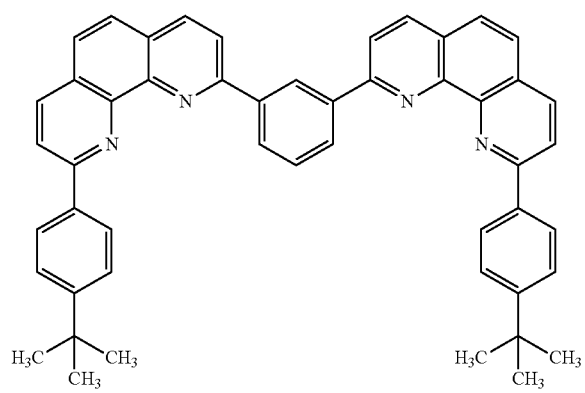
(B-79) 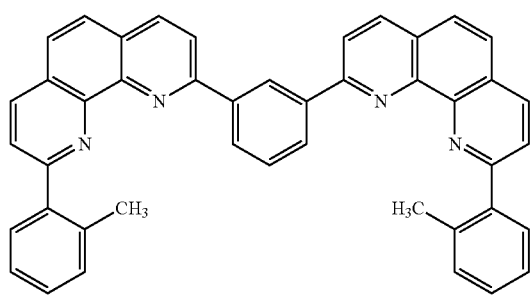
(B-80) 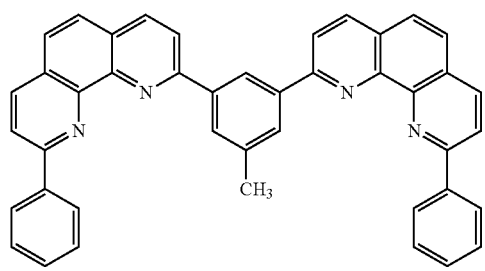
(B-81) 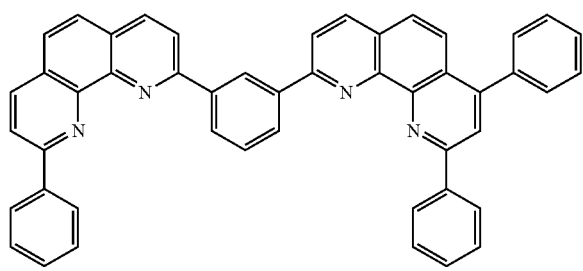
(B-82) 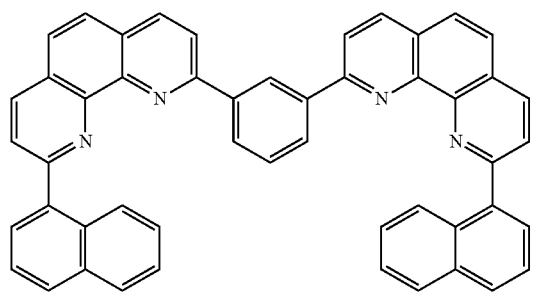
(B-83) 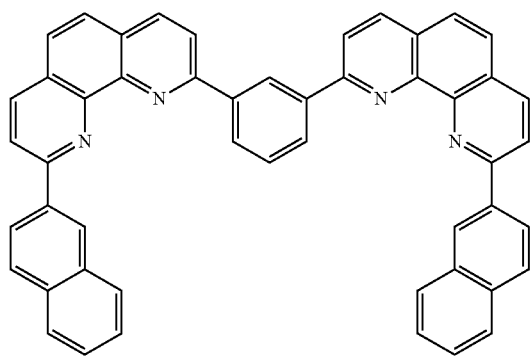

-continued
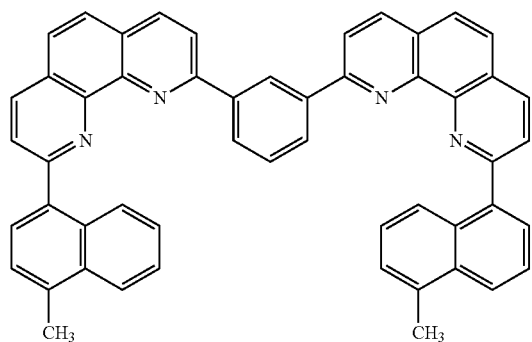
(B-84)
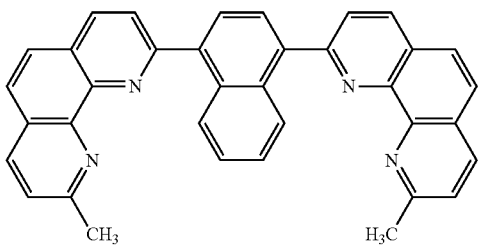
(B-85)
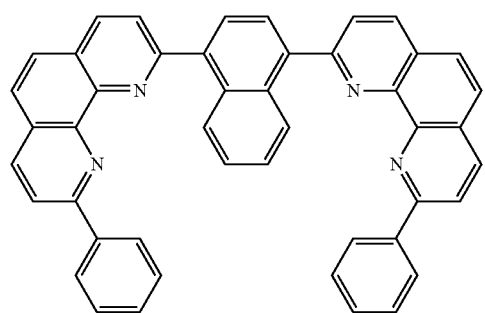
(B-86)
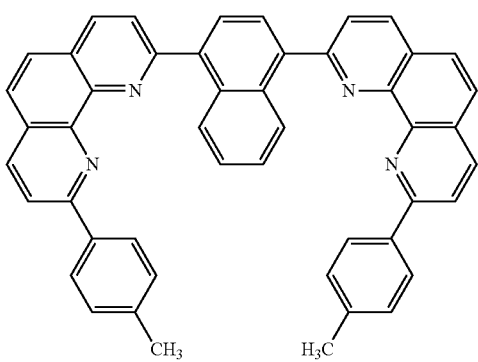
(B-87)
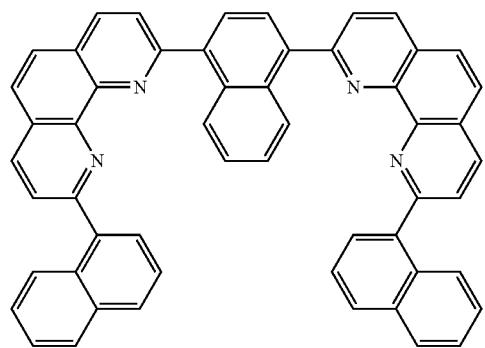
(B-88)
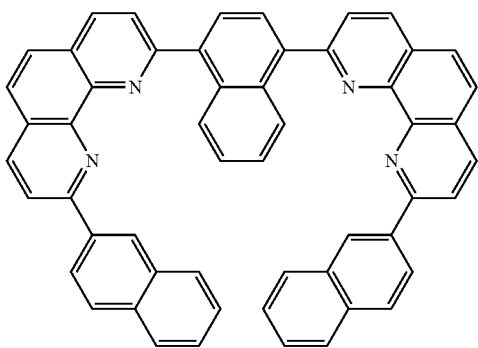
(B-89)
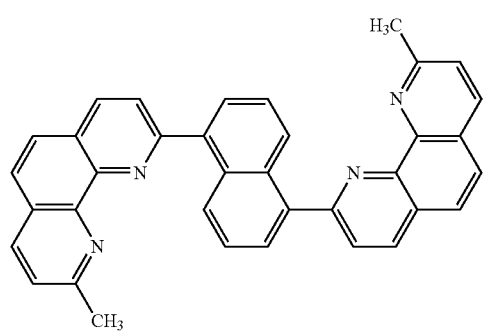
(B-90)
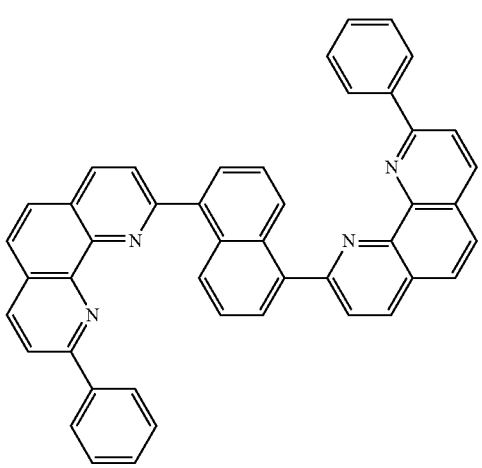
(B-91)

-continued
(B-92)
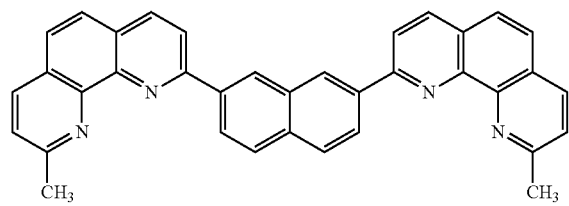
(B-93)
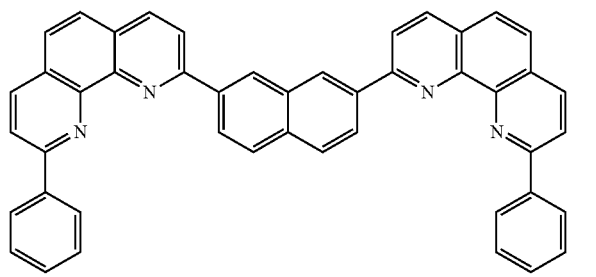
(B-94)
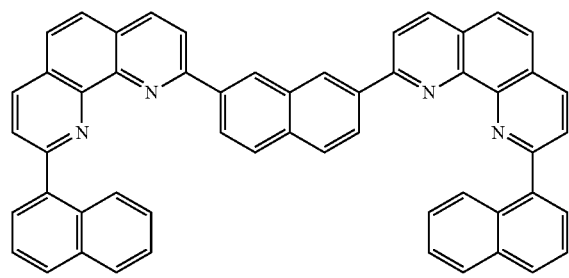
(B-96)
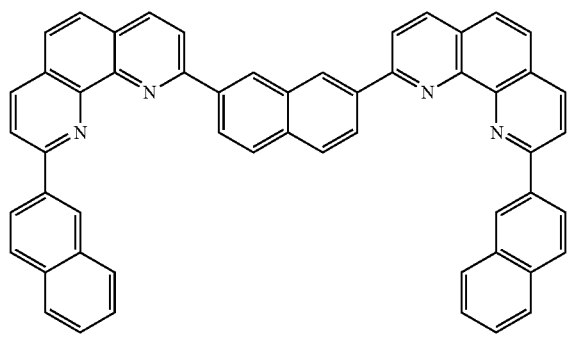
(B-97)
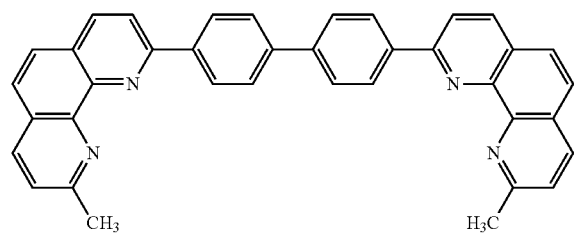
(B-98)
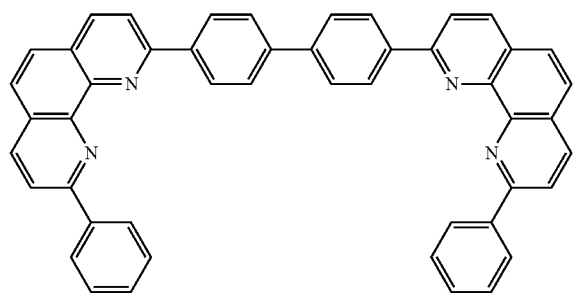
(B-99)
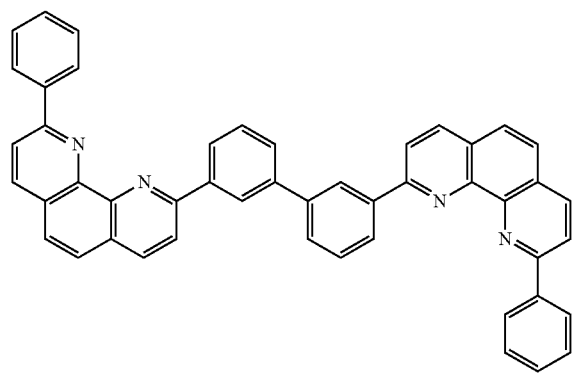
(B-100)
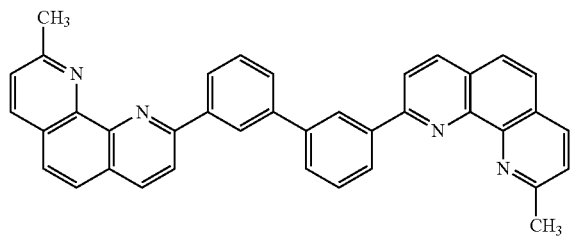

-continued

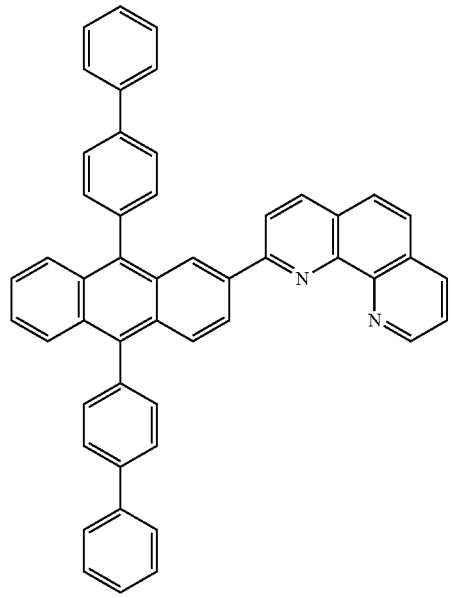
(B-101)

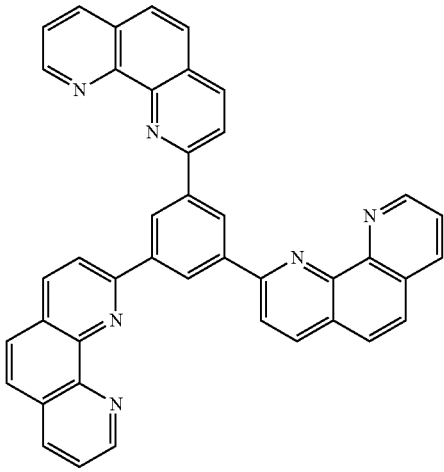
(B-102)

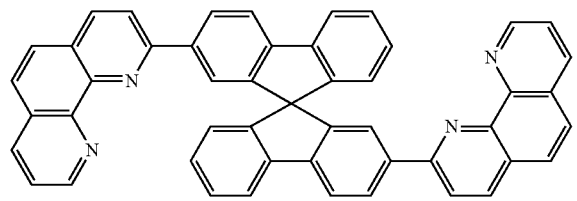
(B-103)

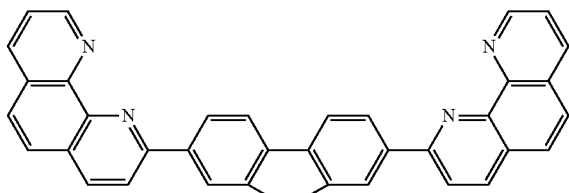
(B-104)

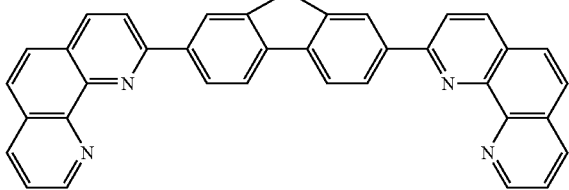

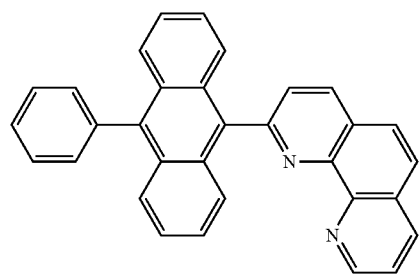
(B-105)

As for the synthesis of the compound represented by the formulas (I) and (II), reference can be made to WO2007/018004, WO2006/64484 and WO2006/021982.

In the invention, it is preferred that the N layer of the charge-generating layer contain at least one of an electron-donating metal, an electron-donating metal compound and an electron-donating metal complex in addition to the above-mentioned compound represented by the formula (I) or (II).

Specifically, it is preferred that the N layer contain at least one selected from an alkali metal, an alkali metal compound, an organic metal complex containing an alkali metal, an alkaline earth metal, an alkaline earth metal compound, an organic metal complex containing an alkaline earth metal, a rare earth metal, a rare earth metal compound and an organic metal complex containing a rare earth metal. Among these, it is preferred that the N layer contain at least one of an alkali metal, an alkaline earth metal, a simple substance of a rare earth metal, a compound of a rare earth metal and a complex of a rare earth metal.

As the alkali metal, lithium (Li), sodium (Na), potassium (K), rubidium (Rb), cesium (Cs) and the like can be given. One having a work function of 2.9 eV or less is particularly preferable. Among them, Li, K, Rb and Cs are preferable. Li, Rb or Cs is further preferable. Li is most preferable.

As the alkaline-earth metal, calcium (Ca), magnesium (Mg), strontium (Sr), barium (Ba) and the like can be given. One having a work function of 2.9 eV or less is particularly preferable.

As the rare-earth metal, scandium (Sc), yttrium (Y), cerium (Ce), terbium (Tb), ytterbium (Yb) and the like can be given. One having a work function of 2.9 eV or less is particularly preferable.

Among the above-mentioned metals, preferable metals have a particularly high reducing ability, and hence enable the resulting organic EL device to have an excellent luminance and a prolonged life by adding a relative small amount to an electron-injecting region.

Examples of the alkali metal compound include an alkali oxide such as lithium oxide ($Li_2O$), cesium oxide ($Cs_2O$) or potassium oxide ($K_2O$), and an alkali halide such as lithium fluoride (LiF), sodium fluoride (NaF), cesium fluoride (CsF) or potassium fluoride (KF). Among them, lithium fluoride (LiF), lithium oxide ($Li_2O$) and sodium fluoride (NaF) are preferable.

Examples of the alkaline-earth metal compound include barium oxide (BaO), strontium oxide (SrO), calcium oxide (CaO), and mixtures thereof such as barium strontium acid ($Ba_xSr_{1-x}O$) ($0<x<1$) and barium calcium acid ($Ba_xCa_{1-x}O$) ($0<x<1$). Among them, BaO, SrO and CaO are preferred.

Examples of the rare-earth metal compound include ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$). Among these, $YbF_3$, $ScF_3$ and $TbF_3$ are preferable.

The organic metal complexes are not particularly limited as long as they contain, as a metal ion, at least one of alkali metal ions, alkaline-earth metal ions, and rare-earth metal ions, as mentioned above. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluoboran, bipyridyl, phenanthroline, phthalocyanine, porphyrin, cyclopentadiene, β-diketones, azomethines, and derivatives thereof.

Regarding the addition form of the metal, the compound and the complex as mentioned above, it is preferred that the metal, the compound and the complex be formed in the shape of a layer or an island in the interfacial region. A preferred method for the formation is a method in which an organic substance as a light emitting material or an electron-injecting material for forming the interfacial region is deposited simultaneously with the deposition of at least one of the metal, the compound and the complex by a resistant heating deposition method, thereby dispersing at least one of the metal, the compound and the complex in the organic substance. The dispersion concentration of the organic substance to the metal, the compound and the complex as mentioned above in terms of thickness ratio is normally 1000:1 to 1:1000, preferably 100:1 to 1:1.

In the case where at least one of the metal, the compound and the complex is formed into the shape of a layer, the light-emitting material or electron-injecting material which serves as an organic layer in the interface is formed into the shape of a layer. After that, at least one of the metal, the compound and the complex is solely deposited by the resistant heating deposition method to form a layer preferably having a thickness of 0.1 nm or more and 15 nm or less.

In the case where at least one of the metal, the compound and the complex is formed into the shape of an island, the light emitting material or the electron-injecting material which serves as an organic layer in the interface is formed into the shape of an island. After that, at least one of the metal, the compound and the complex is solely deposited by the resistant heating deposition method to form an island preferably having a thickness of 0.05 nm or more and 1 nm or less.

In addition, the ratio of the main component to at least one of the metal, the compound and the complex mentioned above in the organic EL device of the invention is preferably the main component: electron-donating dopant and/or the organic metal complex=100:1 to 1:1 in terms of film thickness ratio, with 50:1 to 4:1 being further preferable.

It suffices that the organic EL device of the invention contain the compound represented by the above formula (I) or (II) in the N layer of the charge-generating layer. As for the anode, the emitting unit, the cathode or the like, as the other constituting materials, a material known in this technical field can be appropriately used.

Hereinbelow, each element constituting the organic EL device of the invention will be explained.

(Substrate)

The organic EL device of the invention is formed on a substrate. The substrate serves to support the organic EL device. If emission from the emitting unit is outcoupled through the substrate, the substrate is required to be transparent. In this case, the substrate preferably has a transmittance of 50% or more for light rays within visible ranges of 400 to 700 nm.

Specific examples thereof include glass plates and polymer plates. Examples of the glass plate include soda-lime glass, barium/strontium-containing glass, lead glass, aluminosilicate glass, borosilicate glass, barium borosilicate glass, and quartz. Examples of the polymer plate include polycarbonate, acrylic polymer, polyethylene terephthalate, polyethersulfide, and polysulfone.

Transparency is not required when the supporting substrate is positioned in the direction opposite to the light-outcoupling direction.

(Anode)

The anode of the organic EL device plays a role for injecting holes into the hole-transporting layer or the emitting layer. When transparency is required for the anode, indium tin oxide alloy (ITO), tin oxide (NESA), indium zinc oxide alloy (IZO), gold, silver, platinum, copper, and the like may be used as the material for the anode. When the anode is a reflective electrode which does not require transparency, a metal such as silver, aluminum, molybdenum, chromium, and nickel or alloys thereof with other metals can also be used.

In particular, when an anode having a small work function (for example, 5.0 eV or less) is used in combination with the hole-injecting layer using the material for an organic EL device of the invention, donating and receiving electrons are possible, whereby excellent injection properties are exhibited.

Although these materials may be used individually, alloys thereof or materials wherein another element is added to the materials can be appropriately selected for use.

The anode can be formed by forming these electrode materials into a thin film by vapor deposition, sputtering or the like. In the case where emission from the emitting layer is outcoupled through the anode, the transmittance of the anode for the emission is preferably more than 10%. The sheet resistance of the anode is preferably several hundred Ω/□ or less. The film thickness of the anode, which varies depending upon the material thereof, is usually from 10 nm to 1 µm, preferably from 10 to 200 nm.

(Emitting Unit)

The emitting unit has a single layer or a stacked layer structure that at least comprises an emitting layer. The emitting unit is preferably of a multilayer structure in which a first organic layer, an emitting layer and a second organic layer are provided from the anode. Specifically, a multilayer structure comprising a hole-transporting region/emitting layer/electron-transporting region can be mentioned.

The hole-transporting region is formed of a single layer of a hole-injecting layer or a hole-transporting layer, or a stacked structure formed by stacking a plurality of these layers.

The organic EL device of the invention has two or more emitting units. Emitting units may be formed of the same material or may be formed of different materials.

The layer structure of the emitting units may be the same or different. For example, in the organic EL device shown in FIG. 1, the electron-transporting layer of the first emitting unit 30A can be omitted, and the emitting unit may be of a two-layer structure of the hole-transporting layer 31A and the emitting layer 32A.

The emission colors of the emitting units may be the same or different. For example, in the device 1 shown in FIG. 1, the emission color of the first emitting unit 30A is allowed to be yellow, and the emission color of the second emitting unit 30B to be blue. In this case, a white emitting organic EL device can be obtained by mixing these two colors.

Hereinbelow, an explanation will be made on the emitting layer, the hole-transporting region and the electron-transporting region constituting the emitting unit.

(A) Emitting Layer

As the emitting layer, a layer formed of a host material and a dopant material is preferable.

As the host material of the organic EL device, rubrene, anthracene, tetracene, pyrene, perylene or the like can be used. It is further preferred that the host material of the organic EL device of the invention comprise an anthracene derivative, more preferably an anthracene derivative represented by the following formula (1):

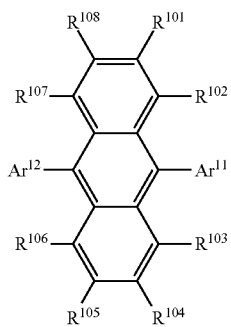

wherein $Ar_{11}$ and $Ar_{12}$ are independently a substituted or unsubstituted aryl group including 6 to 30 ring carbon atoms or a substituted or unsubstituted heterocyclic group including 5 to 30 ring atoms; and $R_{101}$ to $R_{108}$ are independently a halogen atom, a fluorine atom, a substituted or unsubstituted alkyl group including 1 to 10 carbon atoms, a substituted or unsubstituted cycloalkyl group including 3 to 10 carbon atoms, a substituted or unsubstituted alkylsilyl group including 3 to 30 carbon atoms, a substituted or unsubstituted arylsilyl group including 8 to 30 ring carbon atoms, a substituted or unsubstituted alkoxy group including 1 to 20 carbon atoms, a substituted or unsubstituted aryloxy group including 6 to 20 ring carbon atoms, a substituted or unsubstituted aryl group including 6 to 30 ring carbon atoms, or a substituted or unsubstituted heterocyclic group including 5 to 30 ring atoms.

As the emitting dopant, a fluorescent dopant and a phosphorescent dopant can be given.

A fluorescent dopant is a compound that can emit light from a singlet exciton. A fluorescent dopant is preferably a compound selected from an amine-based compound, an aromatic compound, a chelate complex such as tris(8-quinolinolato)aluminum complex, a coumarin derivative, a tetraphenylbutadiene derivative, a bistyrylarylene derivative and an oxadiazole derivative according to the required emission color. A styrylamine compound, a styryldiamine compound, an arylamine compound, an aryldiamine compound and an aromatic compound are more preferable, with a fused polycyclic amine derivative and an aromatic compound being further preferable. These fluorescent dopants may be used singly or in combination of two or more.

As the fused polycyclic amine derivative, one represented by the following formula (2) is preferable.

In the formula, Y is a substituted or unsubstituted fused aryl group including 10 to 50 ring carbon atoms.

$Ar_{21}$ and $Ar_{22}$ are independently a substituted or unsubstituted aryl group including 6 to 50 ring carbon atoms or a substituted or unsubstituted heterocyclic group including 5 to 50 ring atoms.

The fused aryl group is a group in which two or more ring structures are fused among the above-mentioned aryl group.

As the fused aryl group, a fused aryl group including 10 to 50 (preferably 10 to 30, more preferably 10 to 20) ring carbon atoms can be given. Among the above-mentioned specific examples of the aryl group, a naphthyl group, an anthryl group, a pyrenyl group, a chrysenyl group, a phenanthryl group, a fluorenyl group, a fluoranthenyl group, an acenaphthofluoranthenyl group, a naphthacenyl group or the like can preferably be given.

Specific examples of Y include the above-mentioned fused aryl group. Y is preferably a substituted or unsubstituted anthryl group, a substituted or unsubstituted pyrenyl group, a substituted or unsubstituted chrysenyl group, and an acenaphthofluoranthenyl group.

Preferable examples of $Ar_{21}$ and $Ar_{22}$ include a substituted or unsubstituted phenyl group and a substituted or unsubstituted dibenzofuranyl group. Preferable examples of substituents for $Ar_{21}$ and $Ar_{22}$ include an alkyl group, a cyano group and a substituted or unsubstituted silyl group. n is an integer of 1 to 4, preferably an integer of 1 or 2.

As the aromatic compound, a fluoranthene compound represented by the following formula (3) is preferable.

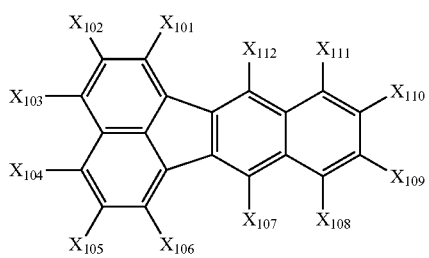

(3)

In the formula, $X_{101}$ to $X_{106}$ and $X_{108}$ to $X_{111}$ are independently selected from a hydrogen atom, a substituted or unsubstituted aryl group including 6 to 30 ring carbon atoms, a substituted or unsubstituted heterocyclic group including 5 to 30 ring atoms, a substituted or unsubstituted alkyl group including 1 to 10 carbon atoms, a substituted or unsubstituted cycloalkyl group including 3 to 8 ring carbon atoms, a substituted or unsubstituted alkoxy group including 1 to 20 carbon atoms, a substituted or unsubstituted aralkyl group including 7 to 50 carbon atoms, a substituted or unsubstituted aryloxy group including 6 to 50 ring atoms, a substituted or unsubstituted arylthio group including 5 to 50 ring atoms, a substituted or unsubstituted alkoxycarbonyl group including 2 to 50 carbon atoms, an amino group substituted with a substituted or unsubstituted aryl group including 6 to 30 ring carbon atoms, a halogen atom, a cyano group, a nitro group, a hydroxyl group and a carboxyl group.

$X_{107}$ and $X_{112}$ are independently selected from a substituted or unsubstituted aryl group including 6 to 30 ring carbon atoms, a substituted or unsubstituted heterocyclic group including 5 to 30 ring atoms, a substituted or unsubstituted alkyl group including 1 to 20 carbon atoms, and a substituted or unsubstituted cycloalkyl group including 3 to 8 ring carbon atoms.

However, $X_{103}$ and $X_{104}$ are substituents different from each other.

In $X_{101}$ to $X_{112}$, adjacent substituents may be bonded each other to form a saturated or unsaturated ring structure, and these ring structures may be substituted.

$X_{103}$ or $X_{104}$ of the formula (3) is preferably a substituted or unsubstituted aryl group including 6 to 30 ring carbon atoms. The preferred substituent of the "substituted or unsubstituted" of the formula (3) is a cyano group or a halogen atom.

In the formula (3), as examples of the aryl group, the heterocyclic group, the alkyl group, the cycloalkyl group, the alkoxy group, the aralkyl group, the aryloxy group, the arylthio group, the alkoxycarbonyl group and the halogen atom, those exemplified above can be mentioned.

A host suitable for phosphorescence emission is a compound having a function of allowing a phosphorescent compound to emit light as a result of energy transfer to a phosphorescent compound from its excited state. No specific restrictions are imposed on the host compound as long as it has a large triplet energy gap and is capable of transferring exciton energy to a phosphorescent compound, and can be selected appropriately depending on the intended use.

Specific examples of the host compound include a fused ring compound formed of a combination of a benzene ring, a naphthalene ring or a heterocyclic ring, a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene compound, a porphyrin-based compound, an anthraquinodimethane derivative, an anthrone derivative, a diphenylquinone derivative, a thiopyranedioxide derivative, a carbodimide derivative, a fluorenylidenemethane derivative, a distyrylpyrazine derivative, and a heterocyclic tetracarboxylic acid anhydride such as a naphthaleneperylene; various metal complexes represented by metal complexes of a phthalocyanine derivative and a 8-quinolinol derivative, metal phthalocyanine and metal complexes including benzoxazole or benzothiazole as a ligand; conductive high-molecular oligomer such as a polysilane-based compound, a poly(N-vinylcarbazole)derivative, an aniline-based copolymer, a thiophene oligomer and polythiophene; and a high-molecular compound such as a polythiophene derivative, a polyphenylene derivative, a polyphenylenevinylene derivative, and a polyfluorene derivative can be given. These host compounds may be used singly or in combination of two or more.

Specific examples include the following compounds.

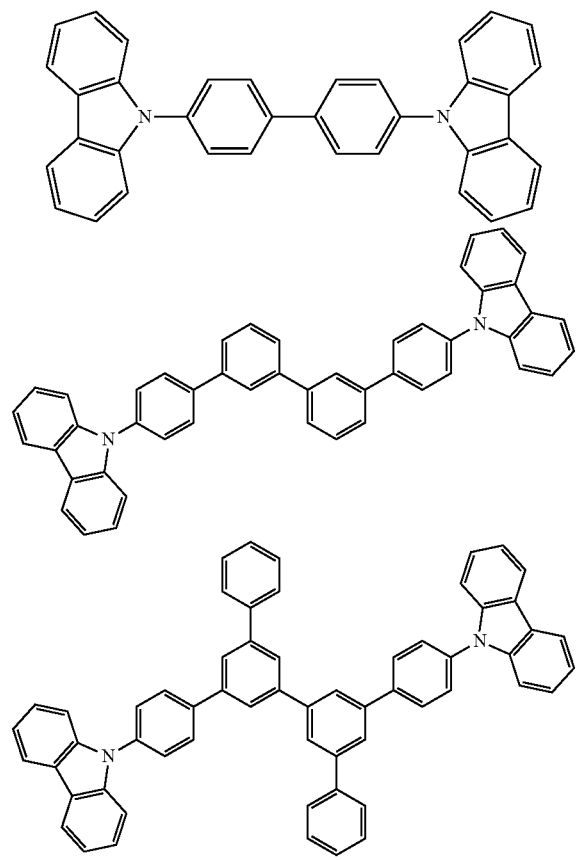

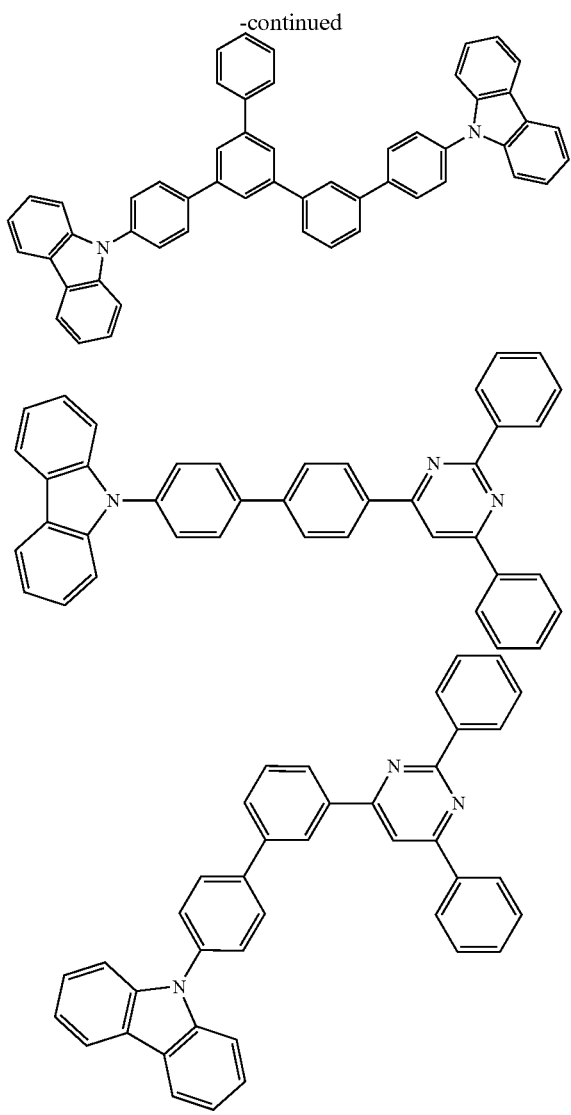

A phosphorescent dopant is a compound that can emit light from triplet excitons. The type of the phosphorescent dopant is not limited as long as it can emit from triplet excitons. A phosphorescent dopant is preferably a metal complex containing at least one metal selected from Ir, Ru, Pd, Pt, Os and Re. A porphyrin metal complex or an ortho-metalated complex is preferable. As the porphyrin metal complex, a porphyrin platinum complex is preferable. The phosphorescent compound may be used singly or in combination of two or more.

There are various ligands forming an ortho-metalated metal complex. As a preferred ligand, a 2-phenylpyridine derivative, a 7,8-benzoquinoline derivative, a 2-(2-thienyl)pyridine derivative, a 2-(1-naphthyl)pyridine derivative, a 2-phenylquinoline derivative or the like can be given. These derivatives may have substituents, if necessary. In particular, those obtained by introducing a fluorine compound or a trifluoromethyl group are preferable as a blue dopant. It may have a ligand other than the above-mentioned ligands, e.g. acetylacetonate and picric acid, as an auxiliary ligand.

The content of the phosphorescent dopant in the emitting layer is not particularly restricted, and it may be appropriately selected depending on the purpose. For example, the content is 0.1 to 70 mass %, with 1 to 30 mass % being preferable. When the content of the phosphorescent compound is 0.1 mass % or more, it is possible to prevent emission from becoming weak, whereby the effects of the presence of the phosphorescent dopant can be fully exhibited. By allowing the content to be 70 mass % or less, it is possible to suppress a phenomenon called concentration quenching, thereby to prevent lowering of device performance.

According to need, the emitting layer may contain a hole-transporting material, an electron-transporting material and a polymer binder.

The thickness of the emitting layer is preferably 5 to 50 nm, more preferably 7 to 50 nm, and most preferably 10 to 50 nm. By allowing the thickness of the emitting layer to be 5 nm or more, formation of the emitting layer becomes easy, whereby adjustment of chromaticity is facilitated. By allowing the thickness to be 50 nm or less, an increase in driving voltage can be prevented.

(B) Hole-Transporting Region

As the layers of the hole-transporting region, a hole-transporting layer, a hole-injecting layer or the like can be mentioned. The hole-transporting layer is a layer that assists injection of holes into the emitting layer, and transports holes to the emitting region. The hole-transporting layer exhibits a high hole mobility, and normally has a low ionization energy of 5.5 eV or less. It is preferable to form the hole-transporting layer using a material that transports holes to the emitting layer at a lower field intensity. It is more preferable to use a material having a hole mobility of at least $10^{-4}$ cm$^2$/V·s when an electric field of $10^4$ to $10^6$ V/cm is applied, for example.

Specific examples of the material for forming the hole-transporting layer include triazole derivatives, oxadiazole derivatives, imidazole derivatives, polyarylalkane derivatives, pyrazoline derivatives and pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, polysilane-based copolymers, aniline-based copolymers, conductive high-molecular polymers (in particular, thiophene oligomer) or the like.

In the hole-injecting layer or the hole-transporting layer (including the hole-injecting/transporting layer), an aromatic amine compound, for example, an aromatic amine derivative represented by the following formula (4) is preferably employed.

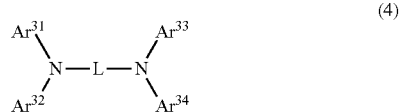

(4)

In the formula (4), Ar$^{31}$ to Ar$^{34}$ are an aromatic hydrocarbon group including 6 to 50 ring carbon atoms (it may have a substituent), a fused aromatic hydrocarbon group including 6 to 50 ring carbon atoms (it may have a substituent), an aromatic heterocyclic group including 2 to 40 ring carbon atoms (it may have a substituent), a fused aromatic heterocyclic group including 2 to 40 ring carbon atoms (it may have a substituent), a group formed by bonding of the aromatic hydrocarbon group with the aromatic heterocyclic group, a group formed by bonding of the aromatic hydrocarbon group with the fused aromatic heterocyclic group, a group formed by bonding of the fused aromatic hydrocarbon group with the aromatic heterocyclic group, or a group formed by bonding of the fused aromatic hydrocarbon group with the fused aromatic heterocyclic group.

L is a single bond or a group similar to $Ar^{31}$ to $Ar^{34}$.

The aromatic amine represented by the following formula (5) is preferably used for the formation of the hole-injecting layer or the hole-transporting layer.

(5)

In the formula (5), $Ar^{31}$ to $Ar^{33}$ are as defined for $Ar^{31}$ to $Ar^{34}$ in the formula (4).

The hole-injecting layer is a layer that is provided for further assisting injection of holes. As the material for the hole-injecting layer, the material for an organic EL device of the invention may be used alone or in combination with other materials. As other materials, similar materials to those for the hole-transporting layer can be used. In addition, a porphyrin compound, an aromatic tertiary amine compound and a styrylamine compound can also be used. Further, HAT or F4TCNQ used in the P layer of the charge-generating layer or a compound represented by the formula (4) can be used.

Further, electroconductive oligomers such as thiophene-containing oligomers or arylamine-containing oligomers disclosed in JP-A-H08-193191 and electroconductive dendrimers such as arylamine-containing dendrimers may be used.

Further, in addition to an aromatic dimethylidene-based compound, an inorganic compound such as p-type Si and p-type SiC can also be used as the material of the hole-injecting layer.

The hole-injecting layer or the hole-transporting layer can be formed in the shape of a thin film from the above-mentioned compounds by a known method such as vapor vacuum deposition, spin coating, casting or LB technique. The film thickness of the hole-injecting layer and the hole-transporting layer is not particularly limited, and is usually from 1 nm to 5 μm.

(C) Electron-Transporting Zone

As the layers of the electron-transporting zone, an electron-injecting layer, an electron-transporting layer or the like (hereinafter, referred to as the electron-injecting layer/transporting layer) can be mentioned.

The electron-injecting/transporting layer is a layer that assists injection of electrons into the emitting layer, and transports electrons to the emitting region. The electron-injecting/transporting layer exhibits a high electron mobility.

The thickness of the electron-injecting/transporting layer is appropriately selected within a range of several nanometers to several micrometers. In particular, when the electron-injecting/transporting layer has a large thickness, it is preferable that the electron mobility be at least $10^{-5}$ cm$^2$/Vs at an applied electric field of $10^4$ to $10^6$ V/cm in order to prevent an increase in voltage.

The material used in the electron-injecting/transporting layer is preferably a metal complex of 8-hydroxyquinoline or a derivative thereof, or a nitrogen-containing heterocyclic derivative.

Specific examples of the metal complex of 8-hydroxyquinoline or the derivative thereof include metal chelate oxynoid compounds containing a chelate of oxine (generally, 8-quinolinol or 8-hydroxyquinoline). For example, tris(8-quinolinol)aluminum can be used as an electron-injecting material.

As the nitrogen-containing heterocyclic derivative, oxazole, thiazole, oxadiazole, thiadiazole, triazole, pyridine, pyrimidine, triazine, phenanthroline, benzimidazole, imidazopyridine or the like are preferable. Among them, a benzimidazole derivative, a phenanthroline derivative and an imidazopyridine derivative are preferable.

(Charge-Generating Layer)

A charge-generating layer is a layer which, when a voltage is applied, serves to inject holes to an emitting unit arranged on the side nearer to the cathode of the charge-generating layer, and on the other hand, serves to inject electrons to an emitting unit arranged on the side nearer to the anode of the charge-generating layer.

In the invention, the charge-generating layer has the N layer provided on the side nearer to the anode and the P layer provided on the side nearer to the cathode. The N layer is as mentioned above.

The thickness of the N layer is preferably 0.1 nm to 100 nm, particularly preferably 1 nm to 50 nm.

As the P layer, a layer containing the compound represented by the following formula (III) can be mentioned.

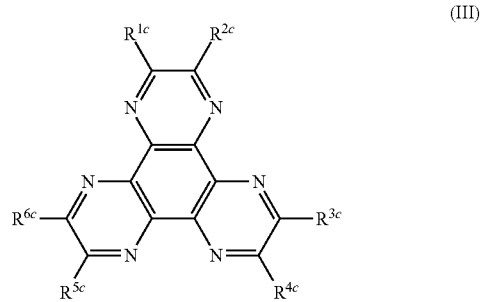

(III)

Since the compound represented by the formula (III) improves the device properties such as efficiency. voltage and life, it is used in the charge-generating layer. However, due to the high conductivity of the compound represented by the formula (III), current leakage between pixels through the charge-generating layer may occur. By combining the N layer of the invention and the layer containing the compound represented by the formula (III), current leakage between adjacent pixels can be suppressed.

$R^{1c}$ to $R^{6c}$ in the formula are independently a hydrogen atom, a substituted or unsubstituted aryl group including 6 to 60 ring carbon atoms, a substituted or unsubstituted pyridyl group, a substituted or unsubstituted quinolyl group, a substituted or unsubstituted alkyl group including 1 to 50 carbon atoms, a substituted or unsubstituted cycloalkyl group including 3 to 50 carbon atoms, a substituted or unsubstituted aralkyl group including 7 to 50 ring carbon atoms, a substituted or unsubstituted alkoxy group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, an amino group substituted with a substituted or unsubstituted aryl group including 6 to 50 ring carbon atoms, a halogen atom, a cyano group, a nitro group, a hydroxyl group or a carboxyl group.

Specific examples of the substituted or unsubstituted aryl group including 6 to 60 ring carbon atoms or the like are the same as the examples of the compound in the formula (I) or the like.

Specific examples of the compound represented by formula (III) are shown below. For other examples, reference can be made to JP-T-2011-521414.

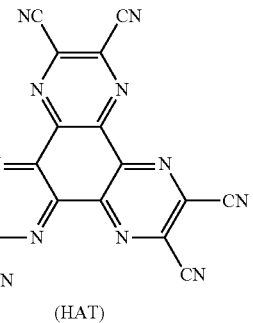

(HAT)

Further, a layer containing the compound represented by the following formula (IV) can be mentioned. By combining the N layer of the invention and the layer containing the compound represented by the formula (IV), effects of improving properties such as the luminance of a device, lowering in driving voltage and prolongation of a life, etc. become significant.

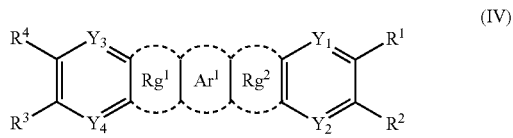

(IV)

In the above formula (IV), $Ar^1$ is an aromatic ring including 6 to 24 ring carbon atoms or a heterocyclic ring including 5 to 24 ring atoms. Preferably, $Ar^1$ is an aromatic ring including 6 to 14 ring carbon atoms or a heterocyclic ring including 5 to 14 ring atoms. As the aromatic ring, a benzene ring, a naphthalene ring, a fluorene ring, a 9,9-dimethylfluorene ring, a 9,9-dioctylfluorene ring and the like can be given. As the heterocyclic ring, a pyrazine ring, a pyridine ring, a quinoxaline ring, a thiophene ring, a benzothiophene ring, a dibenzothiophene ring, a furan ring, a benzofuran ring, a dibenzofuran ring, a phenanthroline ring, a naphthyridine ring, a tetraaza-anthracene ring and the like can be given. The aromatic ring and the heterocyclic ring may be substituted with a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxy group, a substituted or unsubstituted fluoroalkoxy group, a substituted or unsubstituted aryloxy group, a substituted or unsubstituted aralkyloxy group, a substituted or unsubstituted amino group, a substituted or unsubstituted silyl group, or a cyano group, as represented by $R^1$ to $R^4$ given below.

In the formula (IV). $R_1$ to $R^4$ may be the same or different from each other, and are a hydrogen atom, a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxy group, a substituted or unsubstituted fluoroalkoxy group, a substituted or unsubstituted aryloxy group, a substituted or unsubstituted aralkyloxy group, a substituted or unsubstituted amino group, a substituted or unsubstituted silyl group, or a cyano group. $R^1$ and $R^2$ may be bonded each other to form a ring and $R^3$ and $R^4$ may be bonded each other to form a ring.

Examples of the alkyl group include a methyl group, an ethyl group, an n-propyl group, an isopropyl group, an n-butyl group, an isobutyl group, a tert-butyl group and an octyl group.

As the cycloalkyl group, a cyclopentyl group, a cyclohexyl group or the like can be given.

As the alkenyl group, a vinyl group, a propenyl group (including a regioisomer of a double bond), a butenyl group (including a regioisomer of a double bond), a pentenyl group (including a regioisomer of a double bond) or the like can be given.

As the (substituted) aryl group, a phenyl group, a biphenyl group, a naphthyl group, a fluorophenyl group, a trifluoromethylphenyl group, a (trifluoromethyl)fluorophenyl group, a trifluorophenyl group, a bis(trifluoromethyl)phenyl group, a (trifluoromethyl)difluorophenyl group, a trifluoromethoxyphenyl group, a trifluoromethoxyfluorophenyl group or the like can be given.

As the heterocyclic group, residues of pyridine, pyrazine, furan, imidazole, benzimidazole, thiophene or the like can be given.

As the halogen atom, a fluorine atom, a chlorine atom, a bromine atom or an iodine atom can be mentioned.

As the fluoroalkyl group, a trifluoromethyl group, a pentafluoroethyl group, a perfluorocyclohexyl group, a perfluoroadamantyl group or the like can be mentioned.

As the alkoxy group, a methoxy group, an ethoxy group or the like can be mentioned.

As the fluoroalkoxy group, a trifluoromethoxy group, a pentafluoroethoxy group, a 2,2,2-trifluoroethoxy group, a 2,2,3,3,3-pentafluoropropoxy group, a 2,2,3,3-tetrafluoropropoxy group, a 1,1,1,3,3,3-hexafluoropropane-2-yloxy group or the like can be mentioned.

As the (substituted) aryloxy group, a phenyloxy group, a pentafluorophenyloxy group, a 4-trifluorophenyloxy group or the like can be mentioned.

As the (substituted) aralkyloxy group, a benzyloxy group, a pentafluorobenzyloxy group, a 4-trifluoromethylbenzyloxy group or the like can be mentioned.

As the (substituted) amino group, an amino group, a mono- or dimethylamino group, a mono- or diethylamino group, a mono- or diphenylamino group or the like can be mentioned.

As the (substituted) silyl group, a silyl group, a mono-, di- or trimethylsilyl group, a mono-, di- or triethylsilyl group, a mono-, di- or triphenylsilyl group or the like can be mentioned.

As the examples of the arbitral substituent of $R^1$ to $R^4$, the halogen atom, the cyano group, the alkyl group, the aryl group, the fluoroalkyl group, the fluoroalkoxy group and the heterocyclic group mentioned above can be given.

In the present application, unless otherwise specified, as the examples of the arbitral substituent when referring to the "substituted or unsubstituted", the halogen atom, the cyano group, the alkyl group, the aryl group, the fluoroalkly group, the fluoroalkoxy group and the heterocyclic group given above can be mentioned.

As mentioned above, W and $R^2$ may be bonded each other to form a ring and $R^3$ and $R^4$ may be bonded with each other to form a ring. As examples of the ring, a benzene ring, a naphthalene ring, a pyrazine ring, a pyridine ring, a furan ring or the like can be given.

At least one of $R^1$ to $R^4$ is preferably a fluorine atom, a fluoroalkyl group, a fluoroalkoxy group, a cyano group, or an aryl group or a heterocyclic group having at least one group selected from fluorine, a fluoroalkyl group, a fluoroalkoxy group and a cyano group. By having these groups as a substituent, electron acceptability can be enhanced, an appropriate sublimation temperature can be obtained or crystallization can be suppressed.

The $Rg^1$ and the $Rg^2$ in the formula (IV) may be the same or different from each other and are represented by the following formula (i) or (ii).

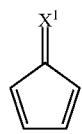
(i)

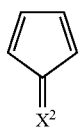
(ii)

In the above formula, $X^1$ and $X^2$ may be the same or different from each other and are any of divalent groups represented by the following (a) to (g). Divalent groups represented by (a), (b) or (c) are preferable in respect of excellent heat resistance, easiness in synthesis or the like.

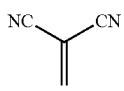
(a)

(b)

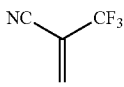
(c)

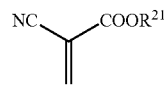
(d)

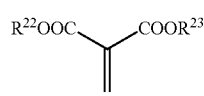
(e)

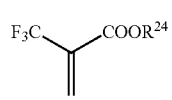
(f)

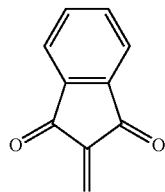
(g)

$R^{21}$ to $R^{24}$ in the above formula may be the same or different from each other, and are a hydrogen atom, a substituted or unsubstituted fluoroalkyl group, a substituted or unsubstituted alkyl group, a substituted or unsubstituted cycloalkyl group, a substituted or unsubstituted aryl group, a substituted or unsubstituted heterocyclic group, and $R^{22}$ and $R^{23}$ may be bonded each other to form a ring. As specific examples of the fluoroalkyl group, the alkyl group, the cycloalkyl group, the aryl group and the heterocyclic group, the groups mentioned above referring to $R^1$ to $R^4$ can be given.

$Y^1$ to $Y^4$ in the formula (IV) may be the same or different from each other, and are N, CH, or $C(R^5)$, wherein $R^5$ is the same as $R^1$ to $R^4$.

It is preferred that at least one of $Y^1$ to $Y^4$ be a nitrogen atom (the same applies to $Y^{21}$ to $Y^{26}$ and $Y^{31}$ to $Y^{38}$ mentioned later). If at least one of $Y^1$ to $Y^4$ is a nitrogen atom, electron acceptability can be enhanced, heat resistance can be increased or crystallization can be suppressed.

The indenofluorenedione derivative of the formula (IV) is preferably represented by the following formula (IV-A) or (I-B). Symbols such as $Ar^1$ in the following formula (IV-A) have the same meanings as those in the formula (IV). $Ar^2$ in the following formula (IV-B) is the same as $Ar^1$ in the formula (IV). $X^3$ and $X^4$ are the same as $X^1$ and $X^2$ in the formula (IV). $Y^5$ to $Y^8$ are the same as $Y^1$ to $Y^4$ in the formula (IV). $R^1$ to $R^4$ are the same as $R^1$ to $R^4$ in the formula (IV).

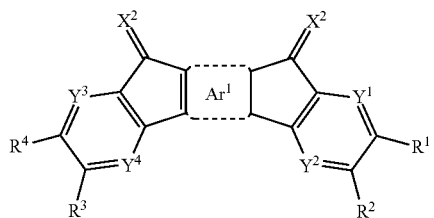
(IV-A)

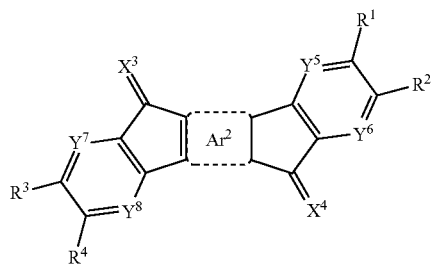
(IV-B)

It is further preferred that the indenofluorenedione derivative in the formula (IV) be represented by the following formulas (IVa) to (IVi).

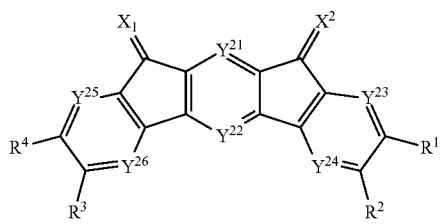
(IVa)

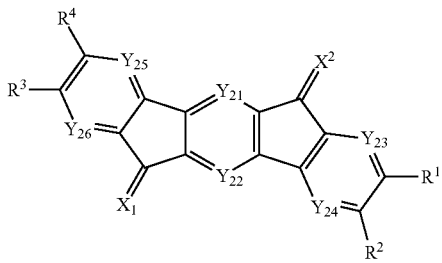
(IVb)

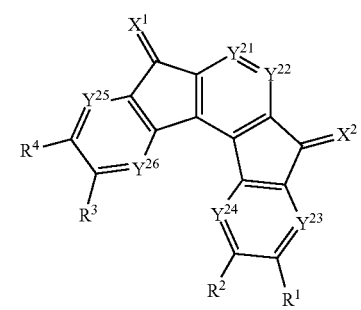
(IVc)

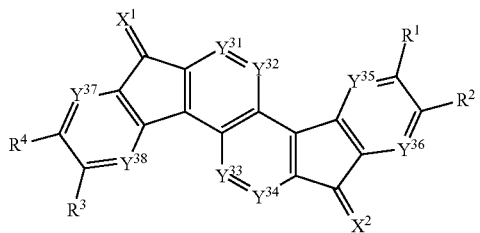
(IVd)

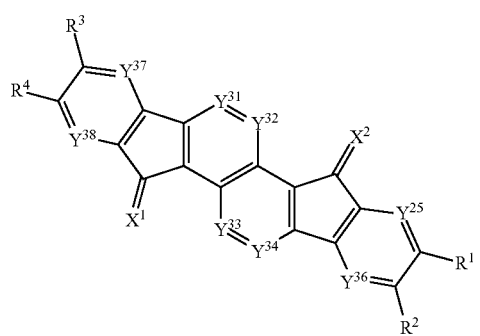
(IVe)

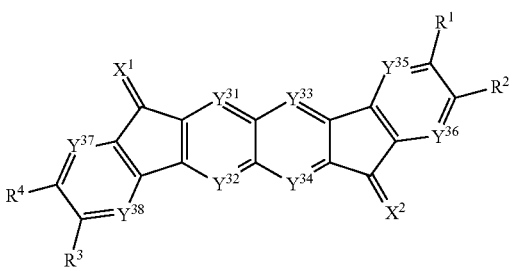
(IVf)

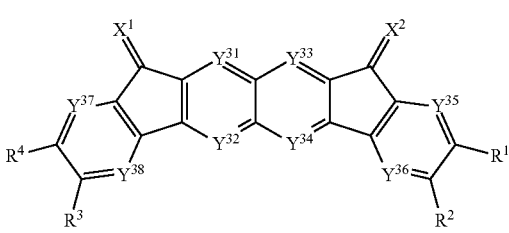
(IVg)

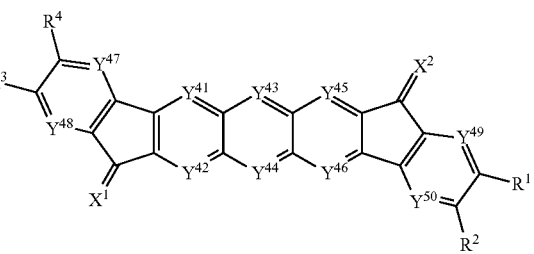
(IVh)

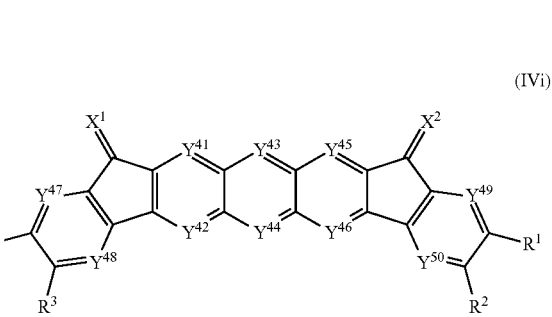
(IVi)

In the above formula, $X^1$ and $X^2$ and $R^1$ to $R^4$ are the same as $X^1$ and $X^2$ and $R^1$ to $R^4$ in the formula (IV) and $Y^{21}$ to $Y^{26}$, $Y^{31}$ to $Y^{38}$ and $Y^{41}$ to $Y^{50}$ are the same as $Y^1$ to $Y^4$ in the formula (IV).

Particularly preferable indenofluorenedione derivatives represented by the formula (IV) are represented by the following formulas (IV-a) to (IV-n). As for the following formula (IV-b), (IV-d), (IV-f), (IV-h), (IV-j), (IV-l), (IV-n), (IV-p) and (IV-r), a plurality of isomers are present due to the steric configuration of the cyano groups of the two cyanoimino groups. The invention is not limited to specific isomers. The derivative of the invention may be a specific isomer alone or may be a mixture of two or larger than two isomers.

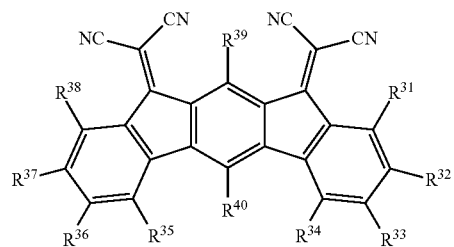
(IV-a)
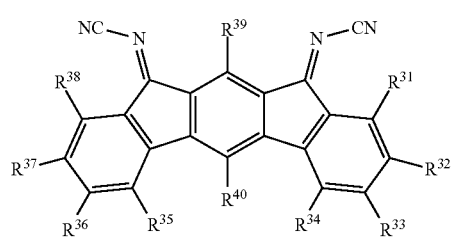
(IV-b)
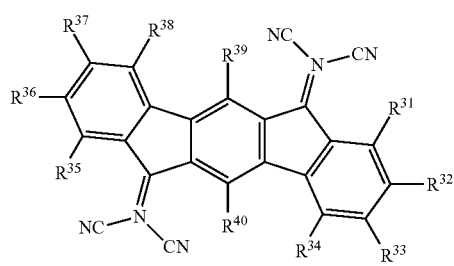
(IV-c)
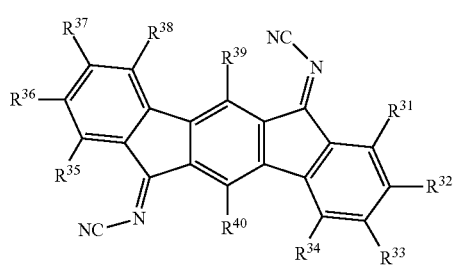
(IV-d)
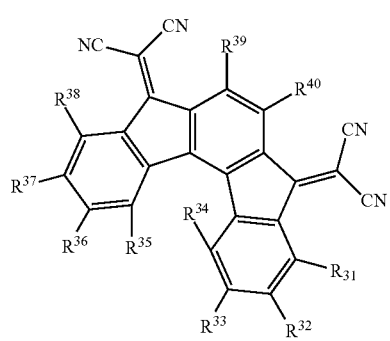
(IV-e)
-continued
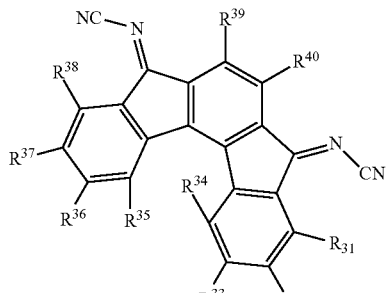
(IV-f)
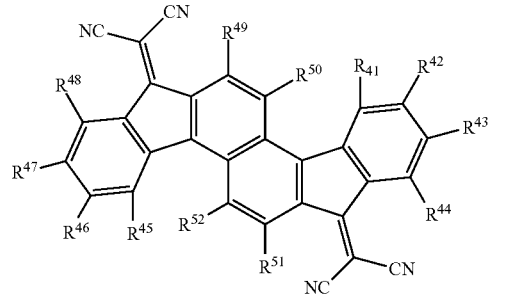
(IV-g)
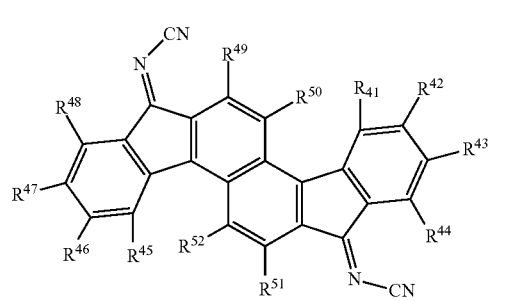
(IV-h)
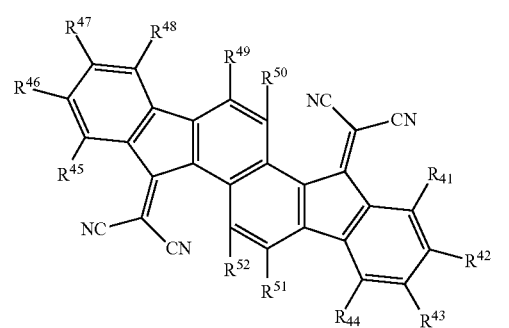
(IV-i)
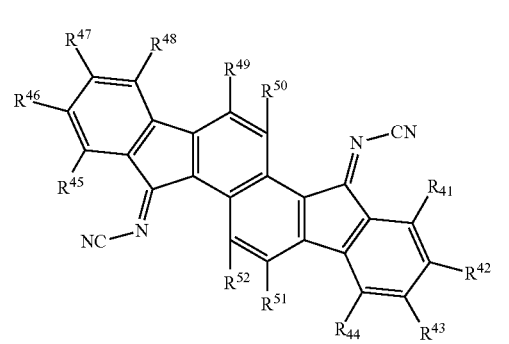
(IV-j)

(IV-k)

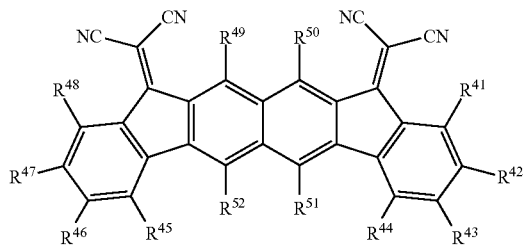

(IV-p)

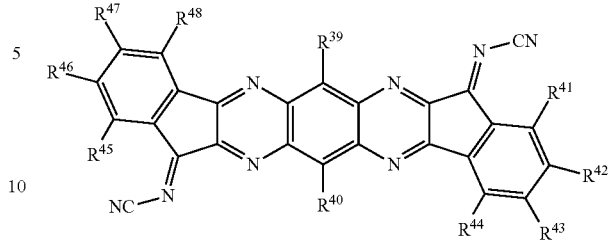

(IV-l)

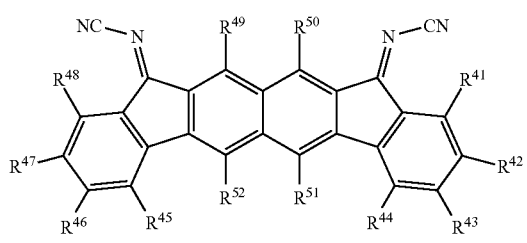

(IV-q)

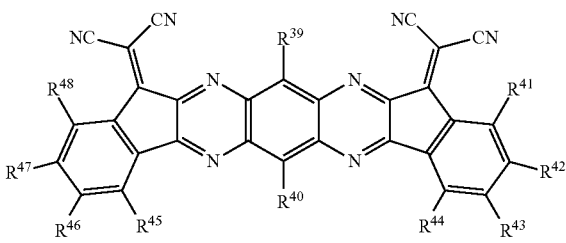

(IV-m)

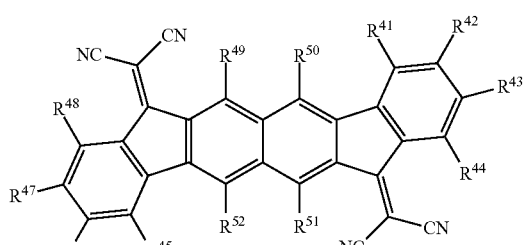

(IV-r)

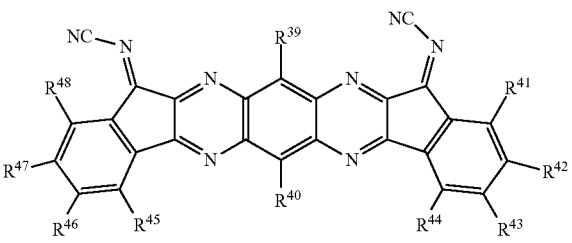

(IV-n)

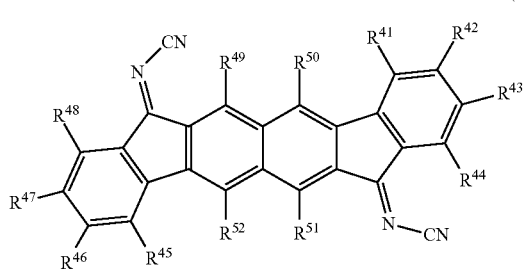

(IV-o)

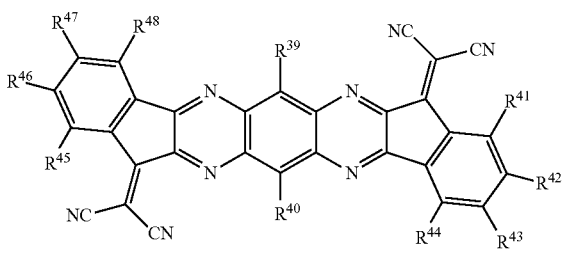

In the above formulas, $R^{31}$ to $R^{52}$ have the same meanings as $R^1$ to $R^4$ in the formula (IV). Adjacent two of $R^{31}$ to $R^{52}$ may be bonded each other to form a ring. In particular, it is preferred that at least one of $R^{31}$ to $R^{52}$ be a fluorine atom, a fluoroalkyl group, a fluoroalkoxy group, a cyano group or an aryl group or a heterocyclic group having at least one selected from fluorine, a fluoroalkyl group, a fluoroalkoxy group and a cyano group.

Due to the structure represented by each of the above-mentioned formulas, the indenofluorenedione derivative has electron acceptability. Further, since it has excellent heat resistance and a sublimation temperature of about 200° C. or more, the indenofluorenedione derivative is capable of being purified by sublimation, whereby it can have high purity. Further, by using in an organic EL device, the driving voltage of the device can be lowered, and the life thereof can be prolonged. Further, since the sublimation temperature is as high as about 200° C. or more, the derivative does not scatter to the inside of the deposition apparatus at the time of producing a device. Accordingly, there is no fear that the derivative contaminates a film-forming apparatus or an organic EL device.

Specific examples of the indenofluorenedione derivative represented by the formula (IV) are given below. The invention is, however, not limited to these specific examples.

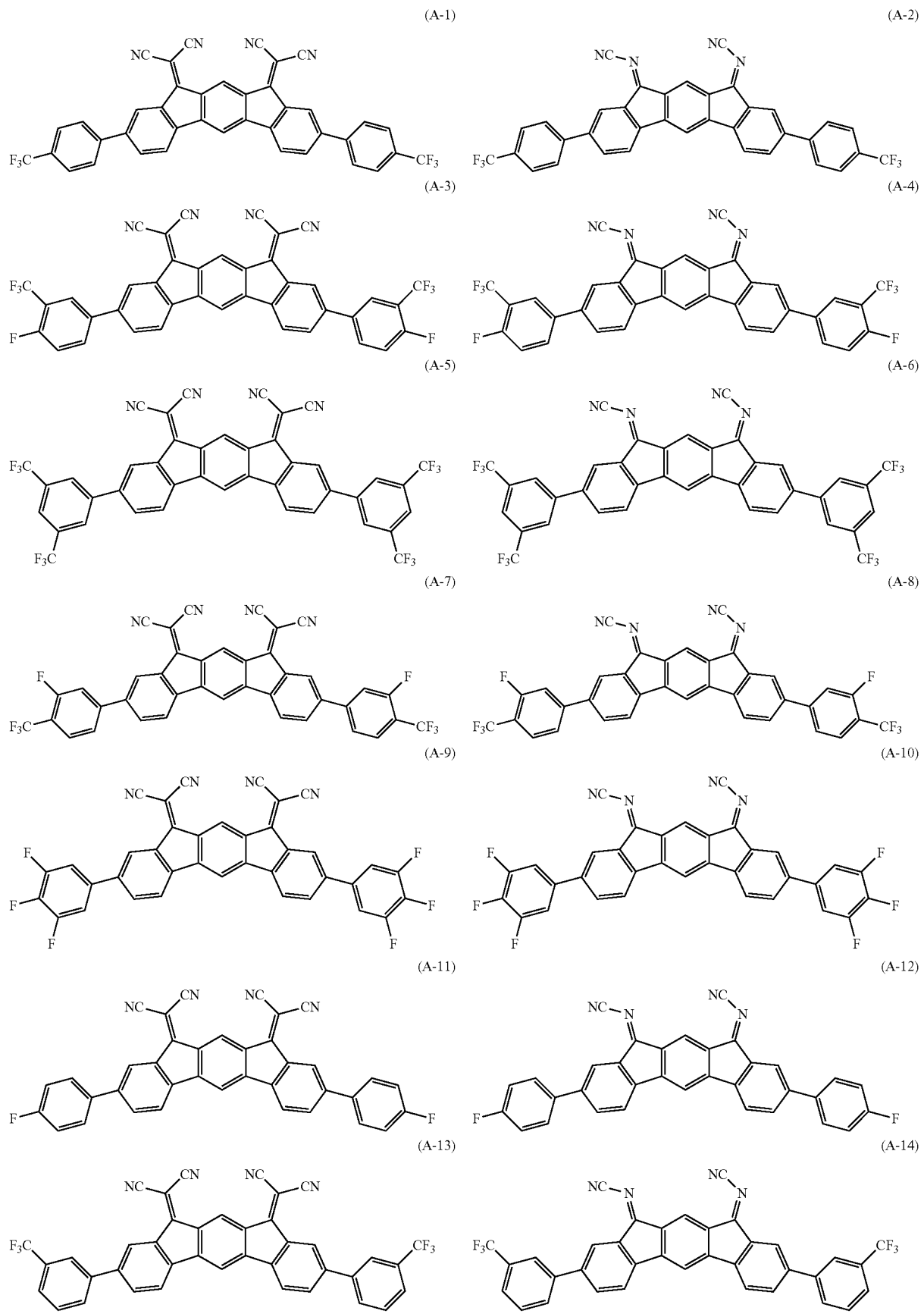

-continued
(A-15)
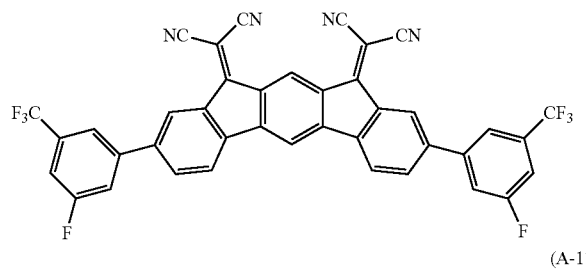
(A-16)
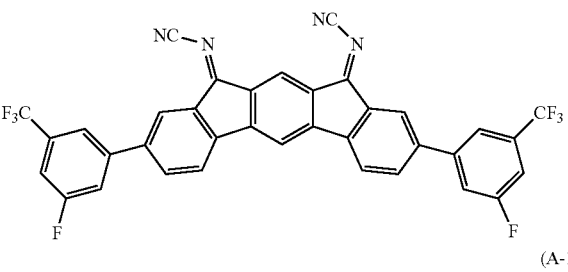
(A-17)
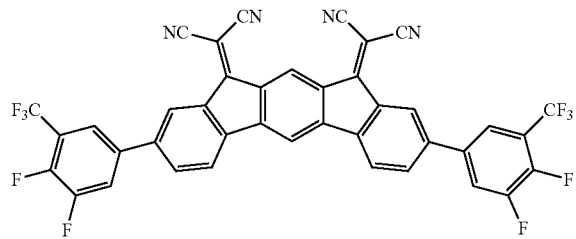
(A-18)
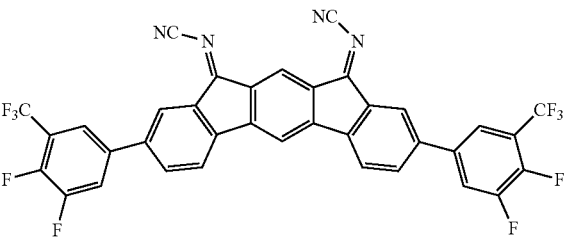
(A-19)
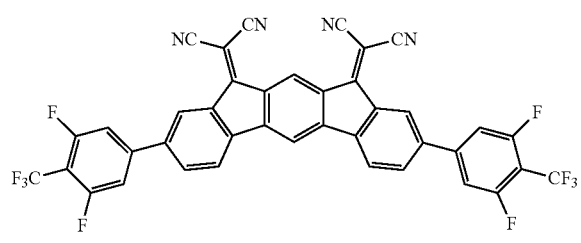
(A-20)
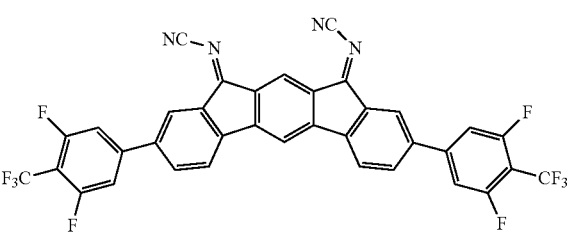
(A-21)
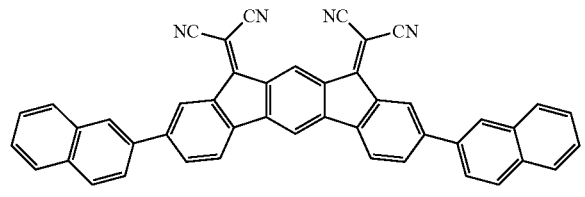
(A-22)
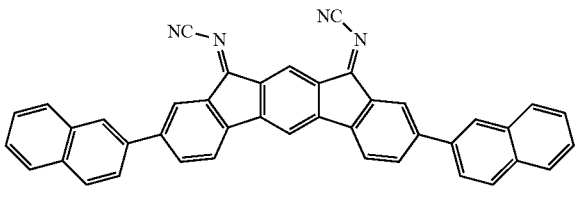
(A-23)
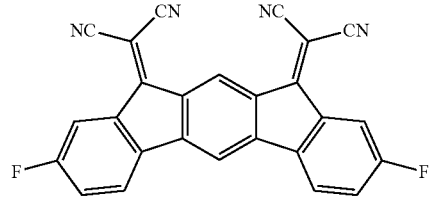
(A-24)
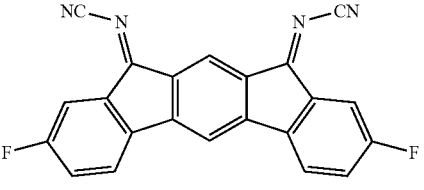
(A-25)
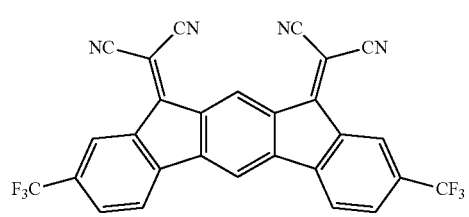
(A-26)
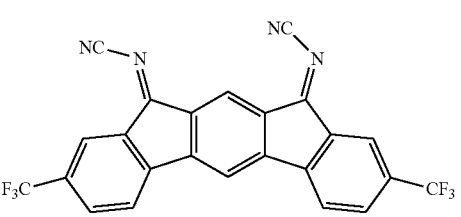
(A-27)
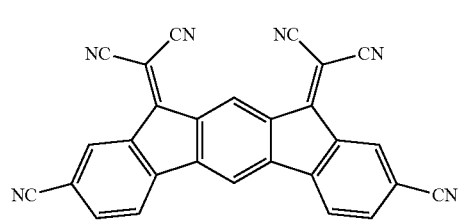
(A-28)
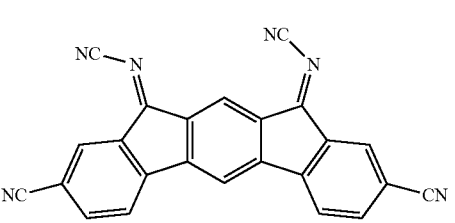

-continued
(A-29)
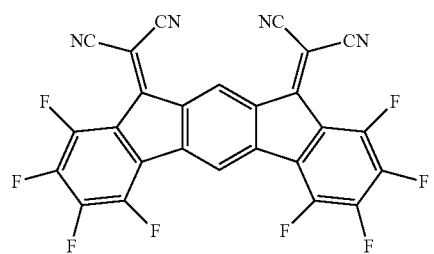
(A-30)
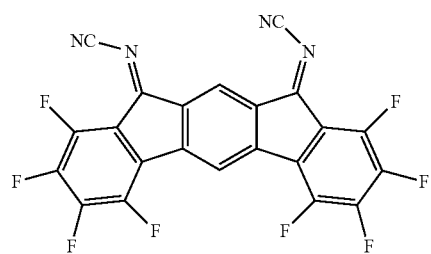
(A-31)
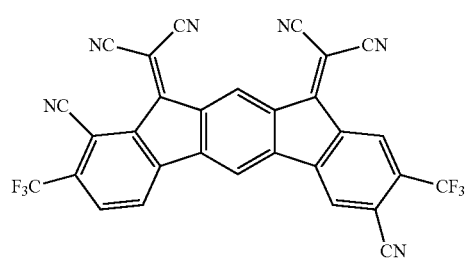
(A-32)
(A-33)
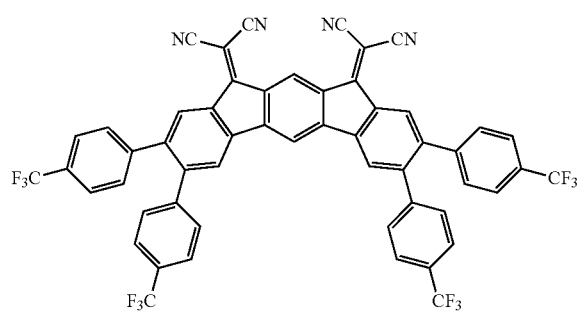
(A-34)
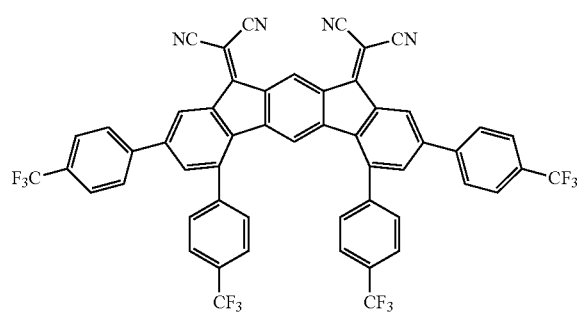
(A-35)
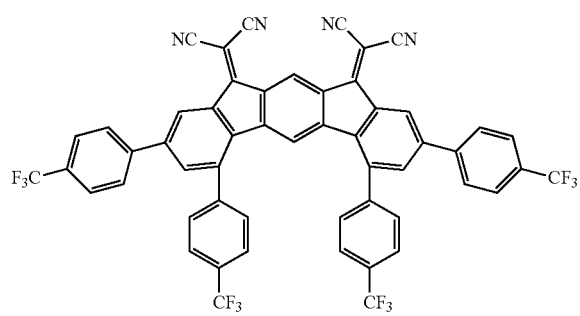
(A-36)
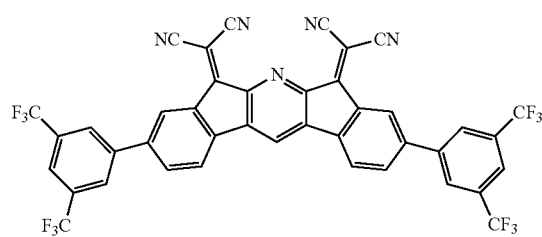
(A-37)
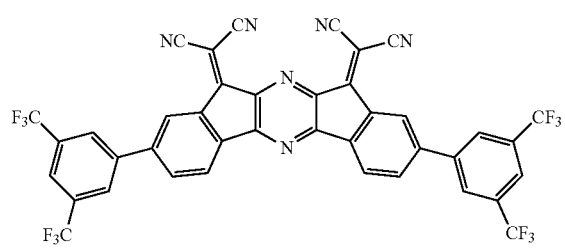
(A-38)
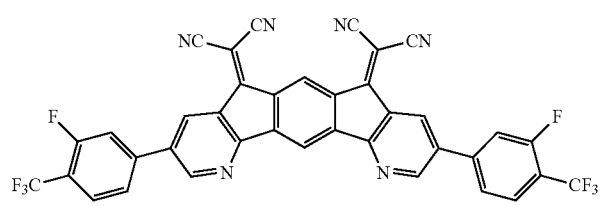

-continued
(A-39)
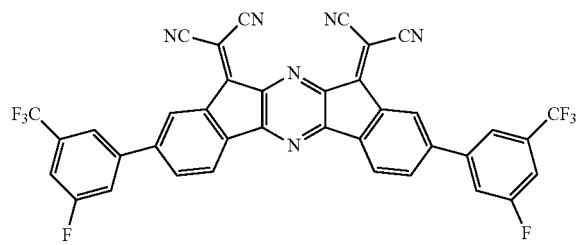
(A-40)
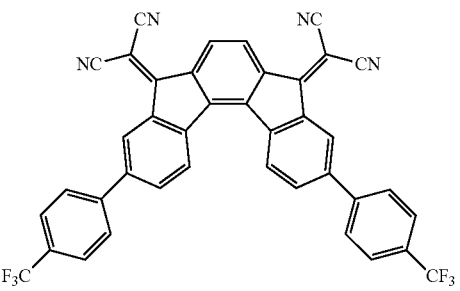
(A-41)
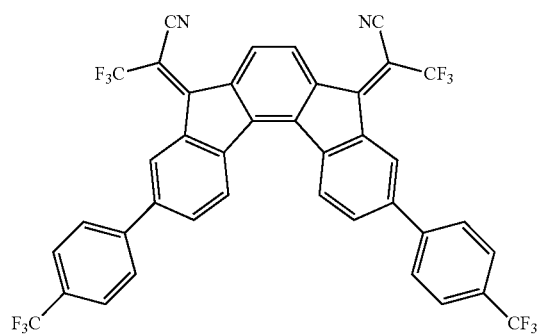
(A-42)
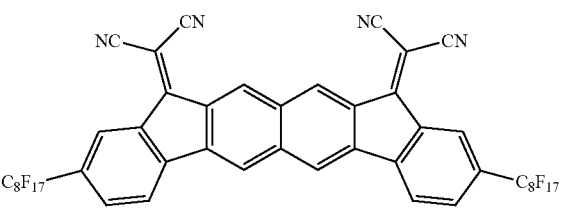
(A-43)
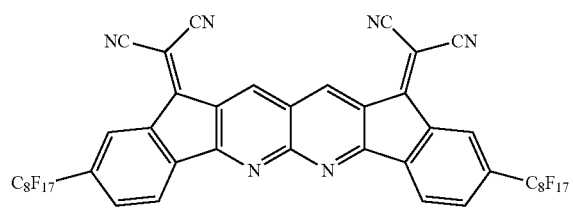
(A-44)
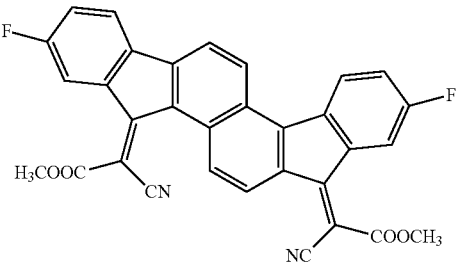
(A-45)
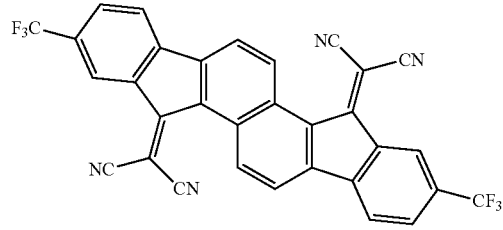
(A-46)
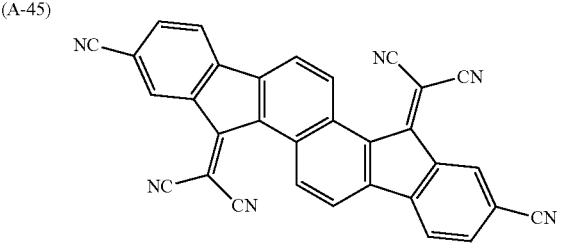
(A-47)
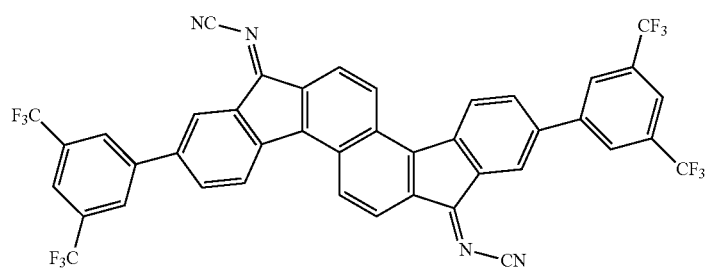

-continued
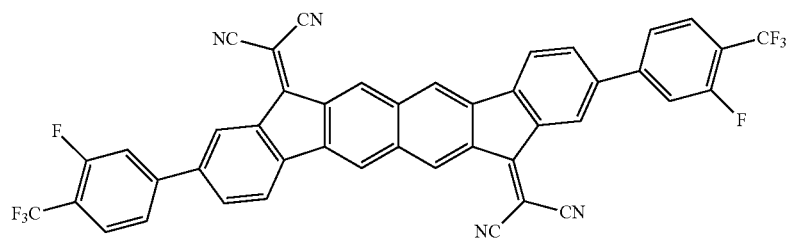
(A-48)
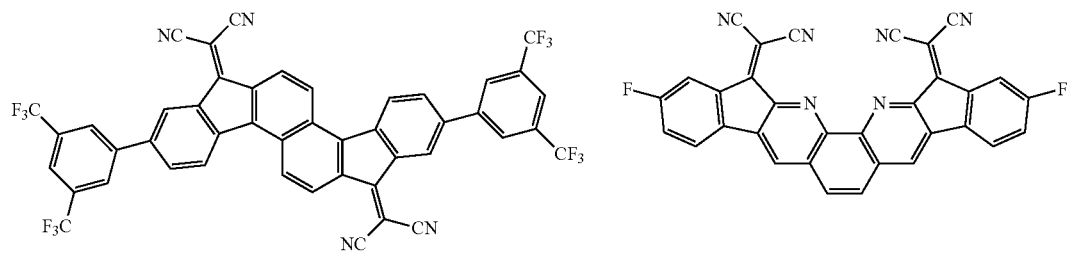
(A-49)                (A-50)
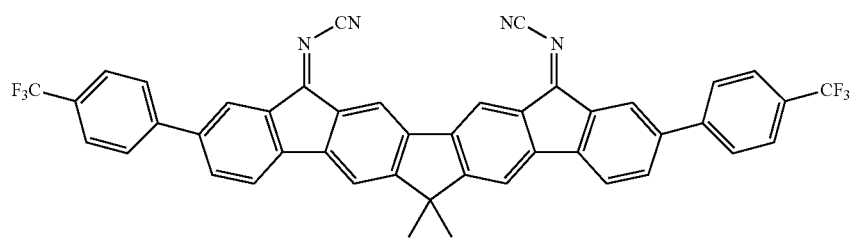
(A-51)
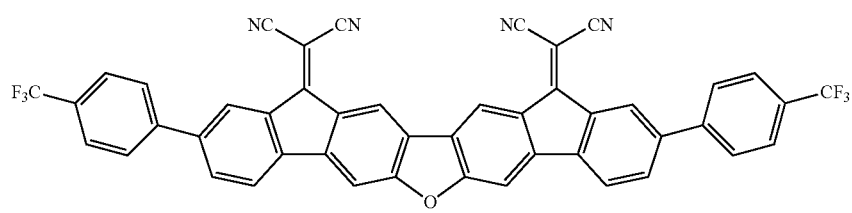
(A-52)
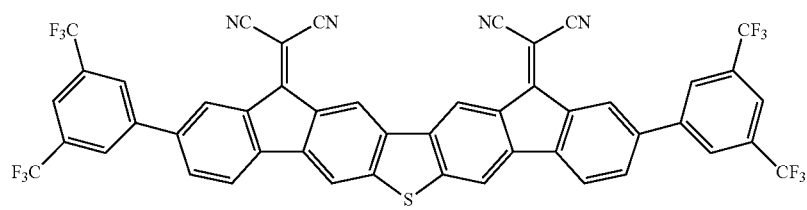
(A-53)
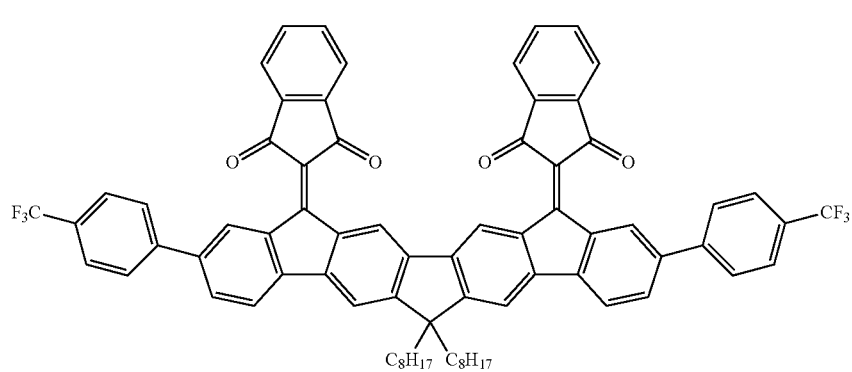
(A-54)

-continued
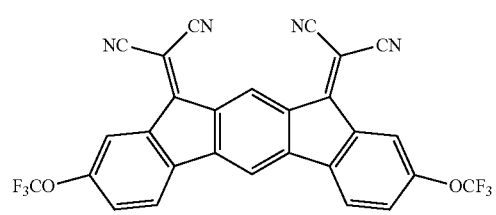
(A-55)
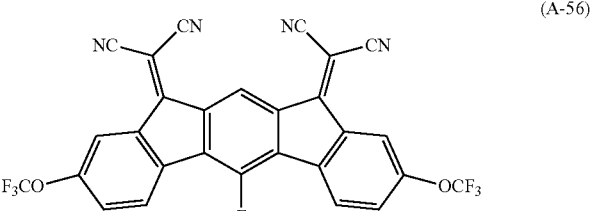
(A-56)
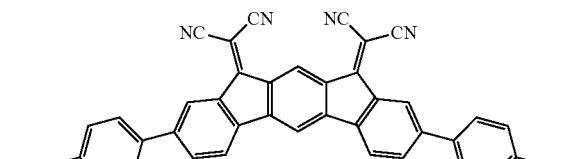
(A-57)
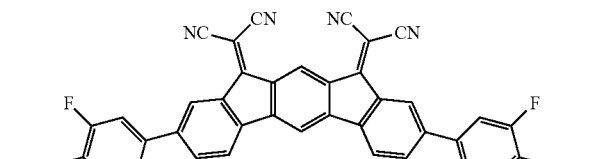
(A-58)
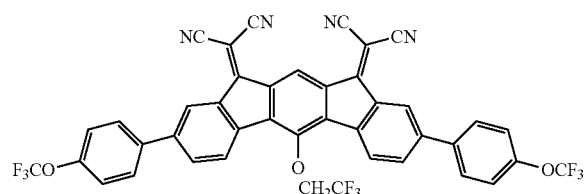
(A-59)
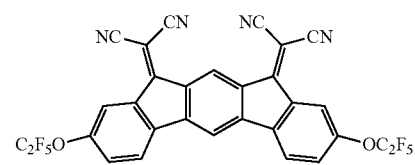
(A-60)
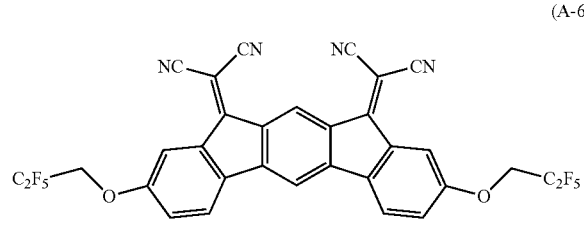
(A-61)
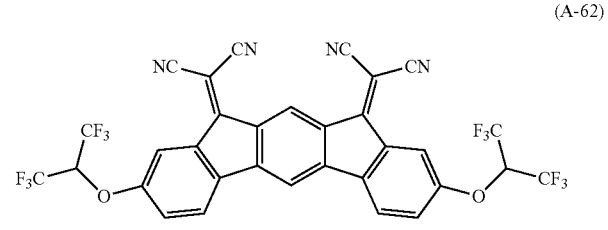
(A-62)
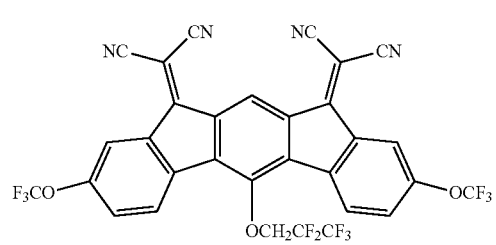
(A-63)
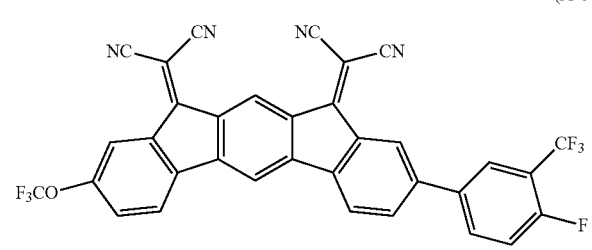
(A-64)
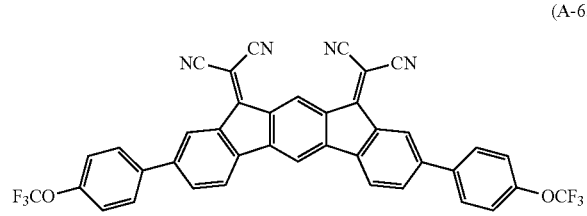
(A-65)
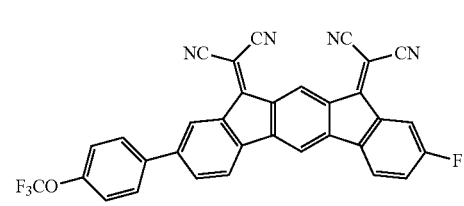
(A-66)
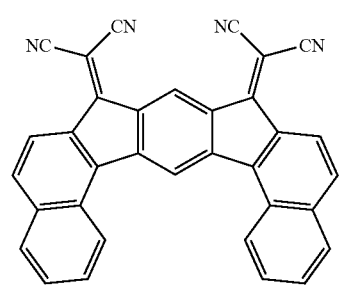
(A-67)
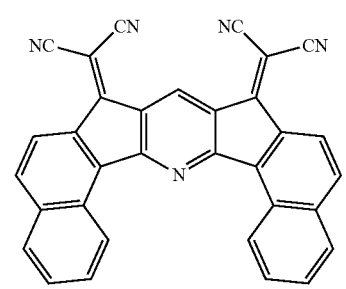
(A-68)

-continued
(A-69)
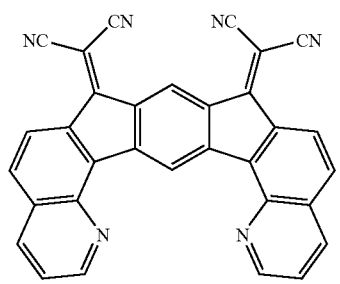
(A-70)
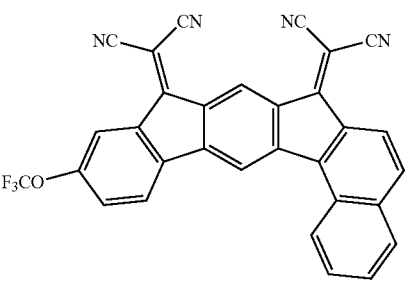
(A-71)
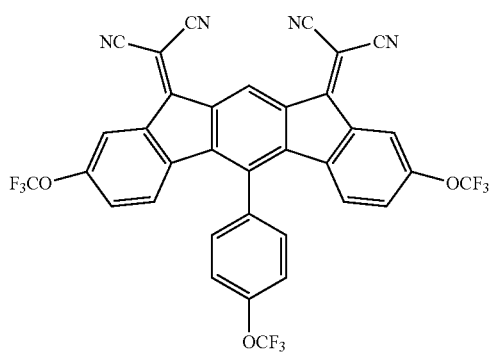
(A-72)
(A-73)
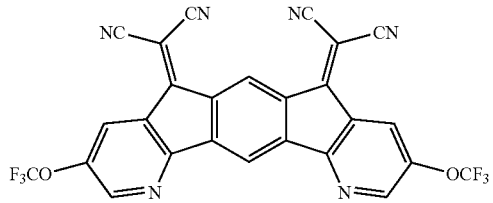
(A-74)
(A-75)
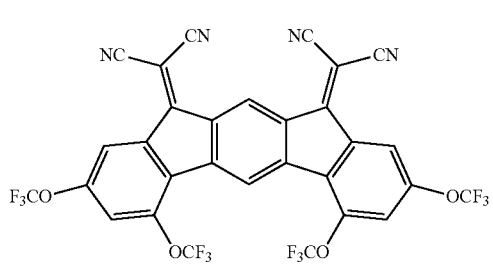
(A-76)
(A-77)
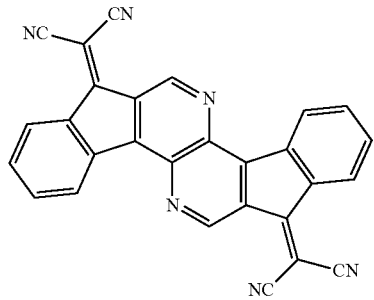
(A-78)
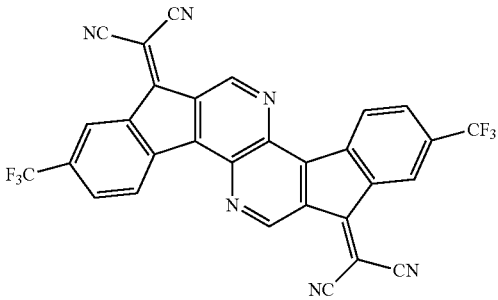

-continued
(A-79)
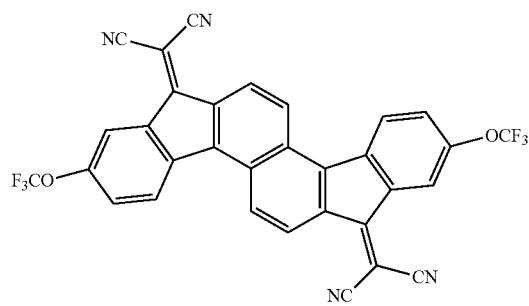
(A-80)
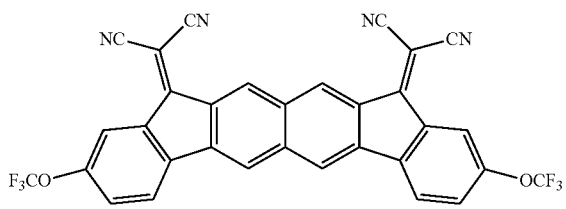
(A-81)
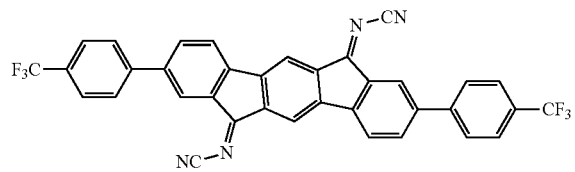
(A-82)
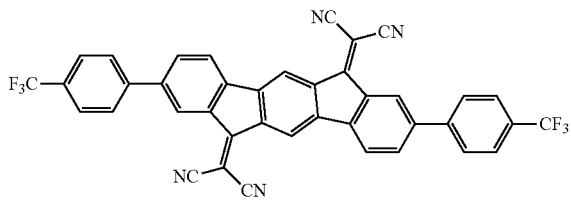
(A-83)
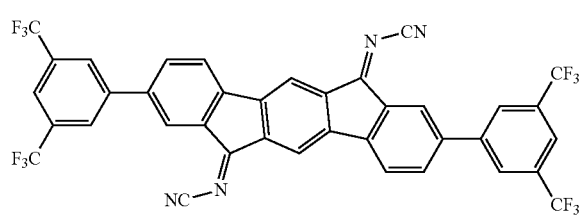
(A-84)
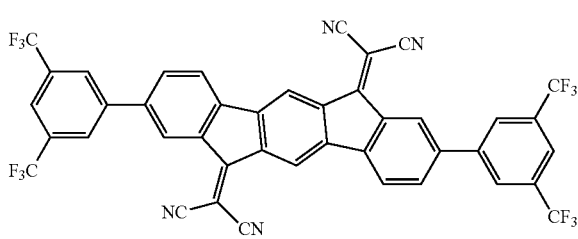
(A-85)
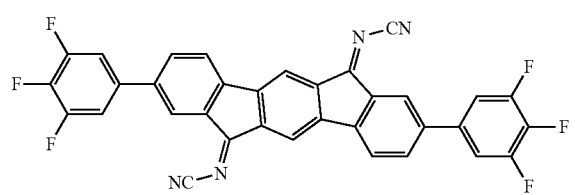
(A-86)
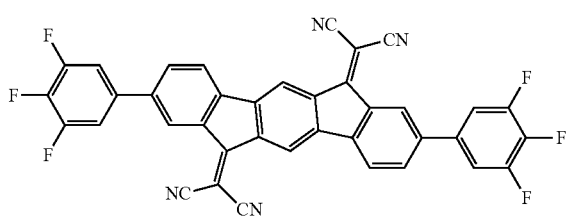
(A-87)
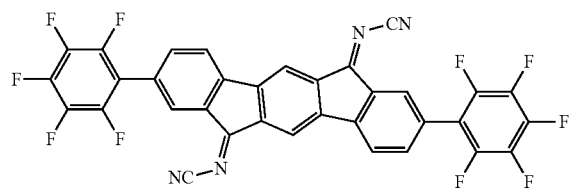
(A-88)
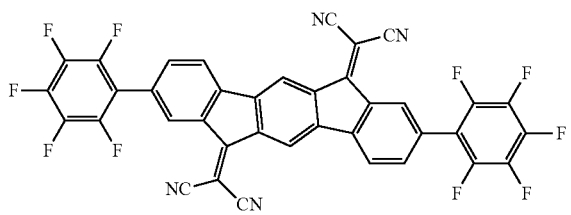
(A-89)
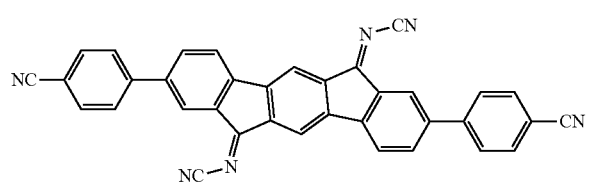
(A-90)
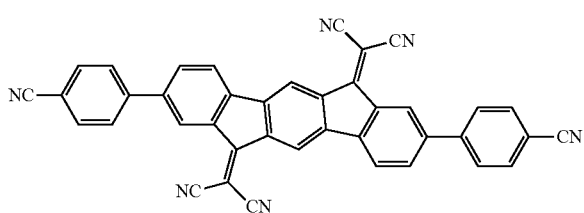

-continued
(A-91)
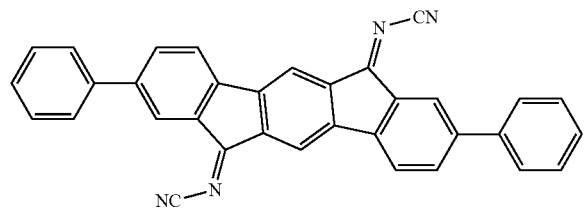
(A-92)
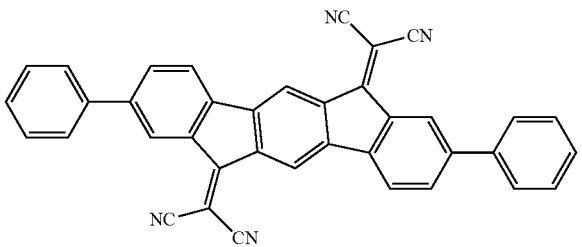
(A-93)
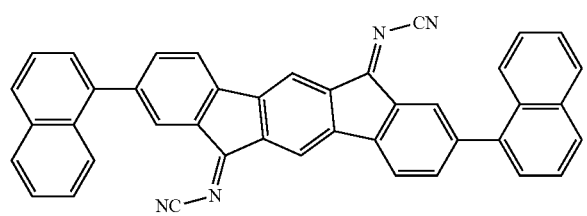
(A-94)
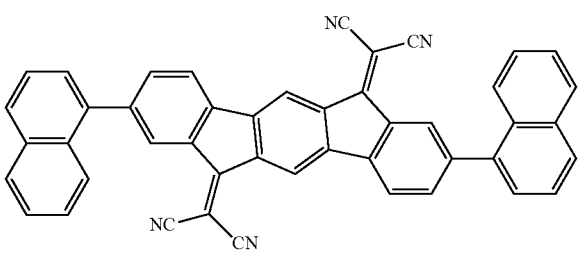
(A-95)
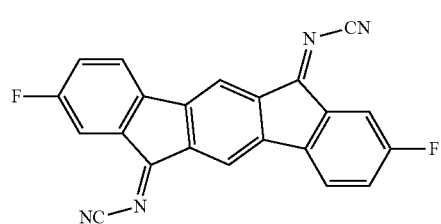
(A-96)
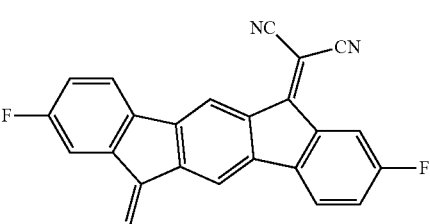
(A-97)
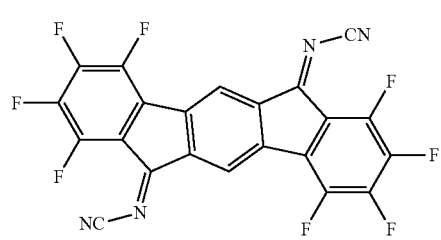
(A-98)
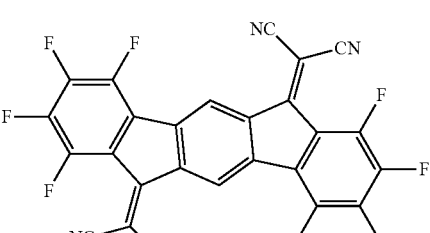
(A-99)
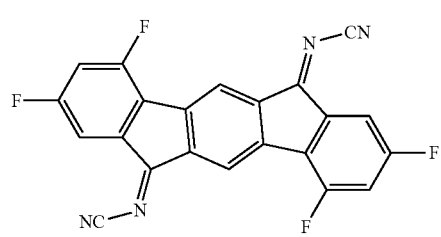
(A-100)
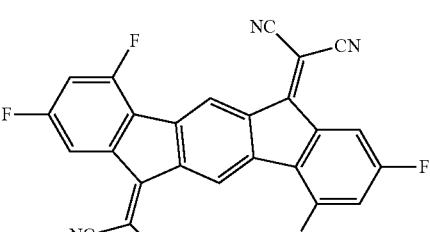
(A-101)
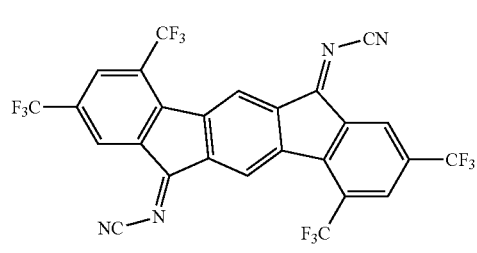
(A-102)

-continued
(A-103)
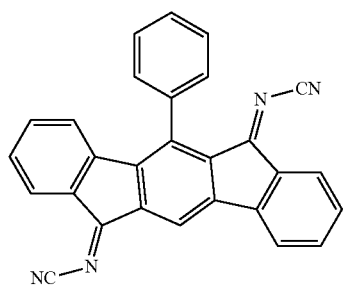
(A-104)
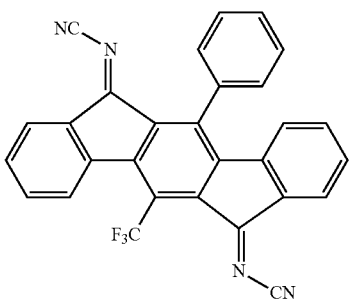
(A-105)
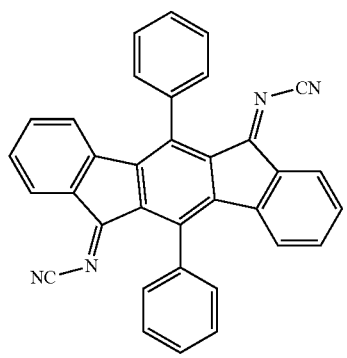
(A-106)
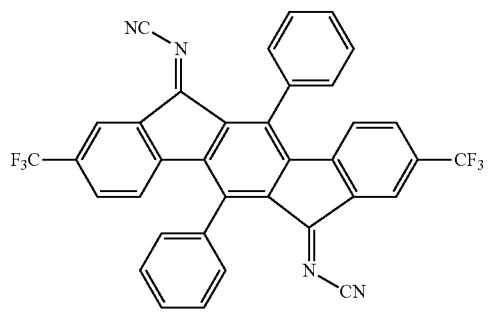
(A-107)
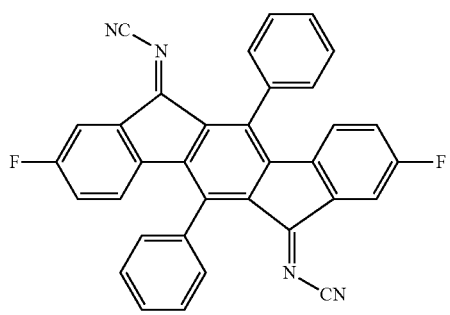
(A-108)
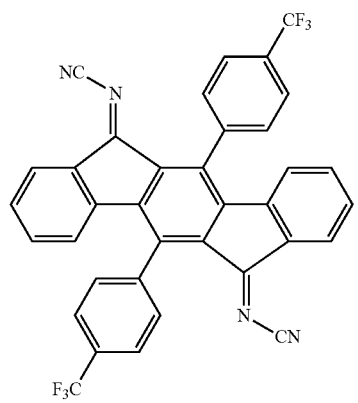
(A-109)
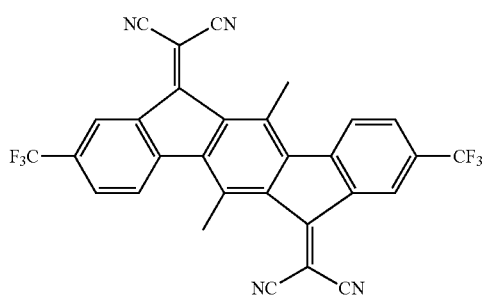
(A-110)
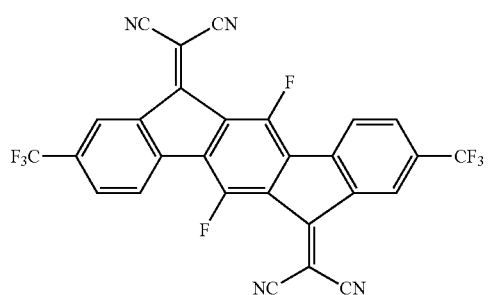

-continued
(A-111)
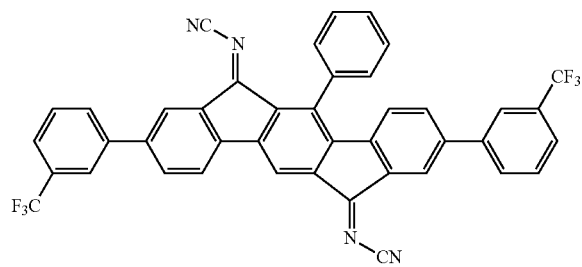
(A-112)
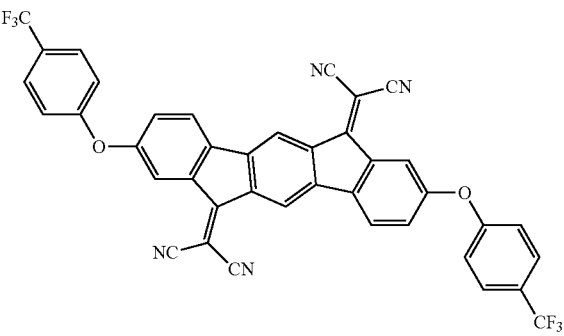
(A-113)
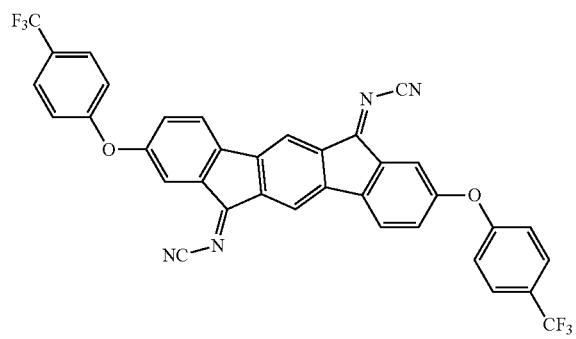
(A-114)
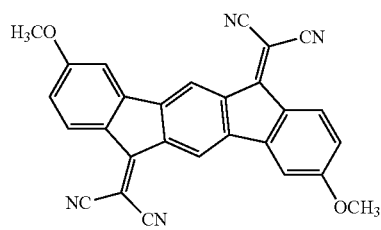
(A-115)
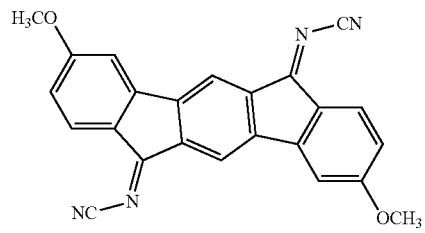
(A-116)
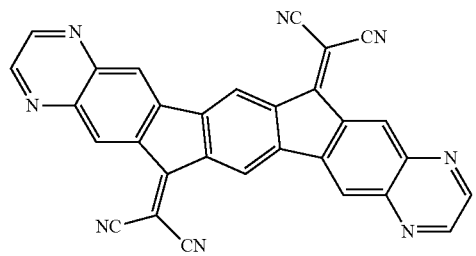
(A-117)
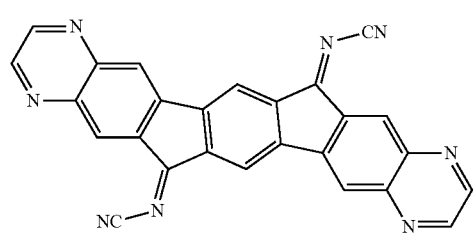
(A-118)
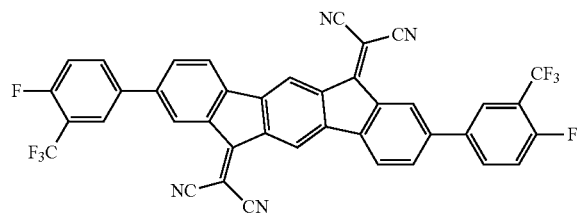
(A-119)
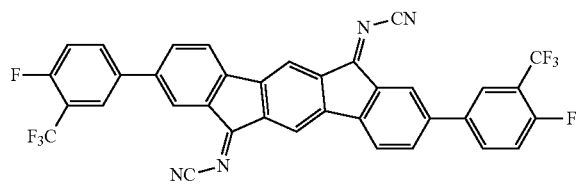

-continued
(A-120)
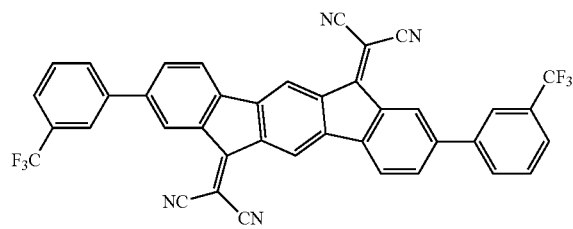
(A-121)
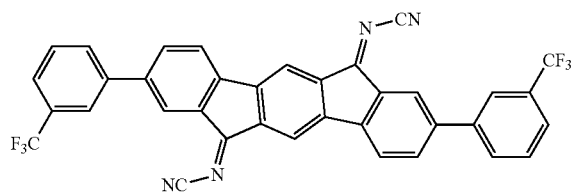
(A-122)
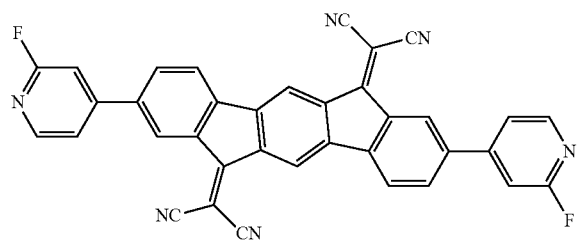
(A-123)
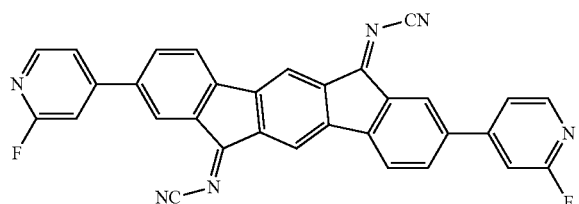
(A-124)
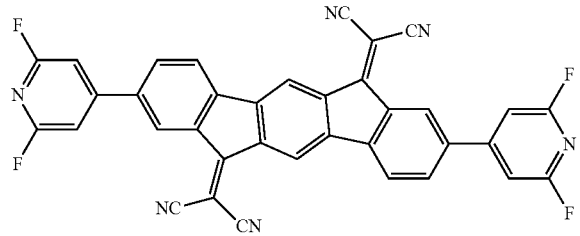
(A-125)
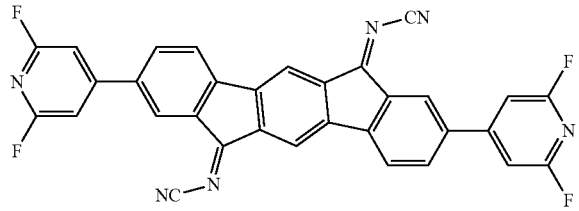
(A-126)
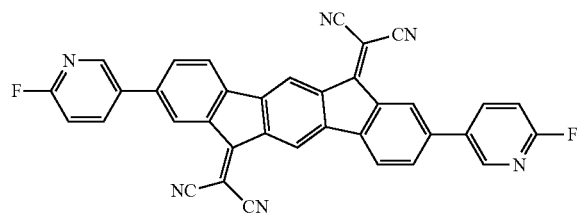
(A-127)
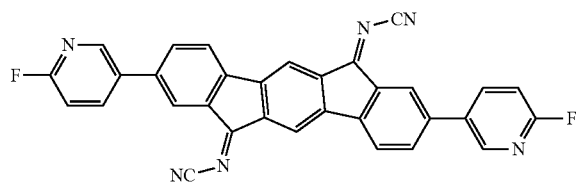
(A-128)
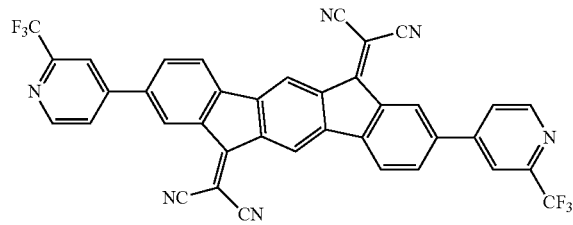
(A-129)
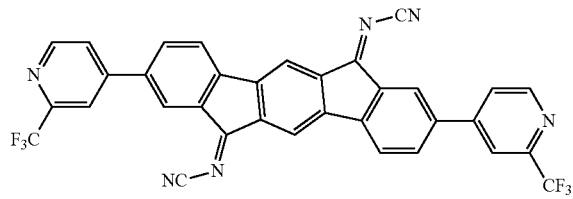
(A-130)
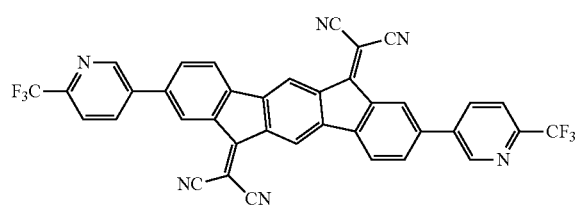
(A-131)

-continued
(A-132)
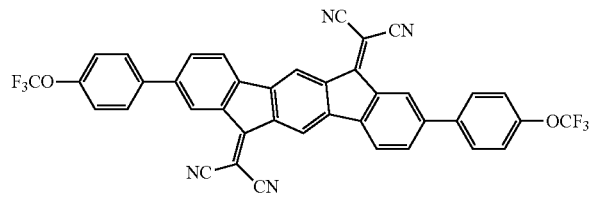
(A-133)
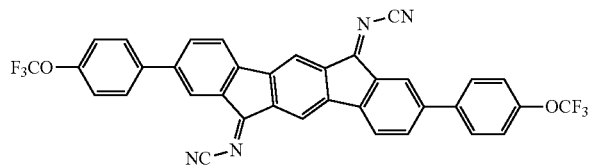
(A-134)
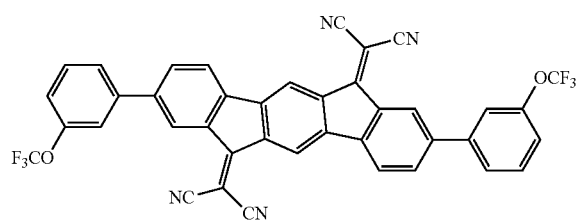
(A-135)
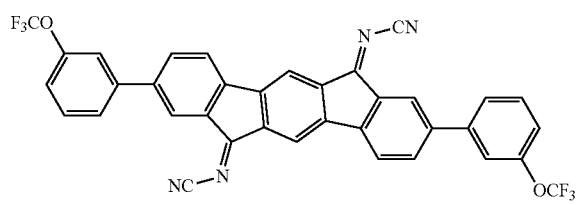
(A-136)
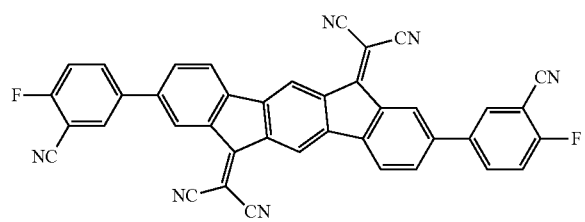
(A-137)
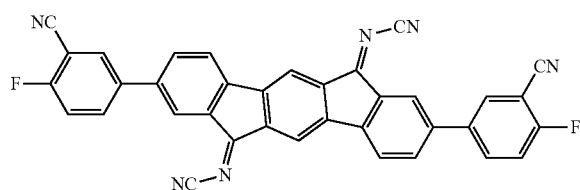
(A-138)
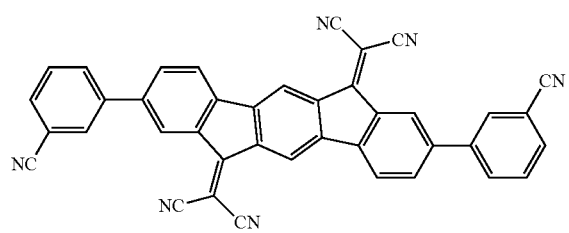
(A-139)
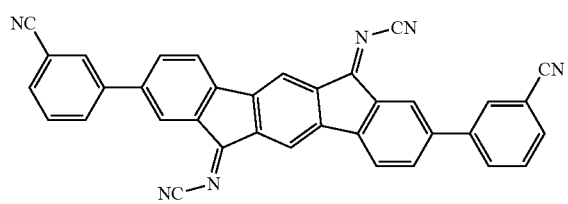
(A-140)
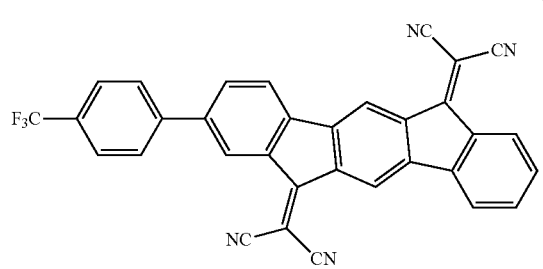
(A-141)
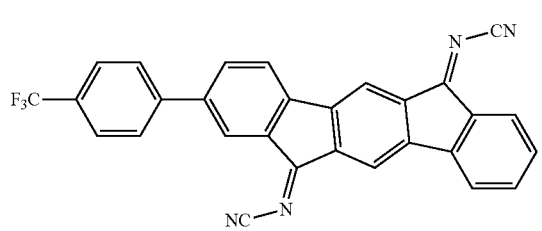
(A-142)
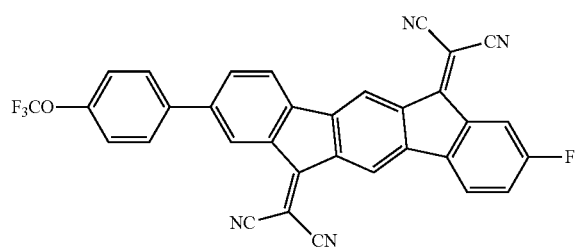
(A-143)
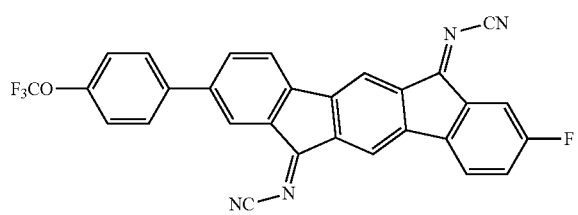

-continued
(A-144)
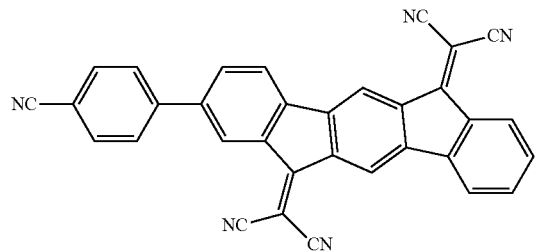
(A-145)
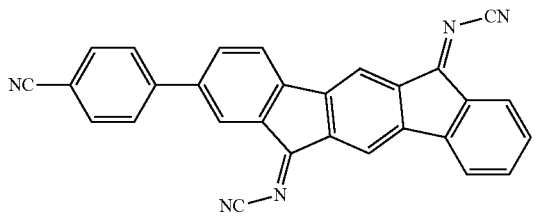
(A-146)
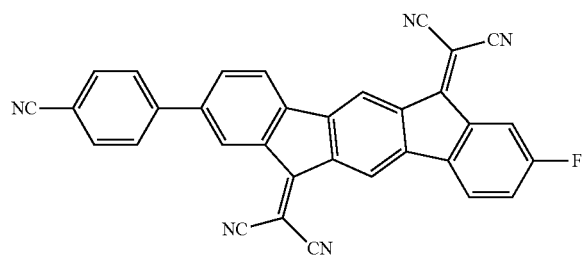
(A-147)
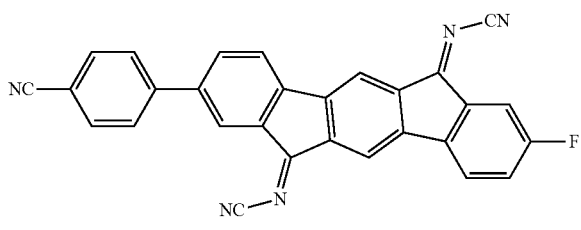
(A-148)
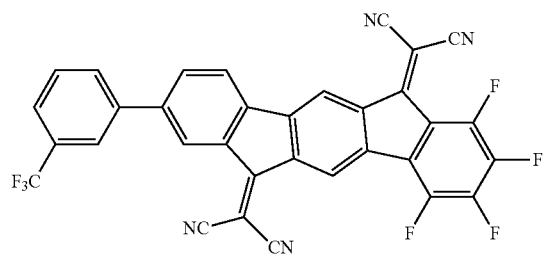
(A-149)
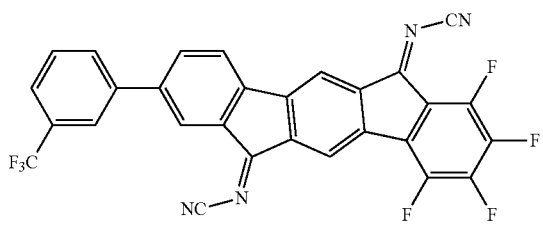
(A-150)
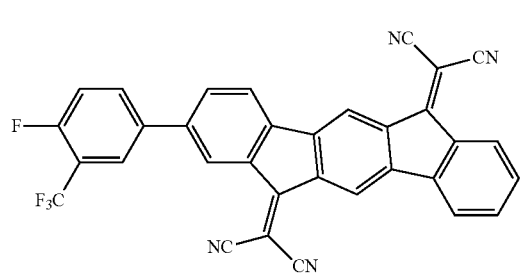
(A-151)
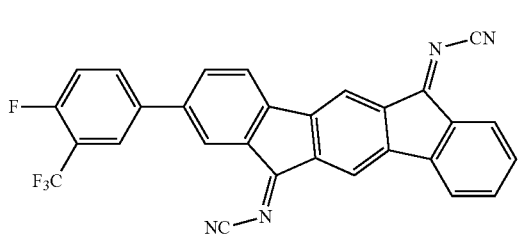
(A-152)
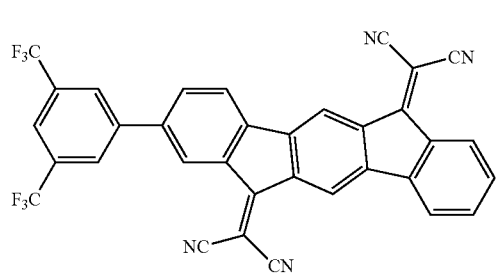
(A-153)
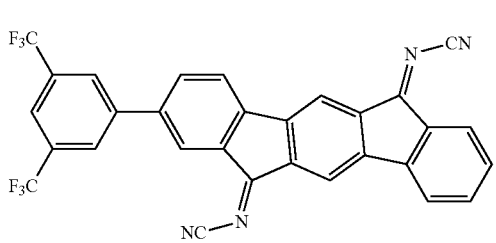
(A-154)
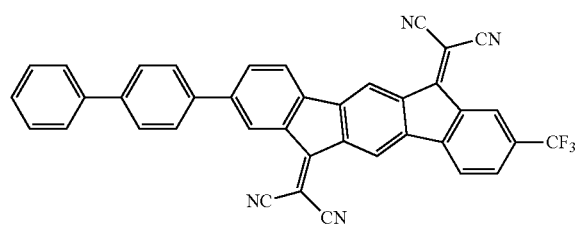
(A-155)
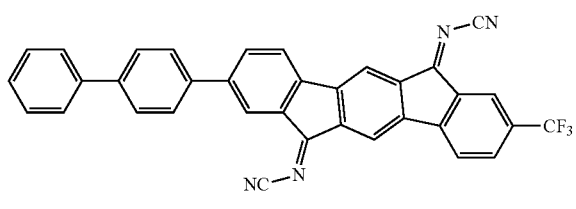

-continued
(A-156)
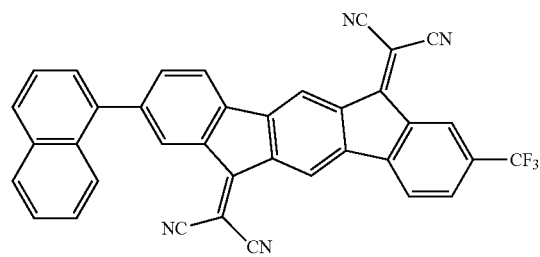
(A-157)
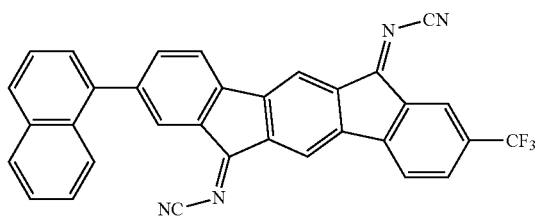
(A-158)
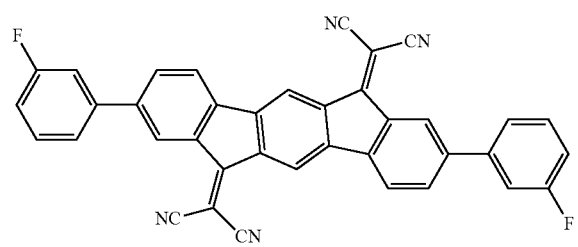
(A-159)
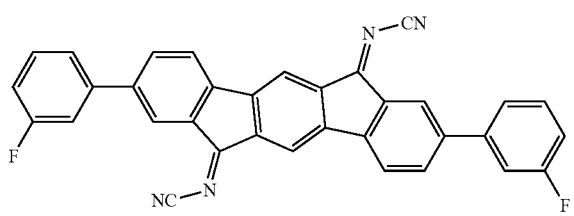
(A-160)
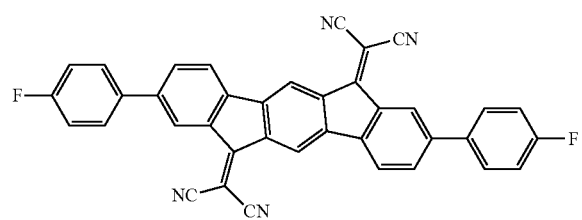
(A-161)
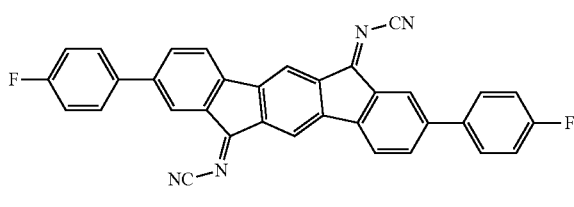
(A-162)
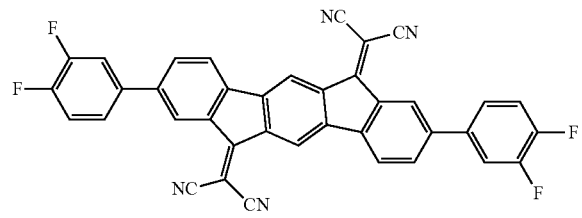
(A-163)
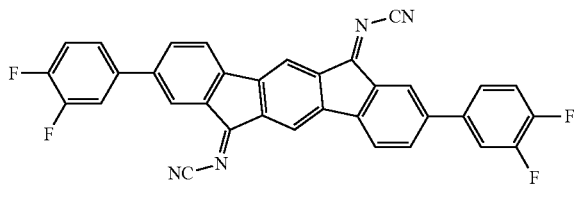
(A-164)
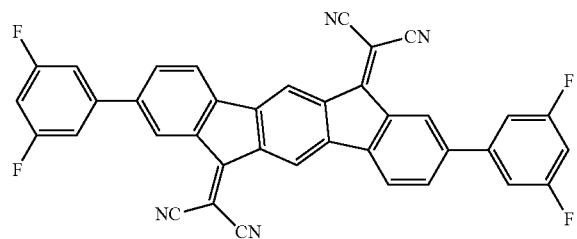
(A-165)
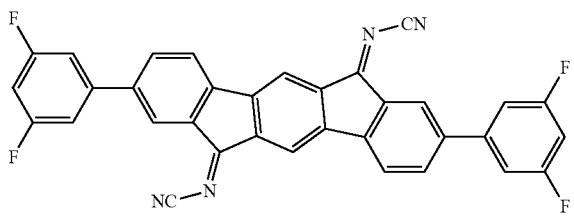
(A-166)
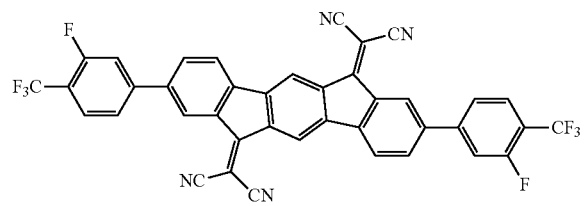
(A-167)
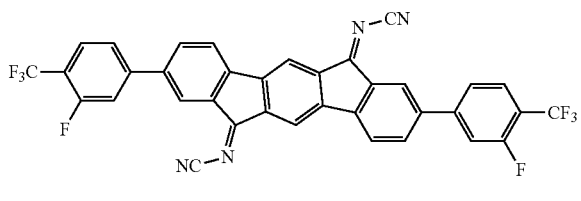

-continued
(A-168)
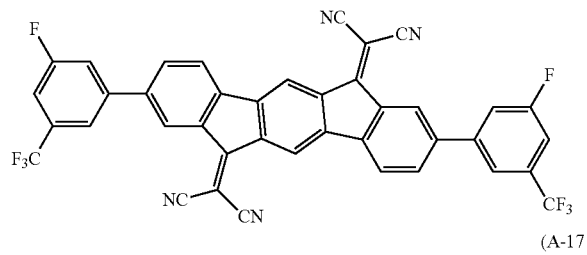
(A-169)
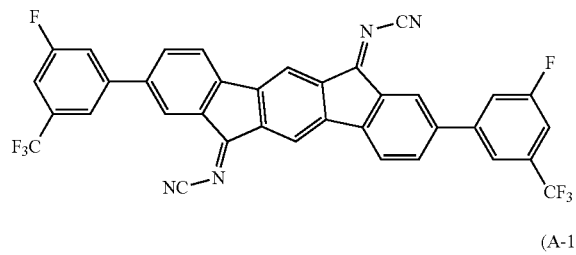
(A-171)
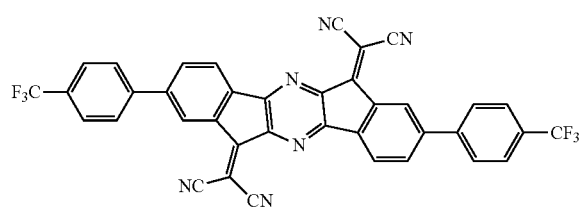
(A-172)
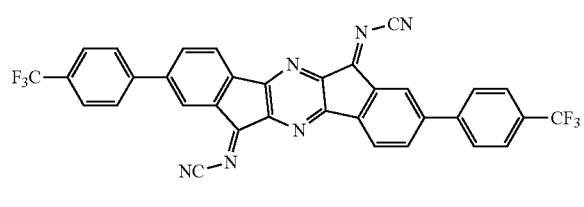
(A-173)
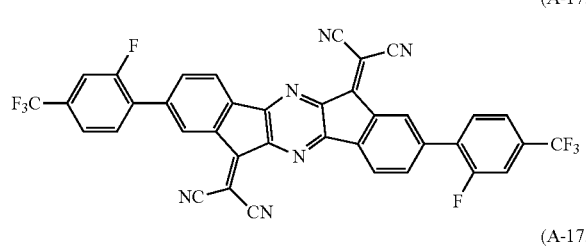
(A-174)
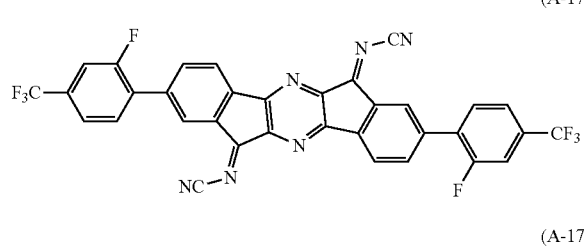
(A-175)
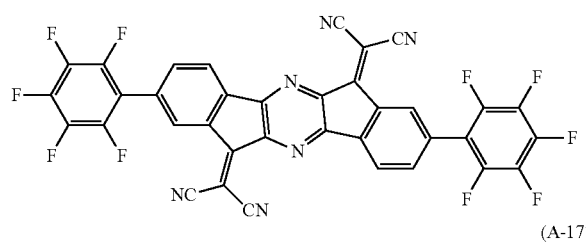
(A-176)
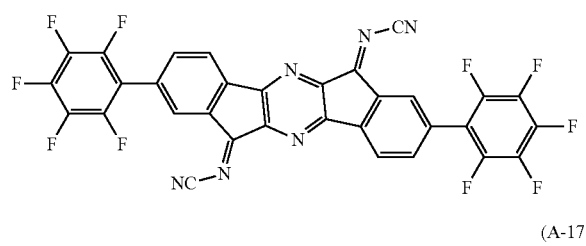
(A-177)
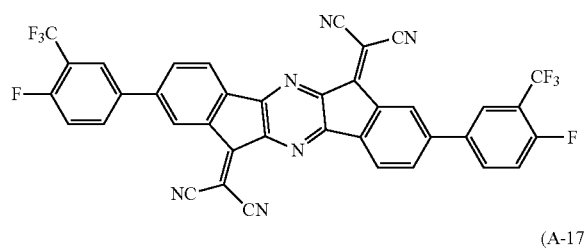
(A-178)
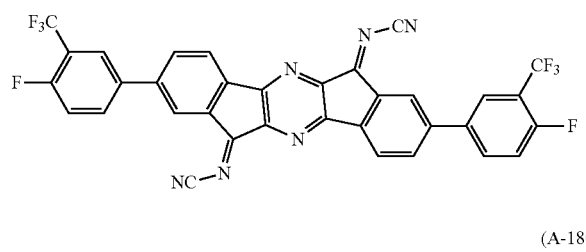
(A-179)
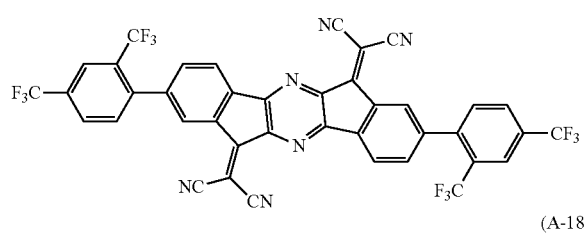
(A-180)
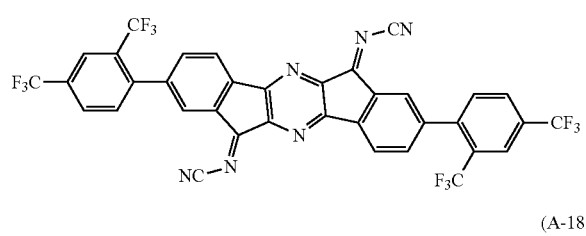
(A-181)
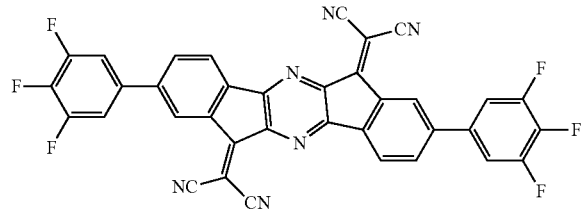
(A-182)
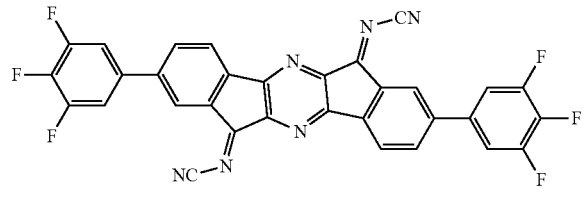

-continued
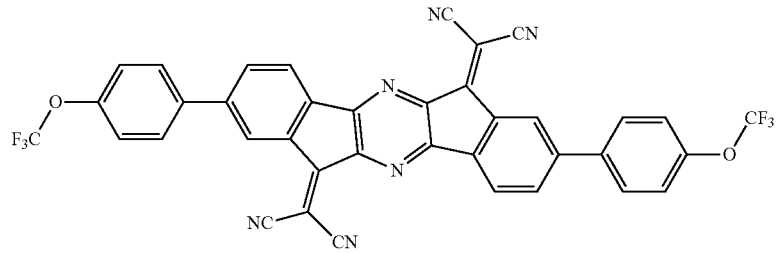
(A-183)
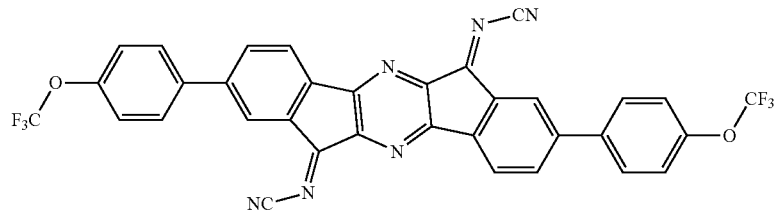
(A-184)
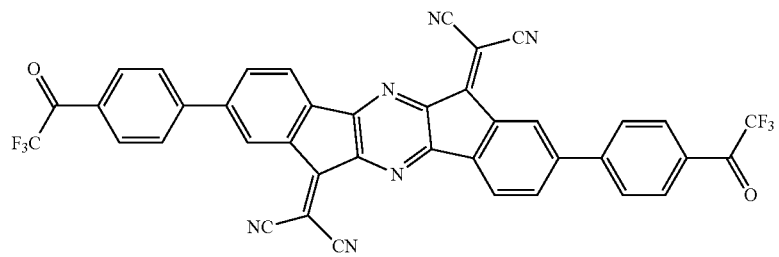
(A-185)
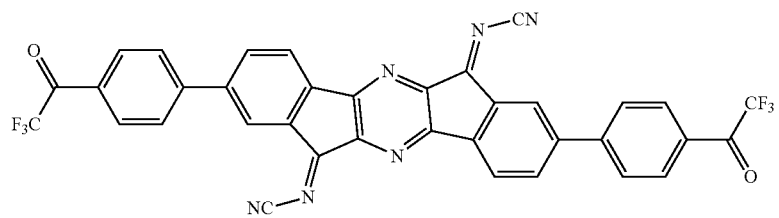
(A-186)
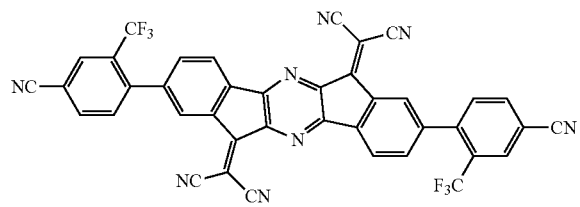
(A-187)
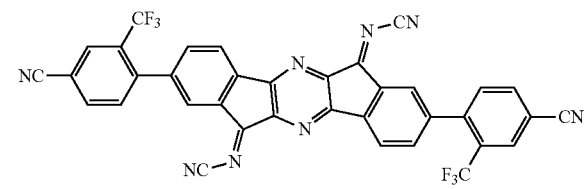
(A-188)
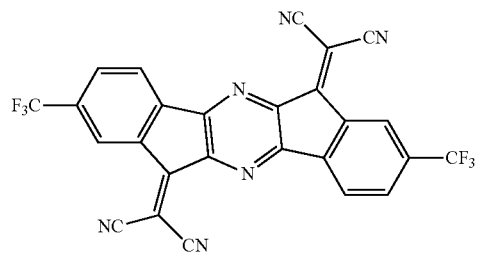
(A-189)
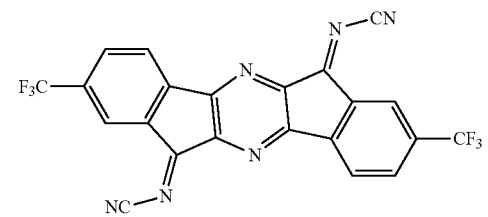
(A-190)

-continued
(A-191) 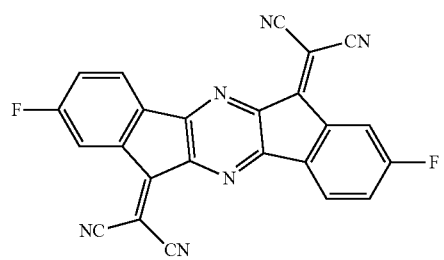
(A-192) 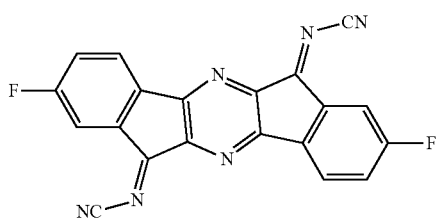
(A-193) 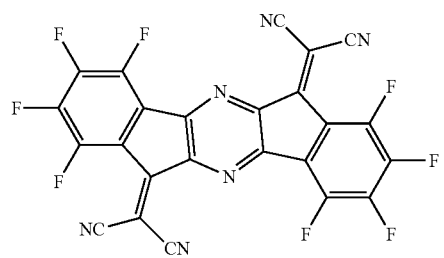
(A-194) 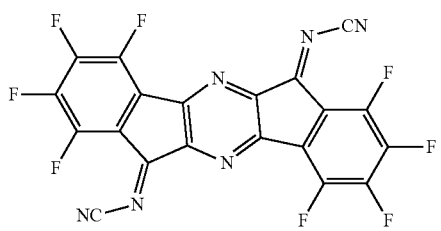
(A-195) 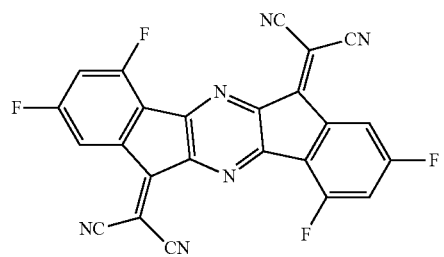
(A-196) 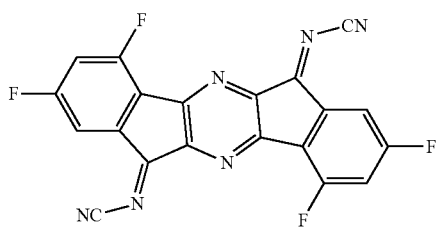
(A-197) 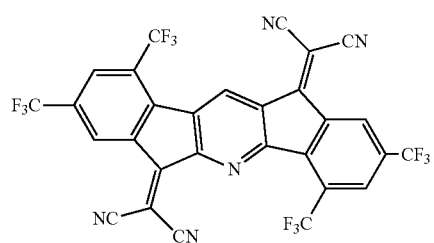
(A-198) 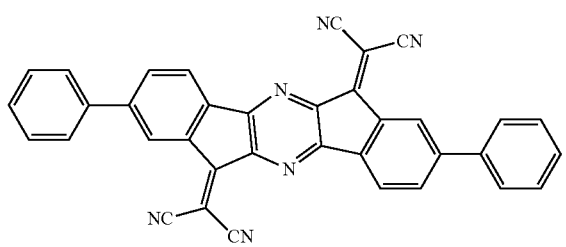
(A-199) 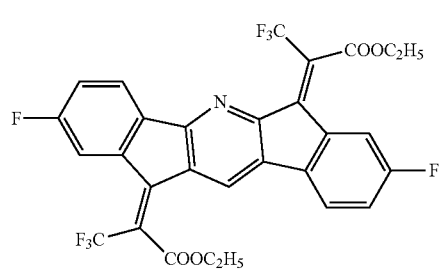
(A-200) 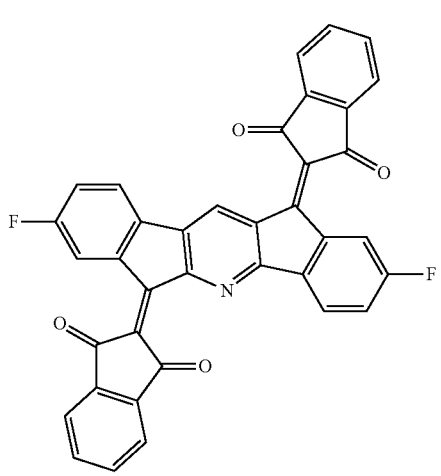

-continued
(A-201)
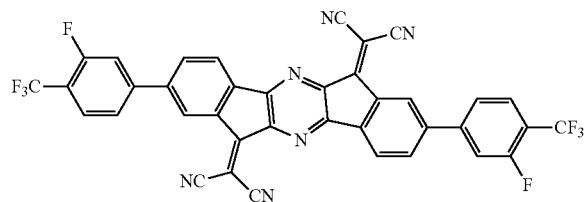
(A-202)
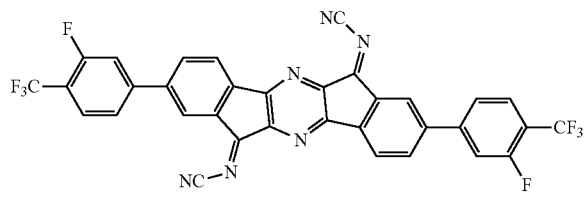
(A-203)
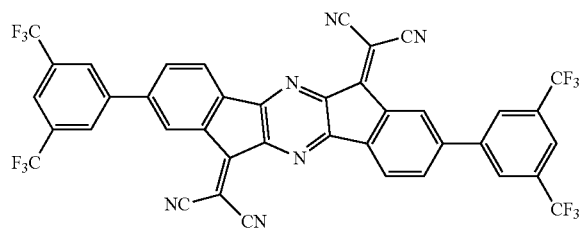
(A-204)
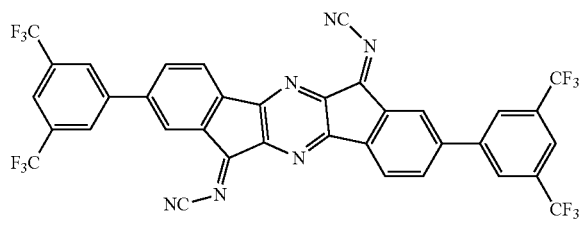
(A-205)
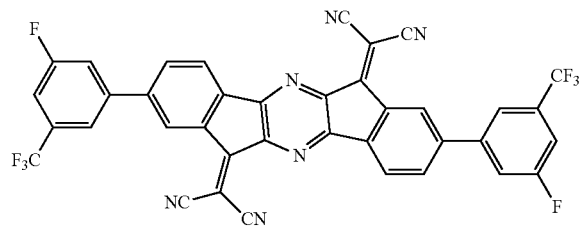
(A-206)
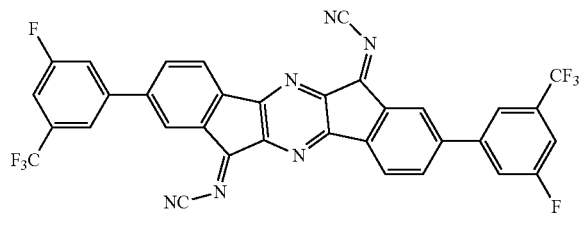
(A-207)
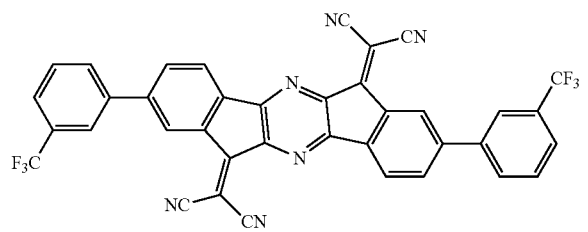
(A-208)
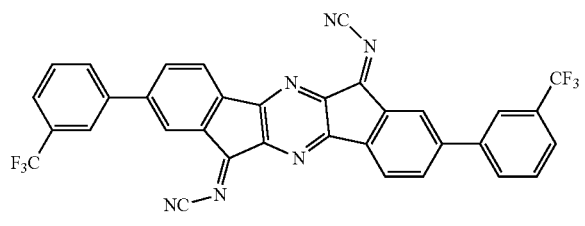
(A-209)
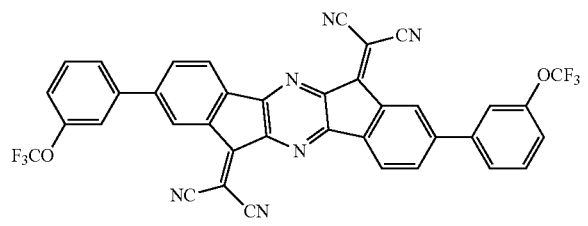
(A-210)
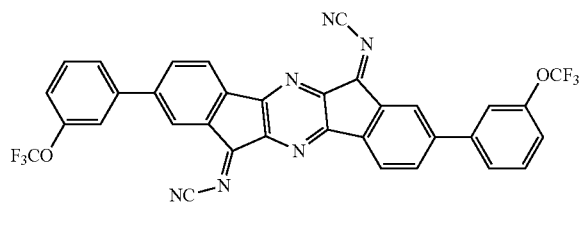
(A-211)
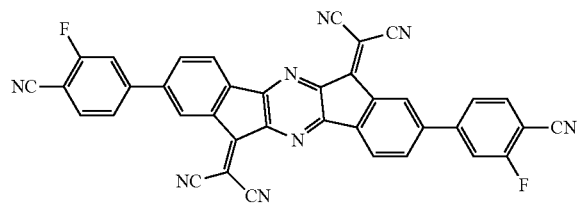
(A-212)

-continued
(A-213)
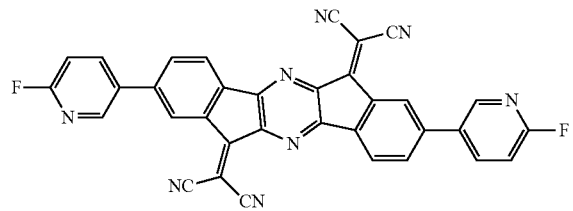
(A-214)
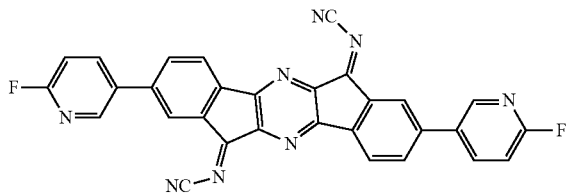
(A-215)
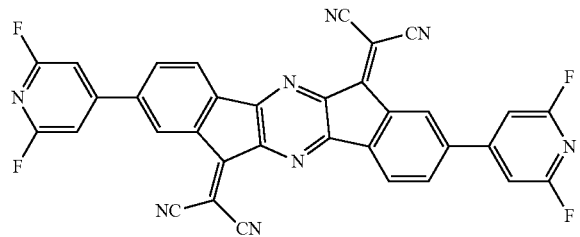
(A-216)
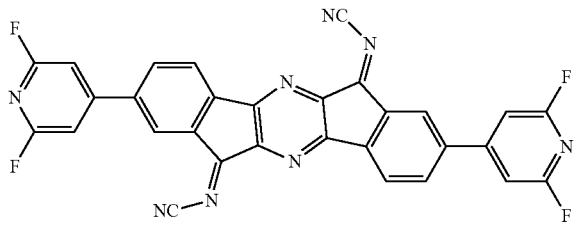
(A-217)
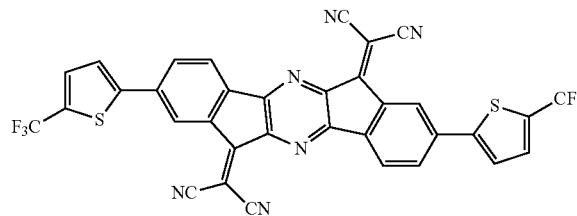
(A-218)
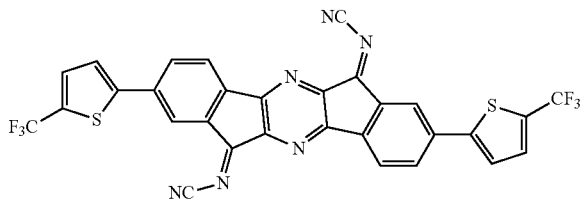
(A-219)
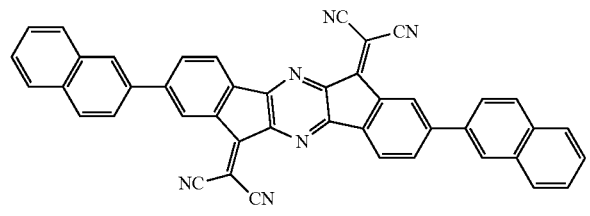
(A-220)
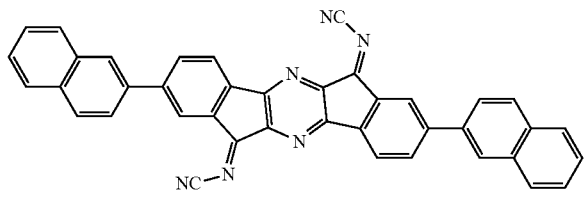
(A-221)
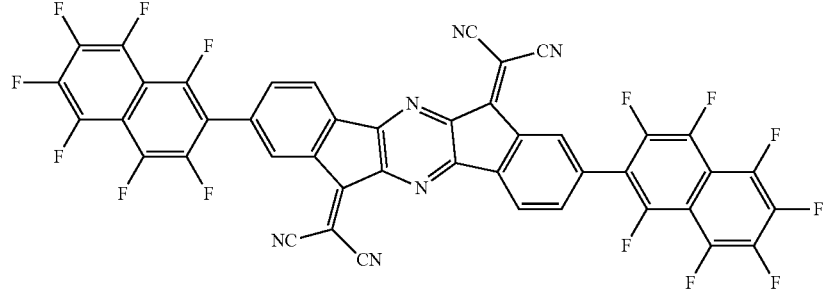
(A-222)
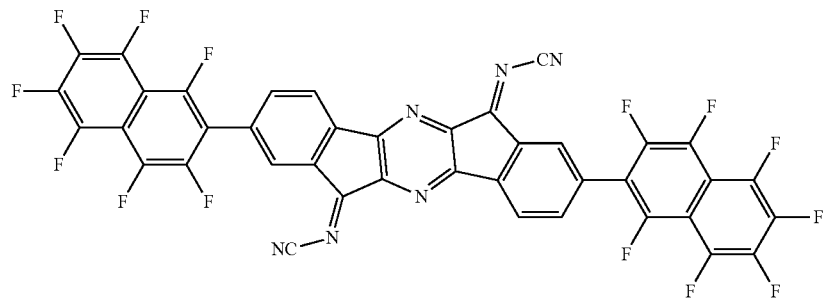

-continued
(A-223)
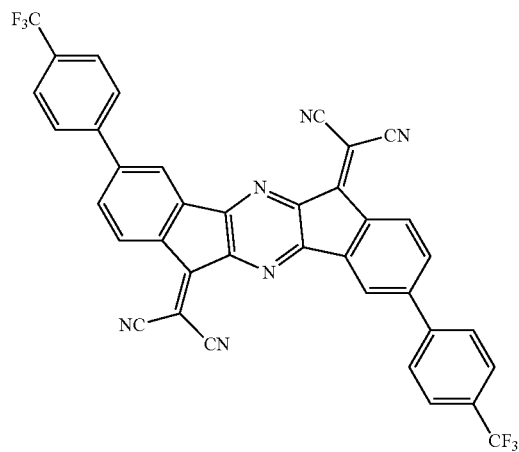
(A-224)
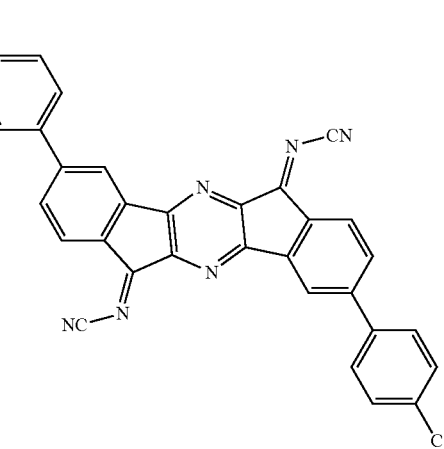
(A-225)
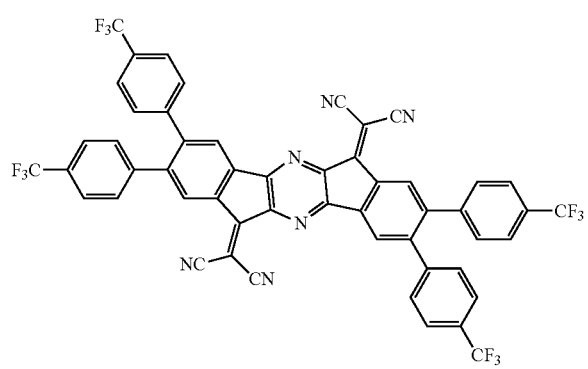
(A-226)
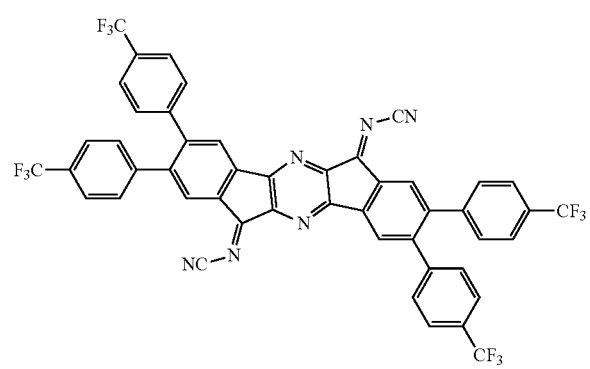
(A-227)
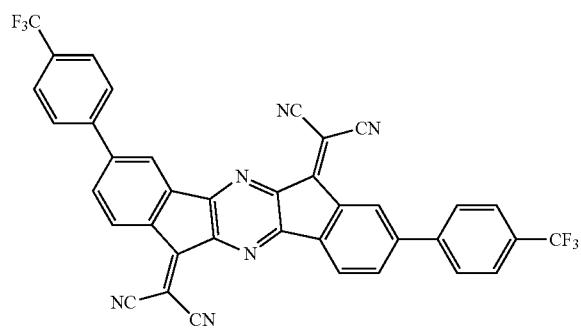
(A-228)
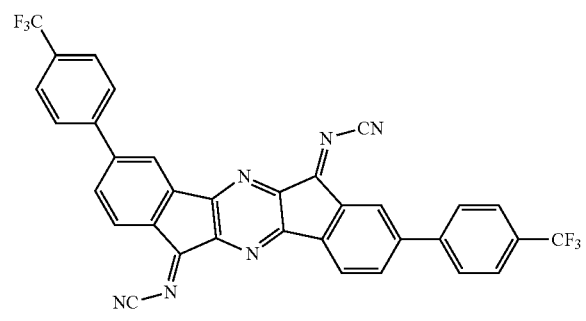
(A-229)
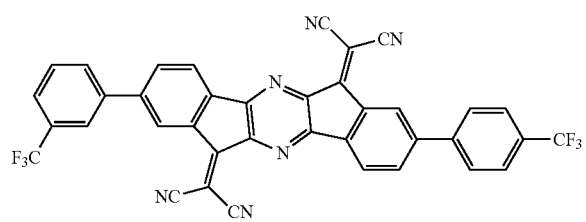
(A-230)
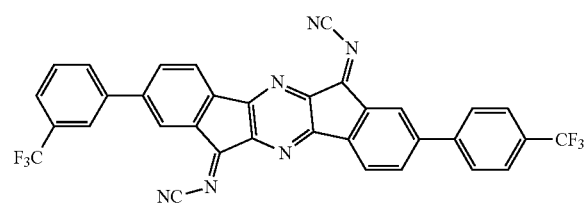
(A-231)
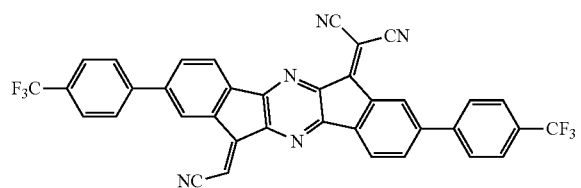
(A-232)
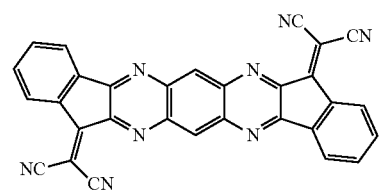

-continued
(A-233) 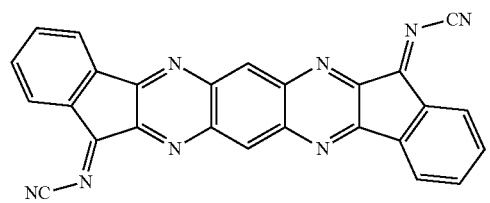
(A-234)
(A-235) 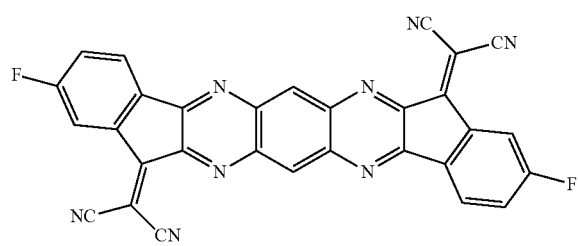
(A-236)
(A-237) 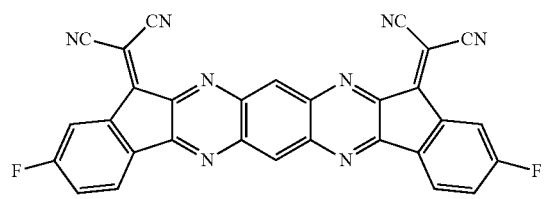
(A-238) 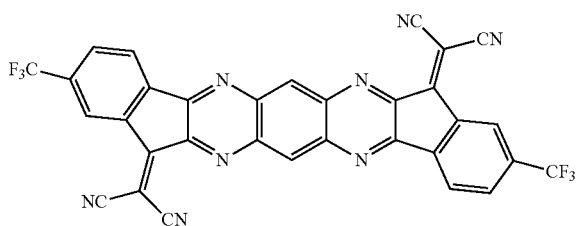
(A-239) 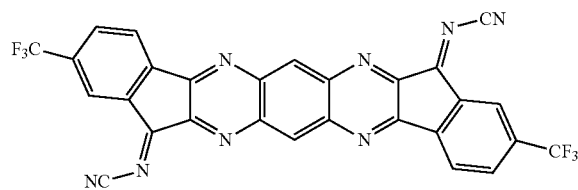
(A-240) 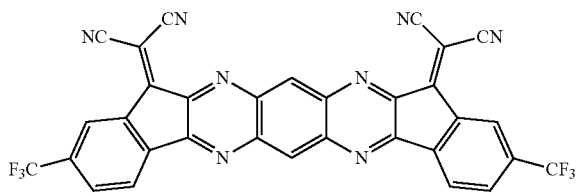
(A-241) 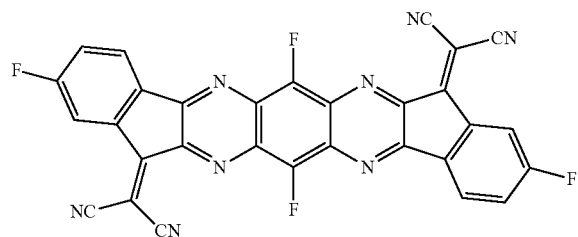
(A-242)
(A-243) 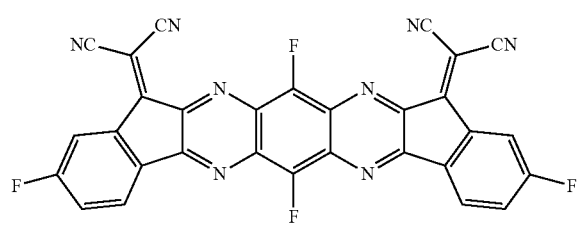

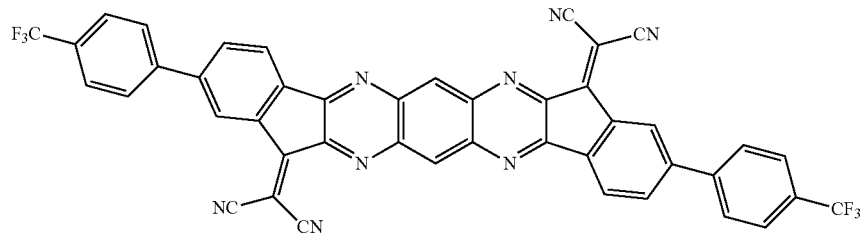
(A-244)
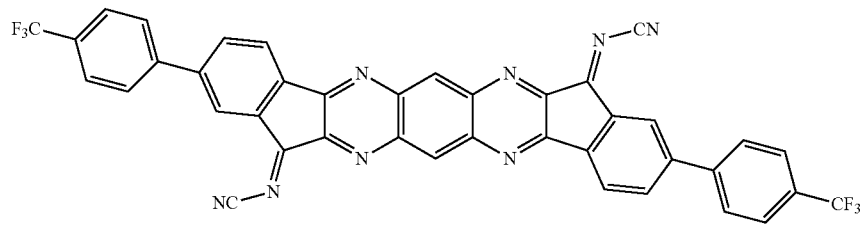
(A-245)
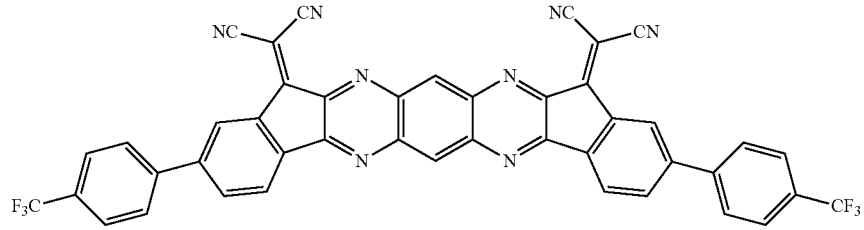
(A-246)
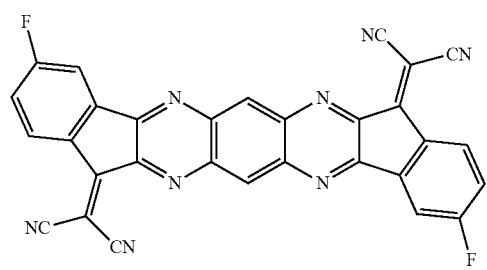
(A-247)
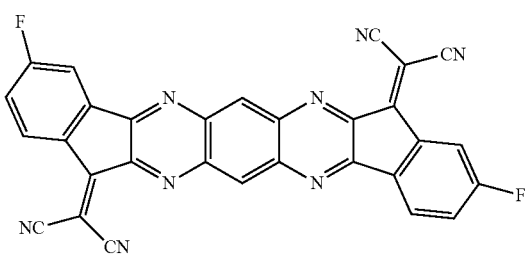
(A-248)
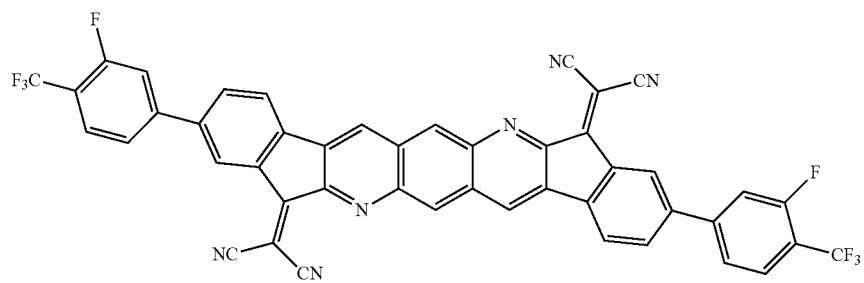
(A-249)

-continued

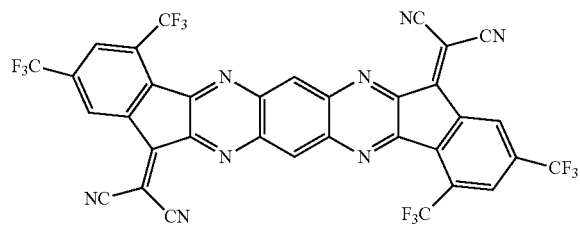
(A-250)

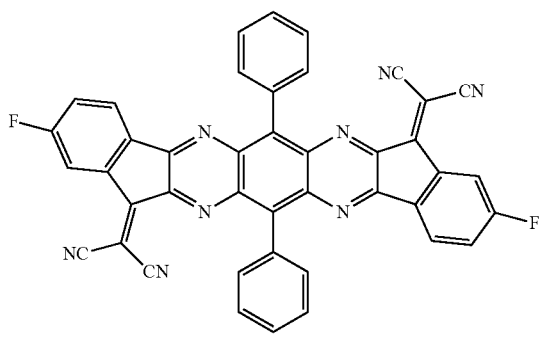
(A-251)

The compound represented by the formula (IV) can be synthesized by referring to WO2010/064655 and WO2009/011327.

The P layer may be a layer comprising only the compound represented by the formula (IV) or may be a layer comprising a mixture of the compound represented by the formula (IV) and other materials. In the invention, it is preferred that the P layer be a layer comprising the compound represented by the formula (IV) and at least one hole-transporting material.

As the hole-transporting material, the materials used in the hole-transporting region mentioned above can be used. Among these materials, an aromatic tertiary amine compound is preferable.

The content of the compound represented by the formula (IV) in the P layer is 0.1 wt % to 100 wt %, with 10 wt % to 70 wt % being particularly preferable.

The thickness of the P layer is preferably 1 nm to 50 nm, with 5 nm to 20 nm being particularly preferable.

In the invention, it is preferred that at least one of emitting units have a hole-transporting layer, and that the P layer of the charge-generating layer be in contact with the hole-transporting layer. For example, as in the case of an organic EL device 1 shown in FIG. 1, it is preferred that the hole-transporting layer 31B of the second emitting unit 30B be in contact with the P layer 42 of the charge-generating layer. Due to such a configuration, injection of holes from the charge-generating layer to the hole-transporting layer 31B of the second emitting unit 30B can be conducted efficiently, whereby a lowering in driving voltage of the device is realized.

The charge-generating layer may be formed only of two layers, i.e. the N layer and the P layer. An intermediate layer may be provided between the N layer and the P layer.

(Cathode)

As the cathode, one comprising a metal having a small work function (4 eV or less), an alloy, a conductive compound or a mixture thereof is used as the electrode material. Specific examples of the electrode material include, but are not limited thereto, sodium, sodium-potassium alloys, magnesium, lithium, magnesium-silver alloys, aluminum, aluminum/aluminum oxide, aluminum/lithium alloys, indium and rare earth metals.

The cathode may be formed by forming a thin film of the electrode material by deposition, sputtering, or the like.

When outcoupling light from the emitting layer through the cathode, it is preferable that the cathode have a light transmittance of more than 10%. The sheet resistance of the cathode is preferably several hundred $\Omega/\square$ or less. The thickness of the cathode is normally 10 nm to 1 μm, and preferably 50 to 200 nm.

(Other Constitution Elements)

In the invention, between the cathode and the organic layer, an electron-injecting layer formed of an insulator or a semiconductor may be provided. Due to provision of such a layer, leakage of electric current can be effectively prevented, whereby electron-injection property can be improved.

As such an insulator, it is preferable to use at least one metal compound selected from the group consisting of an alkali metal chalcogenide, an alkaline earth metal chalcogenide, a halide of an alkali metal and a halide of an alkaline earth metal. It is preferred that the electron-injecting layer be formed of these alkali metal chalcogenides or the like, since the electron-injecting property can be further improved.

Specifically, as preferable alkali metal chalcogenides, $Li_2O$, LiO, $Na_2S$, $Na_2Se$ and NaO can be given. As preferable alkaline earth metal chalcogenides, CaO, BaO, SrO, BeO, BaS and CaSe can be given, for example. As preferable halides of an alkali metal. LiF, NaF, KF, CsF, LiCl, KCl and NaCl can be given, for example. As preferable halides of an alkaline earth metal, a fluoride such as $CaF_2$, $BaF_2$, $SrF_2$, $Mg F_2$ and $BeF_2$ and a halide other than a fluoride can be given, for example.

As the semiconductor constituting the electron-injecting layer, an oxide, a nitride or a nitric oxide containing at least one element selected from Ba, Ca, Sr, Yb, Al, Ga, In, Li, Na, Cd, Mg, Si, Ta, Sb and Zn, or the like can be given, for example. They can be used singly or in combination of two or more.

Further, it is preferred that an inorganic compound constituting the electron-injecting layer be a finely-crystallized or amorphous insulating thin film.

As such an inorganic compound, the above-mentioned alkali metal chalcogenide, alkaline earth metal chalcogenide, halide of an alkali metal and halide of an alkaline earth metal or the like can be given, for example.

The configuration of the organic EL device of the invention is explained hereinabove by referring to the organic EL device 1 shown in FIG. 1. The invention is not restricted to the organic EL device 1. For example, although two emitting units are formed in the organic EL device 1, three or more emitting units may be formed.

Figure 2:
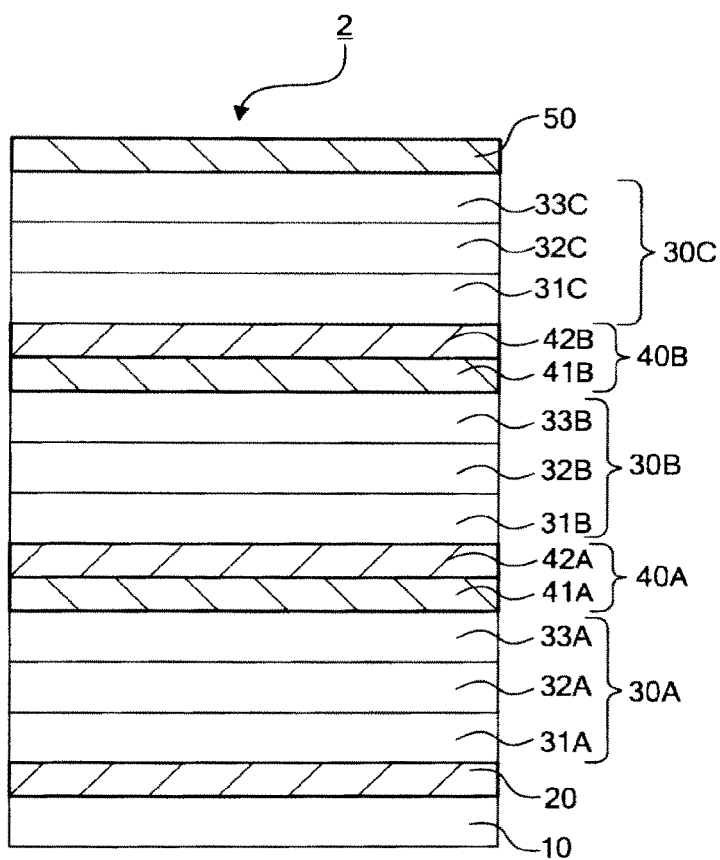
FIG. 2 is a schematic cross-sectional view showing another embodiment of the organic EL device according to the invention.

FIG. 2 is a schematic cross-sectional view of the organic EL device according to the second embodiment of the invention.

In an organic EL device 2, on a substrate 10, an anode 20, a first emitting unit 30A, a first charge-generating layer 40A, a second emitting unit 30B, a second charge-generating layer 40B, a third emitting unit 30C and a cathode 50 are provided in this sequence. The organic EL device 2 has the same configuration as the organic EL device 1 shown in FIG. 1, except that three emitting units are provided and two charge-generating layers are provided. That is, the first charge-generating layer 40A (N layer 41A, P layer 42A) corresponds to the above-mentioned charge-generating layer 40, and the second charge-generating layer 40B (N layer 41B, P layer 42B) and the third emitting unit 30C (hole-transporting layer 31C, emitting layer 32C and electron-transporting layer 33C) are respectively the same as those mentioned above.

In this embodiment, for example, by allowing the three emitting units to emit different colors of light, i.e. red, green and blue, a white-emitting EL device having an excellent color rending property, that is, capable of emitting light of three wavelength regions in a well-harmonized manner, is obtained.

The organic EL device of the invention exhibits excellent effects in particular when a plurality of devices are formed on a substrate as in the case of a pixel in a display.

Figure 3:
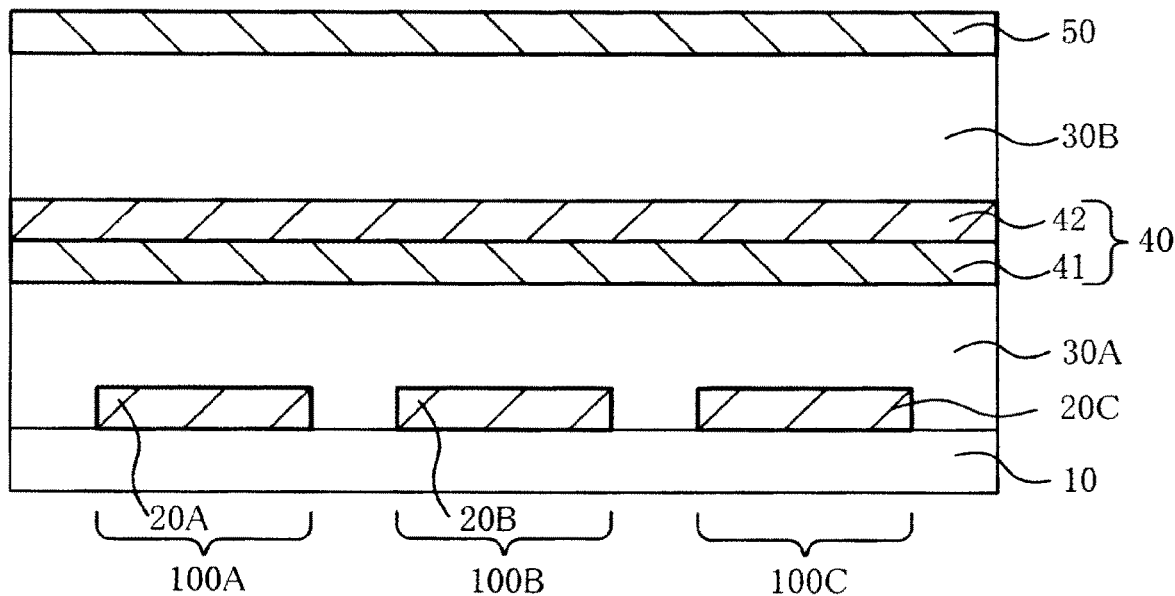
FIG. 3 is a schematic view showing an example in which three organic EL devices are formed on a substrate.

FIG. 3 is a schematic view showing an example in which three organic EL devices are formed on a substrate.

On the substrate 10, anodes 20A, 20B and 20C that have been patterned in a striped shape are provided. On the substrate 10 and each anode, the first emitting unit 30A, the charge-generating layer 40 and the second emitting unit 30B are formed in this sequence as the common elements. On the second emitting unit 30B, the cathode 50 is formed in a striped manner such that it crosses orthogonally with the anode 20.

The organic EL devices A to C emit light when a voltage is applied to the opposing anodes 20A to 20C and the cathode 50. For example, the device B emits light when a voltage is applied between the anode 20B and the cathode 50.

In the case of a device in which conventional materials such as a transparent conductor such as ITO are used in the charge-generating layer, charges are flown to adjacent devices through the charge-generating layer that is formed as the common layer for the devices, and a problem arises that an adjacent device, that is not supposed to emit light, emits light. As a result, luminous efficiency is lowered or color purity is lowered when the device is used in a display.

In the organic EL device of the invention, by using the compound represented by the formula (I) or (II) mentioned above in the N layer of the charge-generating layer, leakage of charges to adjacent devices can be suppressed.

The organic EL device of the invention is particularly preferable as an emitting element of a color display utilizing a color filter.

Figure 4:
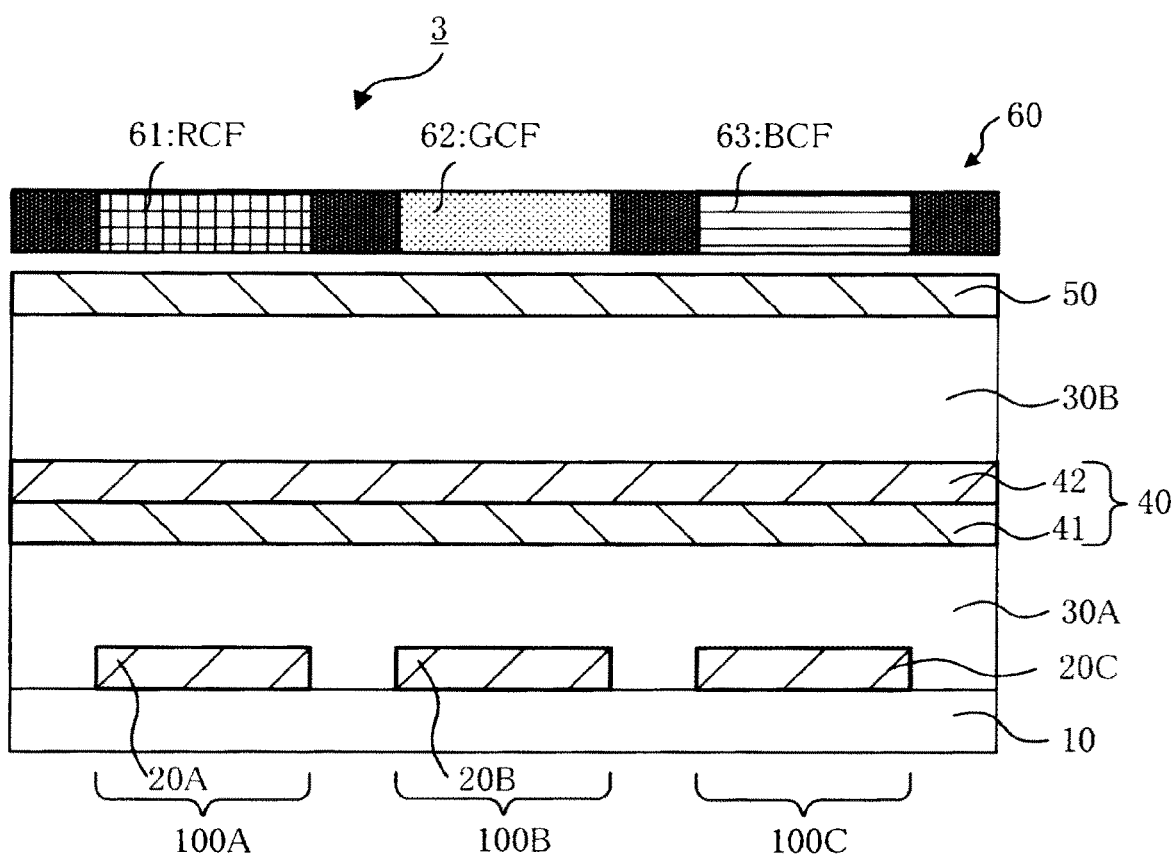
FIG. 4 is a schematic cross-sectional view of a color display using the organic EL device of the invention.

FIG. 4 is a cross-sectional view of a color display using the organic EL device of the invention.

The color display is formed by providing, on the light-outcoupling side of the organic EL device shown in FIG. 3, a color filter 60 having a red color filter (RCF) 61, a green color filter (GCF) 62 and a blue color filter (BCF) 63. In this embodiment, by allowing the emission color of the first emitting unit 30A to be yellow and the emission color of the second emitting unit 30B to be blue, a white color-emitting organic EL device is obtained. By the color filter, from the white color light, only desired light of color is outcoupled outside a display.

As mentioned above, the organic EL device of the invention can suppress leakage of charges to adjacent devices, as mentioned above. That is, since it is possible to suppress unnecessary emission of adjacent devices and to allow only desired devices (pixels) to emit light, color reproducibility of a display can be improved.

The organic EL device of the invention can be fabricated by a known method. Specifically, the anode or the cathode can be formed by a method such as deposition or sputtering. Each of the organic layers of the emitting unit or the like can be formed by the vacuum vapor deposition method, the spin coating method, the casting method, the LB method or the like.

EXAMPLES

Blue Organic EL Device

Examples 1 to 15 and Comparative Examples 1 to 3

A bottom-emission type organic EL device in which emission is outcoupled from the substrate having the layer structure shown in FIG. 1 was fabricated. The structures of the organic compounds used in Example 1 are shown below.

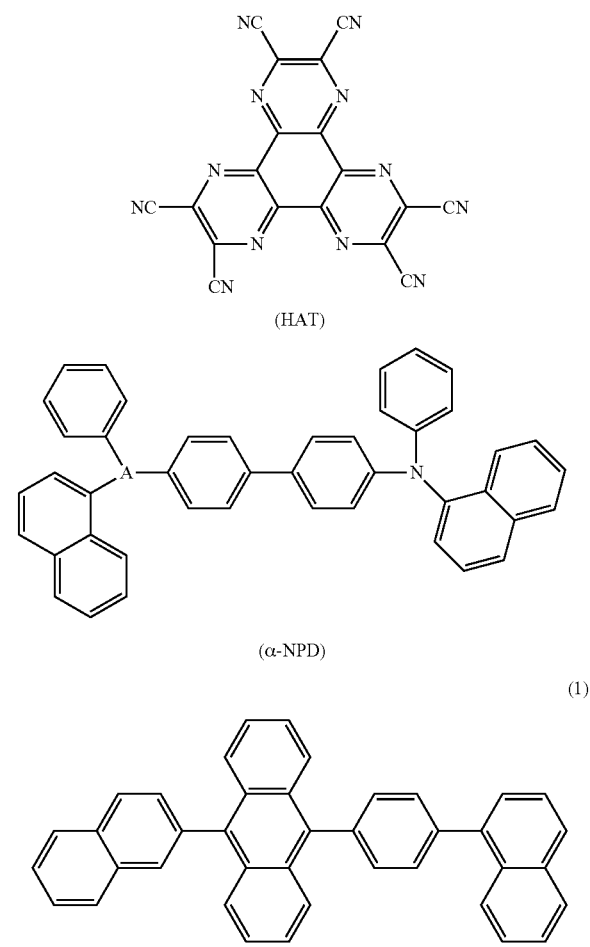

-continued (2)

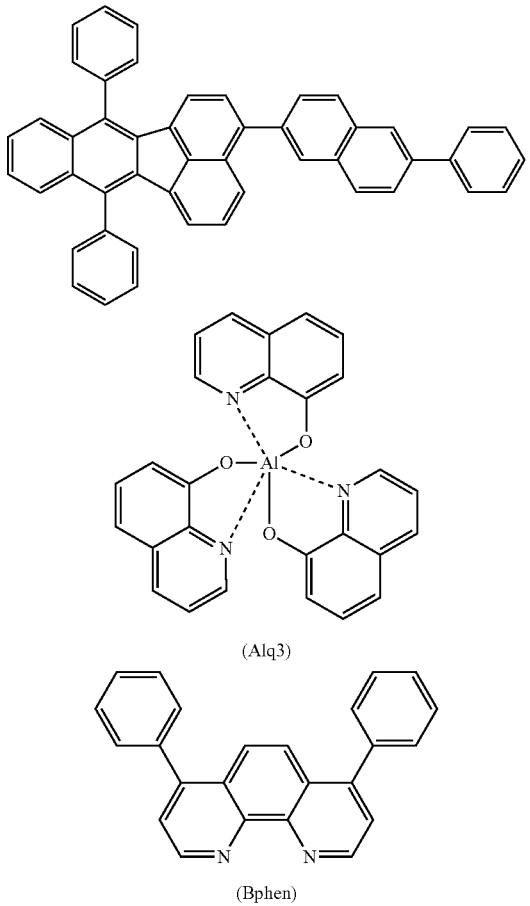

(Alq3)

(Bphen)

On a glass substrate having a dimension of 30 mm×30 mm, ITO was formed in a thickness of 240 nm as an anode. Subsequently, by deposition of SiO$_2$, a cell for an organic EL device in which other parts than emitting regions of 2 mm×2 mm are masked by an insulating film (not shown) was fabricated.

On the anode, as the hole-injecting layer, hexanitrileazatriphenylene (HAT) having the above-mentioned structure was formed in a thickness of 10 nm.

On the hole-injecting layer, a blue-emitting unit (first emitting unit) formed of a hole-transporting layer, a blue-emitting layer and an electron-transporting layer was formed.

Specifically, as the hole-transporting layer, the above-mentioned α-NPD was formed into a 90 nm-thick film by the vacuum vapor deposition method (deposition speed: 0.2 to 0.4 nm/sec).

Subsequently, on the hole-transporting layer, a blue-emitting layer was formed. As the host for the emitting layer, the compound represented by the above formula (1) was used, and as the dopant for the emitting layer, the compound represented by the above formula (2) was used. Vacuum deposition was conducted such that the amount of the dopant added became 5% in terms of film thickness ratio, whereby an emitting layer having a film thickness of 30 nm was formed.

Subsequently, on the blue-emitting layer, as an electron-transporting layer, Alq3 was formed into a 30 nm-thick film.

Subsequent to the formation of the blue emitting unit, a charge-generating layer was formed. On the electron-transporting layer of the emitting unit, the N layer and the P layer were formed in this sequence by using the compound shown in Table 1. In Comparative Example 1, the N layer and the P layer were not formed. The thickness of each of the N layer and the P layer was 10 nm. The N layer is a mixture layer of the compound shown in Table 1 and Li.

Subsequent to the formation of the charge-generating layer, a second blue-emitting unit was formed. The second blue-emitting unit was formed in the same manner as in the formation of the first blue-emitting unit mentioned above.

Thereafter, LiF was formed into a film having a thickness of about 0.3 nm (deposition speed: 0.01 nm/sec) by vapor vacuum deposition, and then, Al was formed into a film having a thickness of 200 nm by the vapor vacuum deposition to form a cathode having a two-layer structure, whereby an organic EL device was fabricated.

For the organic EL devices fabricated, the voltage (V), the luminance (cd/m$^2$) at a current density of 10 mA cm$^{-2}$, and the relative luminance value after 300-hour driving at 50 mA/cm$^2$ were measured. The results are shown in Table 1.

TABLE 1

| | Emission color of first emitting unit | Constitution of charge-generating layer | | Emission color of second emitting unit | Emission color of entire device | Voltage (V) | Luminance (cd/m$^2$) | Relative value of luminance |
|---|---|---|---|---|---|---|---|---|
| | | N layer 10 nm | P layer 10 nm | | | | | |
| Ex. 1 | Blue | (B-1) + Li (2%) | (A-55) | Blue | Blue | 8.2 | 1605 | 95% |
| Ex. 2 | Blue | (B-1) + Li (2%) | (A-57) | Blue | Blue | 8.2 | 1600 | 95% |
| Ex. 3 | Blue | (B-1) + Li (2%) | (A-84) | Blue | Blue | 8.2 | 1605 | 95% |
| Ex. 4 | Blue | (B-1) + Li (2%) | (A-177) | Blue | Blue | 8.2 | 1600 | 95% |
| Ex. 5 | Blue | (B-2) + Li (2%) | (A-55) | Blue | Blue | 8.2 | 1600 | 95% |
| Ex. 6 | Blue | (B-2) + Li (2%) | (A-84) | Blue | Blue | 8.2 | 1600 | 95% |
| Ex. 7 | Blue | (B-2) + Li (2%) | (A-177) | Blue | Blue | 8.2 | 1600 | 95% |
| Ex. 8 | Blue | (B-17) + Li (2%) | (A-55) | Blue | Blue | 8.2 | 1610 | 95% |
| Ex. 9 | Blue | (B-17) + Li (2%) | (A-57) | Blue | Blue | 8.2 | 1610 | 95% |
| Ex. 10 | Blue | (B-17) + Li (2%) | (A-84) | Blue | Blue | 8.2 | 1610 | 95% |
| Ex. 11 | Blue | (B-17) + Li (2%) | (A-177) | Blue | Blue | 8.2 | 1610 | 95% |
| Ex. 12 | Blue | (B-37) + Li (2%) | (A-55) | Blue | Blue | 8.2 | 1600 | 95% |
| Ex. 13 | Blue | (B-37) + Li (2%) | (A-84) | Blue | Blue | 8.2 | 1600 | 95% |
| Ex. 14 | Blue | (B-37) + Li (2%) | (A-177) | Blue | Blue | 8.2 | 1600 | 95% |

TABLE 1-continued

| | Emission color of first emitting unit | Constitution of charge-generating layer | | Emission color of second emitting unit | Emission color of entire device | Voltage (V) | Luminance (cd/m²) | Relative value of luminance |
|---|---|---|---|---|---|---|---|---|
| | | N layer 10 nm | P layer 10 nm | | | | | |
| Ex. 15 | Blue | (B-75) + Li (2%) | (A-84) | Blue | Blue | 8.3 | 1600 | 95% |
| Comp. Ex. 1 | Blue | None | None | — | Blue | 4.0 | 800 | 95% |
| Comp. Ex. 2 | Blue | Alq3 + Li (2%) | (A-55) | Blue | Blue | 10.2 | 1480 | 83% |
| Comp. Ex. 3 | Blue | BPhen + Li (2%) | (A-84) | Blue | Blue | 9.5 | 1500 | 87% |

From the results of Examples 1 to 15 and Comparative Example 1, it was revealed that, by fabricating a tandem device utilizing the charge-generating layers including the N layer and the P layer shown in the table, an efficiency that was twice as large as that of a single unit device was obtained, and the voltage also doubled. As a result, it has been confirmed that the tandem device utilizing the charge-generating layer including the N layer and the P layer shown in the Table functioned as a MPE device.

From the results of Examples 1 to 15 and Comparative Examples 2 and 3, it was revealed that, in the charge-generating layer, if Alq or BPhen was used in the N layer, although the device functioned as a MPE device, an increase in driving voltage and shortening of the life were observed. From these results, it was confirmed that the compounds in Examples 1 to 15 were excellent as the N layer of the charge-generating layer.

White-Emitting Organic EL Device

Examples 16 and 17 and Comparative Examples 4 and 5

Organic EL devices were fabricated in the same manner as Example 1, except that a glass substrate in which a lower electrode was patterned so that the resolution became 100 ppi was used and the following yellow-emitting unit was formed instead of the first blue-emitting unit.

Fabrication of a Patterned Electrode Substrate

On a glass substrate, a planarized insulating film was formed. No specific restrictions are imposed on the planarized insulating film material as long as it is a positive-photoresist type insulating material. In this example, polyimide was formed in a thickness of 2.0 μm. Specifically, on the substrate, polyimide was applied by a spin-coating method, exposed by an exposing apparatus, developed by means of a paddle developer, and patterned in a prescribed shape. In order to cure the polyimide, main calcination was conducted in a clean baking furnace, whereby a 2.0 μm-thick planarized insulating film was formed.

Subsequently, lower electrodes were formed on the planarized insulating film. Specifically, ITO was formed on the planarized insulating film in a thickness of 240 nm, and patterned into a prescribed shape by using a common lithography technology, followed by etching to form lower electrodes.

Between the patterned lower electrodes (ITO), polyimide was formed in a thickness of 2.0 μm, whereby an insulating layer between electrodes was formed. Specifically, the insulating layer between electrodes was formed as follows. On the substrate, polyimide was applied by a spin-coating method, exposed by an exposing apparatus and developed by means of a paddle developer, whereby the polyimide as the photosensitive insulating material was patterned into a desired shape. Subsequently, in order to cure the polyimide, main calcination was conducted in a clean baking furnace, whereby an insulating layer between electrodes was formed.

Formation of a Yellow-Emitting Unit

On the hole-injecting layer comprising the above-mentioned hexanitrileazatriphenylene (HAT), a yellow emitting unit comprising the hole-transporting layer, a yellow emitting layer and the electron-transporting layer (first emitting unit) was formed.

As the hole-transporting layer, the α-NPD mentioned above was formed into a 30 nm-thick film by the vacuum vapor deposition method (deposition speed: 0.2 to 0.4 nm/sec).

Subsequently, on the hole-transporting layer, a yellow-emitting layer was formed. As the host for the emitting layer and as the dopant for the emitting layer, a compound represented by the following formula (3) and a compound represented by the following formula (4) were respectively used. The compounds were vacuum-vapor-deposited such that the amount of the dopant added became 5% in terms of film thickness ratio, whereby an emitting layer having a thickness of 30 nm was formed.

Subsequently, on the yellow emitting layer, as an electron-transporting layer, Alq3 was formed into a 20 nm-thick film.

Hereinbelow, a charge-generating layer and a second emitting unit shown in Table 2 were formed in the same manner as in Example 1, whereby an organic EL device was fabricated.

(3)

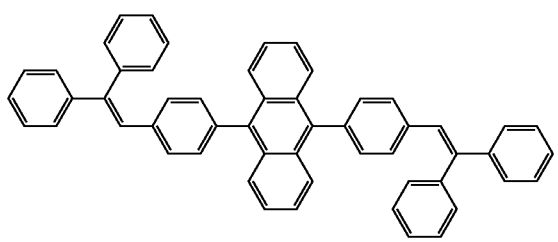

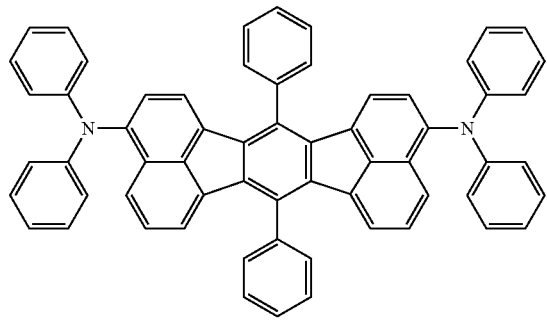

(4)

For the organic EL devices fabricated, the voltage (V), the luminance (cd/m$^2$) at a current density of 10 mA cm$^{-2}$ and the relative luminance value after 300-hour driving at 50 mA/cm$^2$ were measured. Further, the CIE chromaticity of emission was measured by means of a spectroradiometer. The results are shown in Table 2.

In each pixel of the organic EL device fabricated in Examples 16, 17 and Comparative Examples 5 and 6, a red color filter, a green color filter and a blue color filter were formed. Color reproducibility encompassed by each of red, green and blue colors was evaluated in terms of NTSC ratio. An organic EL device was fabricated as follows.

At positions that serve as openings of a glass substrate, color filters of each of RGB were formed in sequence. On the color filters, a planarized insulating film was formed, whereby unevenness in the color filters was removed to be flat. As a result, a glass substrate having color filters was obtained. Thereafter, a patterned electrode substrate was fabricated in the same manner as in Example 5, and an emitting unit was further formed.

In order to enable the thus fabricated device to be driven in a passive-type manner, a upper electrode and an lower electrode were provided, and each pixel of RGB was enabled to emit light individually. As a result, emission of a single color of each of RGB becomes possible.

Figure 5:
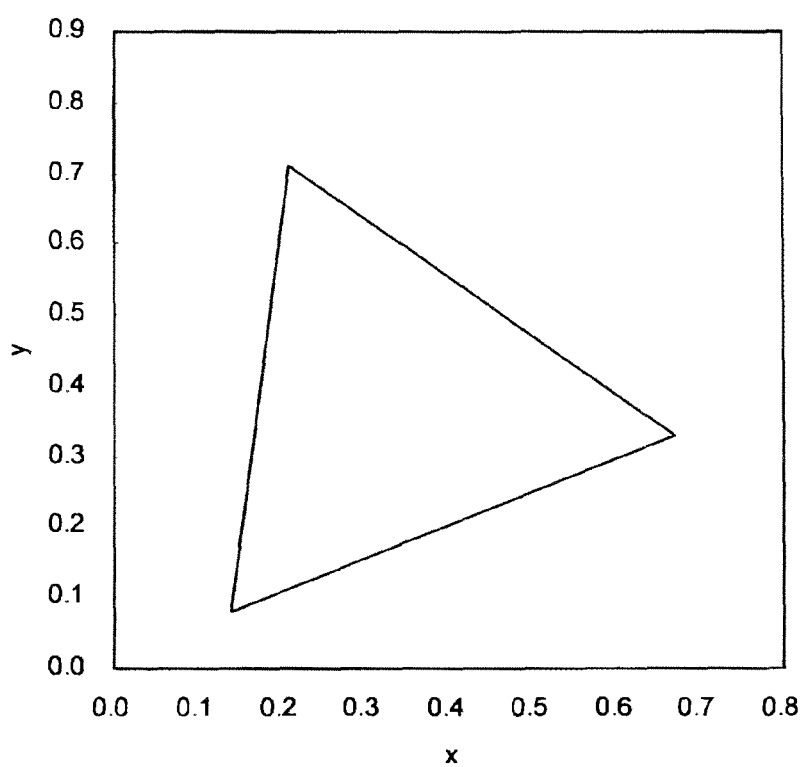
FIG. 5 is a view showing a region obtained by combining chromaticity coordinates of red, green and blue determined by the NTSC in an XYZ chromaticity diagram.

Here, the NTSC ratio means the ratio (unit: %) of color reproduction range of a display relative to the area surrounded by the three primary colors of the NTSC (National Television System Committee (NTSC) of the Americas) standard; red (0.670, 0.330), green (0.210, 0.710) and blue (0.140, 0.080). FIG. 5 shows the region obtained by connecting chromaticity coordinates of red, green and blue determined by the NTSC in the CIE-XYZ color diagram. This region is taken as 100%.

The results are shown in Table 2.

From the results of Examples 16 and 17, it was confirmed that, by fabricating a tandem device utilizing the charge-generating layer including the N layer and the P layer shown in Table 2, the synergistic effect of the yellow single unit device and the blue single unit device could be obtained, whereby white emission was obtained.

In Comparative Examples 4 and 5, since HAT was used in the P layer of the charge-generating layer, although the device functioned as a MPE device, as compared with the Examples, when a display panel was fabricated by providing a color filter, the NTSC ratio was lowered in respect of color reproducibility. The reason therefor is assumed to be as follows. Since the resistances of the HAT was too low, carriers leaked to adjacent pixels through the charge-generating layer, causing the adjacent pixels to emit light. As a result, when red, green or blue color was displayed as a single color, the purity of each color was deteriorated.

In contrast, in Examples 16 and 17, since the N layer of the invention was used, lowering in NTSC ratio was small even if HAT was used in the P layer. The reason therefor is assumed to be as follows. When charges are generated associated with withdrawal of electrons from the adjacent hole-transporting layer by the P layer, it becomes possible for the N layer to inject smoothly electrons that are withdrawn by the P layer to the emitting unit provided on the side nearer to the anode. As a result, electrons and holes do not accumulate in the interface between the N layer and the P layer, and holes that are generated simultaneously with generation of electrons in the charge-generating layer can be smoothly injected to the emitting unit provided on the side nearer to the cathode. As a result, leakage of carriers through the P layer (HAT layer) can be suppressed, whereby emission of adjacent pixels can be suppressed, whereby lowering in color purity of each color when red, green or blue is displayed monochromatically.

From the above, in a stacked white emitting device, by using a layer including the N layer and the P layer shown in the Table in the charge-generating layer, it becomes possible to fabricate an organic EL display panel suffering less color mixing and having a high degree of color reproducibility.

INDUSTRIAL APPLICABILITY

The organic EL device of the invention can be used in a planar luminous body such as a flat panel display of a wall-hanging TV, a copier, a printer, a backlight of a crystal liquid display, or a light source of instruments, a displaying board, sign lighting or the like.

Although only some exemplary embodiments and/or examples of this invention have been described in detail above, those skilled in the art will readily appreciate that

TABLE 2

| | Emission color of first emitting unit | Constitution of charge-generating layer | | Emission color of second emitting unit | Emission color of entire device | Voltage (V) | Luminance (cd/m$^2$) | Relative value of luminance | Chromaticity coordinates (x, y) | NTSC ratio (%) |
|---|---|---|---|---|---|---|---|---|---|---|
| | | N layer 10 nm | P layer 10 nm | | | | | | | |
| Ex. 16 | Yellow | (B-13) + Li (2%) | HAT | Blue | White | 7.9 | 4300 | 95% | (0.246, 0.331) | 93 |
| Ex. 17 | Yellow | (B-75) + Li (2%) | HAT | Blue | White | 8 | 4300 | 95% | (0.246, 0.332) | 93 |
| Comp. Ex. 4 | Yellow | Alq3 + Li (2%) | HAT | Blue | White | 9.9 | 4120 | 83% | (0.246, 0.330) | 80 |
| Comp. Ex. 5 | Yellow | BPhen + Li (2%) | HAT | Blue | White | 9.2 | 4200 | 87% | (0.246, 0.330) | 80 | many modifications are possible in the exemplary embodiments and/or examples without materially departing from the novel teachings and advantages of this invention. Accordingly, all such modifications are intended to be included within the scope of this invention.

The documents described in the specification and a Japanese application on the basis of which the present application claims Paris convention priority are incorporated herein by reference in its entirety.

The invention claimed is:

1. An organic electroluminescence device comprising:
   an anode;
   a cathode;
   two or more emitting units that are disposed between the anode and the cathode, each unit having an emitting layer; and
   a charge-generating layer that is disposed between the emitting units, wherein the charge-generating layer comprises an N layer nearer to the anode and a P layer nearer to the cathode, and wherein the N layer is directly adjacent to the P layer, and
   the N layer comprises two percent Li and a compound represented by the following formula:

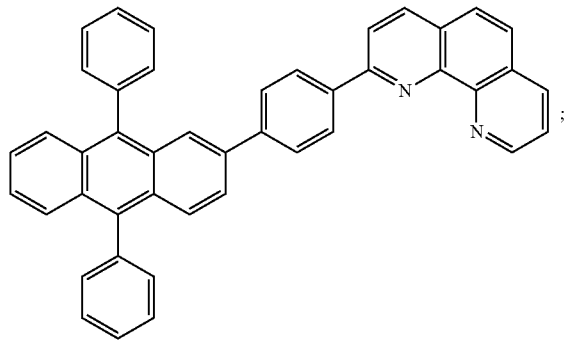 [SMILES: c1ccc(-c2c3ccccc3c(-c3ccccc3)c3cc(-c4ccc(-c5ccc6ccc7cccnc7c6n5)cc4)ccc23)cc1]

and the P layer comprises a compound represented by the following formula (HAT):

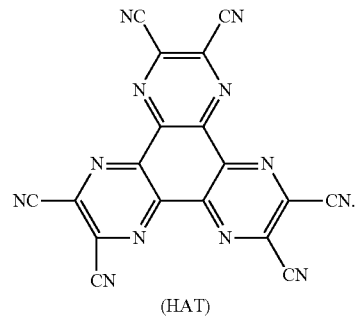

2. The organic electroluminescence device according to claim 1, wherein the N layer of the charge-generating layer comprises at least one of an electron-donating metal, an electron-donating metal compound and an electron-donating metal complex.

3. The organic electroluminescence device according to claim 2, wherein the N layer of the charge-generating layer comprises at least one of an alkali metal, an alkali earth metal, a simple substance of a rare earth metal, a compound of a rare earth metal and a complex of a rare earth metal.

4. The organic electroluminescence device according to claim 1, wherein a material constituting at least one of the emitting layers of the emitting units is different from a material constituting the emitting layer(s) of the other emitting unit(s).

5. The organic electroluminescence device according to claim 1, which emits white light.

6. The organic electroluminescence device according to claim 1, wherein the organic electroluminescence device has at least three of the emitting units, and wherein the charge-generating layer is between every set of the emitting units.

7. An organic electroluminescence device comprising:
   an anode;
   a cathode;
   two or more emitting units that are disposed between the anode and the cathode, each unit having an emitting layer; and
   a charge-generating layer that is disposed between the emitting units, wherein the charge-generating layer comprises an N layer nearer to the anode and a P layer nearer to the cathode, and wherein the N layer is directly adjacent to the P layer, and
   the N layer comprises two percent Li and a compound represented by the following formula:

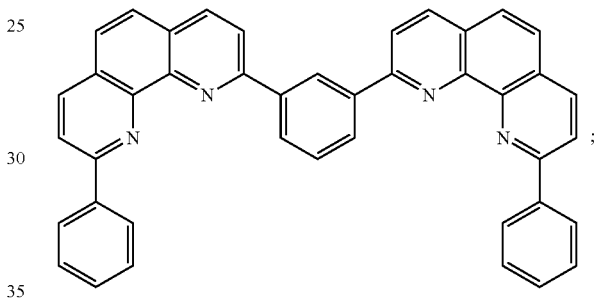

and the P layer comprises a compound represented by the following formula (HAT):

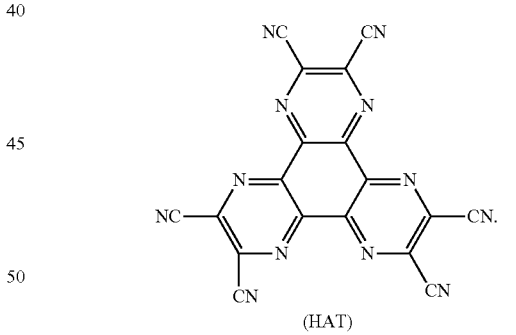

8. The organic electroluminescence device according to claim 1, wherein the charge-generating layer injects holes directly to the emitting unit arranged on a side nearer to the cathode of the charge-generating layer and injects electrons directly to the emitting unit arranged on a side nearer to the anode of the charge-generating layer.

9. The organic electroluminescence device according to claim 7, wherein the charge-generating layer injects holes directly to the emitting unit arranged on a side nearer to the cathode of the charge-generating layer and injects electrons directly to the emitting unit arranged on a side nearer to the anode of the charge-generating layer.

* * * * *